US012655417B2

(12) United States Patent
Diniz De Carvalho et al.

(10) Patent No.: US 12,655,417 B2
(45) Date of Patent: *Jun. 16, 2026

(54) METHODS OF CAPTURING CELL-FREE METHYLATED DNA AND USES OF SAME

(71) Applicants: University Health Network, Toronto (CA); Sinai Health System, Toronto (CA)

(72) Inventors: Daniel Diniz De Carvalho, Toronto (CA); Shu Yi Shen, Markham (CA); Rajat Singhania, Toronto (CA)

(73) Assignees: University Health Network, Toronto (CA); Sinai Health System, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 19/241,820

(22) Filed: Jun. 18, 2025

(65) Prior Publication Data

US 2025/0313825 A1 Oct. 9, 2025

Related U.S. Application Data

(63) Continuation of application No. 18/059,370, filed on Nov. 28, 2022, which is a continuation of application No. 17/519,350, filed on Nov. 4, 2021, now Pat. No. 11,560,558, which is a continuation of application No. 17/353,756, filed on Jun. 21, 2021, which is a continuation of application No. 16/098,620, filed as application No. PCT/CA2017/000108 on May 3, 2017, now Pat. No. 11,078,475.

(60) Provisional application No. 62/331,070, filed on May 3, 2016.

(51) Int. Cl.
| | |
|---|---|
| *C12N 15/10* | (2006.01) |
| *C12Q 1/6804* | (2018.01) |
| *C12Q 1/6806* | (2018.01) |
| *G01N 33/53* | (2006.01) |
| *C12Q 1/6886* | (2018.01) |
| *C40B 30/04* | (2006.01) |

(52) U.S. Cl.
CPC ......... *C12N 15/1003* (2013.01); *C12N 15/10* (2013.01); *C12N 15/1093* (2013.01); *C12Q 1/6804* (2013.01); *C12Q 1/6806* (2013.01); *G01N 33/5308* (2013.01); *C12Q 1/6886* (2013.01); *C12Q 2600/154* (2013.01); *C40B 30/04* (2013.01)

(58) Field of Classification Search
CPC ............ C12Q 1/68; C12N 15/10; C40B 30/04
See application file for complete search history.

(56) References Cited

U.S. PATENT DOCUMENTS

| | | | |
|---|---|---|---|
| 6,730,478 | B1 | 5/2004 | Lee et al. |
| 9,249,462 | B2 | 2/2016 | Patsalis et al. |
| 10,706,957 | B2 * | 7/2020 | Lo .......................... G16B 20/10 |
| 11,078,475 | B2 * | 8/2021 | Diniz De Carvalho ..................... |
| | | | G01N 33/5308 |
| 11,560,558 | B2 * | 1/2023 | Diniz De Carvalho .................... |
| | | | C12Q 1/6806 |
| 12,031,184 | B2 | 7/2024 | Diniz De Carvalho et al. |
| 12,227,737 | B2 | 2/2025 | Diniz De Carvalho et al. |
| 2003/0003455 | A1 | 1/2003 | Rundell et al. |
| 2003/0092019 | A1 | 5/2003 | Meyer et al. |
| 2003/0190616 | A1 | 10/2003 | Goggins et al. |
| 2011/0236903 | A1 | 9/2011 | McClelland et al. |
| 2012/0208711 | A1 | 8/2012 | Cortese et al. |
| 2012/0252015 | A1 | 10/2012 | Hindson et al. |
| 2012/0282613 | A1 | 11/2012 | Patsalis et al. |
| 2014/0080715 | A1 | 3/2014 | Lo et al. |
| 2014/0093873 | A1 | 4/2014 | Tynan et al. |
| 2015/0132754 | A1 | 5/2015 | Wang et al. |
| 2015/0299812 | A1 | 10/2015 | Talasaz |
| 2016/0017419 | A1 * | 1/2016 | Chiu ...................... C12Q 1/689 |
| | | | 506/8 |
| 2016/0032396 | A1 | 2/2016 | Diehn et al. |
| 2019/0005395 | A1 | 1/2019 | Dutkowski |
| 2019/0024127 | A1 | 1/2019 | Yeh |
| 2019/0071727 | A1 | 3/2019 | Lo et al. |
| 2020/0131582 | A1 | 4/2020 | Zhou et al. |
| 2020/0160936 | A1 | 5/2020 | Fang et al. |
| 2020/0165675 | A1 | 5/2020 | Marsh et al. |
| 2021/0156863 | A1 | 5/2021 | Dinz De Carvalho et al. |
| 2022/0119796 | A1 | 4/2022 | Diniz De Carvalho et al. |
| 2022/0177956 | A1 | 6/2022 | Frumkin et al. |

(Continued)

FOREIGN PATENT DOCUMENTS

| | | |
|---|---|---|
| CA | 3080215 A1 | 5/2019 |
| CN | 104781422 A | 7/2015 |

(Continued)

OTHER PUBLICATIONS

Butcher et al., AutoMeDIP-seq: A high-throughput, whole genome, DNA methylation assay. Method p. 626-552:223-231 (Year: 2010).*

(Continued)

*Primary Examiner* — Ethan C Whisenant
(74) *Attorney, Agent, or Firm* — WILSON SONSINI GOODRICH & ROSATI

(57) ABSTRACT

There is described herein, a method of capturing cell-free methylated DNA from a sample having less than 100 mg of cell-free DNA, comprising the steps of: subjecting the sample to library preparation to permit subsequent sequencing of the cell-free methylated DNA; adding a first amount of filler DNA to the sample, wherein at least a portion of the filler DNA is methylated; denaturing the sample; and capturing cell-free methylated DNA using a binder selective for methylated polynucleotides.

20 Claims, 34 Drawing Sheets

Specification includes a Sequence Listing.

(56) References Cited

U.S. PATENT DOCUMENTS

| | | | |
|---|---|---|---|
| 2022/0251665 A1 | 8/2022 | Diniz De Carvalho et al. |
| 2023/0024827 A1 | 1/2023 | Wilson et al. |
| 2023/0212690 A1 | 7/2023 | Bratman et al. |
| 2023/0287384 A1 | 9/2023 | Diniz et al. |
| 2023/0374601 A1 | 11/2023 | Lo et al. |
| 2025/0002904 A1 | 1/2025 | Bratman et al. |
| 2025/0006375 A1 | 1/2025 | Bratman et al. |

FOREIGN PATENT DOCUMENTS

| | | |
|---|---|---|
| CN | 109415763 A | 3/2019 |
| CN | 109642227 A | 4/2019 |
| CN | 111094590 A | 5/2020 |
| CN | 111154846 A | 5/2020 |
| EP | 3652741 A1 | 5/2020 |
| EP | 3704267 A1 | 9/2020 |
| EP | 4055183 A1 | 9/2022 |
| EP | 4168574 A1 | 4/2023 |
| EP | 4435118 A2 | 9/2024 |
| EP | 4444916 A1 | 10/2024 |
| EP | 4532761 A1 | 4/2025 |
| JP | 2005525084 A | 8/2005 |
| JP | 2010535513 A | 11/2010 |
| JP | 2014506788 A | 3/2014 |
| JP | 2015519084 A | 7/2015 |
| JP | 2015536639 A | 12/2015 |
| JP | 2017514499 A | 6/2017 |
| JP | 2019509068 A | 4/2019 |
| JP | 2019521315 A | 7/2019 |
| WO | WO-2012143481 A2 | 10/2012 |
| WO | WO-2014043763 A1 | 3/2014 |
| WO | WO-2015009844 A2 | 1/2015 |
| WO | WO-2016094330 A2 | 6/2016 |
| WO | WO-2016115530 A1 | 7/2016 |
| WO | WO-2017008912 A1 | 1/2017 |
| WO | WO-2017070497 A1 | 4/2017 |
| WO | WO-2017190215 A1 | 11/2017 |
| WO | WO-2018017710 A1 | 1/2018 |
| WO | WO-2019010564 A1 | 1/2019 |
| WO | WO-2019028470 A2 | 2/2019 |
| WO | WO-2019084659 A1 | 5/2019 |
| WO | WO-2019136413 A1 | 7/2019 |
| WO | WO-2020232109 A1 | 11/2020 |
| WO | WO-2021041726 A1 | 3/2021 |
| WO | WO-2021087615 A1 | 5/2021 |
| WO | WO-2021108708 A1 | 6/2021 |
| WO | WO-2021133993 A2 | 7/2021 |
| WO | WO-2021253138 A1 | 12/2021 |
| WO | WO-2023107709 A1 | 6/2023 |
| WO | WO-2023135600 A1 | 7/2023 |
| WO | WO-2023230289 A1 | 11/2023 |
| WO | WO-2024192294 A1 | 9/2024 |
| WO | WO-2024216205 A1 | 10/2024 |
| WO | WO-2025179073 A1 | 8/2025 |

OTHER PUBLICATIONS

Chen et al., Whole-Exome Enrichment with the Agilent SureSelect Human All Exon Platform Cold Spring Harbor Protocols doi: 10.1101/pdb.prot083659 (Year: 2015).*

Abbosh et al., "Phylogenetic ctDNA analysis depicts early-stage lung cancer evolution", Nature, vol. 545, Apr. 26, 2017, pp. 446-451.

Akalin et al. MethylKit: A Comprehensive R Package for the Analysis of Genome-Wide DNA Methylation Profiles. Genome Biology 13(10):R87 (2012).

Alix-Panabieres, Catherine, and Klaus Pantel. Clinical Applications of Circulating Tumor Cells and Circulating Tumor DNA as Liquid Biopsy. Cancer Discovery 6(5):479-491 (2016).

Altschul, S. et al., Basic Local Alignment Search Tool. Journal of Molecular Biology 215(3):403-410 (1990).

Amemiya, Haley M. et al. The ENCODE blacklist: Identification of problematic regions of the genome. Scientific Reports 9(1):9354, 1-5 (2019).

Amplicons 1CpG, 5CpG, and 10CpG, GC Calculator evidence :1-3 (2025).

Aravanis, Alexander M. et al. Next-Generation Sequencing of Circulating Tumor DNA for Early Cancer Detection. Cell 168(4):571-574 (2017).

Bagley, et al. Pretreatment neutrophil-to-lymphocyte ratio as a marker of outcomes in nivolumab-treated patients with advanced non-small-cell lung cancer. Lung Cancer. Apr. 2017;106:1-7. doi: 10.1016/j.lungcan.2017.01.013. Epub Jan. 25, 2017.

Bailey, Peter. et al. Genomic Analyses Identify Molecular Subtypes of Pancreatic Cancer. Nature 531(7592):47-52 (2016).

Basu, et al. Genome-wide DNA methylation profile identified a unique set of differentially methylated immune genes in oral squamous cell carcinoma patients in India. Clin Epigenetics. Feb. 3, 2017:9:13. doi: 10.1186/s13148-017-0314-x. eCollection 2017.

Beltran, et al. Divergent clonal evolution of castration resistant neuroendocrine prostate cancer. Nat Med. Mar. 2016; 22(3): 298-305. Published online Feb. 8, 2016. doi: 10.1038/nm.4045.

Bettegowda, Chetan et al. Detection of Circulating Tumor DNA in Early- and Late-Stage Human Malignancies. Science translational medicine 6(224):1-25 (2014).

Bettegowda, Chetan et al. Detection of circulating tumor DNA in early-and late-stage human malignancies. Science translational medi-cine 6(224):224ra24, 1-13 (2014).

Bewick, et al. Statistics review 13: receiver operating characteristic curves. Crit Care. Dec. 2004;8(6):508-12. Epub Nov. 4, 2004.

Blackburn et al. Use of synthetic DNA spike-in controls (sequins) for human genome sequencing. Nature Protocols 14, 2119-2151 (2019).

Borgel, et al. Targets and Dynamics of Promoter DNA Methylation During Early Mouse Development, Nature Genetics 42 (2010): 1093-1101.

Bratman et al. Potential clinical utility of ultrasensitive circulating tumor DNA detection with CAPP-Seq. Expert Review of Molecular Diagnostics. 15(6), 715-719 (2015).

Brena, et al. Toward a human epigenome. Nat Genet. Dec. 2006;38(12):1359-1360. doi: 10.1038/ng1206-1359.

Broad Institute. Adult Genotype-Tissue Expression (GTEx) Data and Resources. GTEx Portal. Retrieved from Internet on May 31, 2024. pp. 1-2. URL: https://www.gtexportal.org/home/datasets.

Bupathi et al. Biomarkers for immune therapy in colorectal cancer: mismatch-repair deficiency and others. Journal of Gastrointestinal Oncology 2016;7(5):713-720.

Burgener. et al. (2016) Utilization of methylated circulating tumour DNA in oral squamous cell carcinoma for risk stratification and detection of recurrence. TFRI—Ontario Node Research Symposium Program & Abstracts. p. 79. Accessed online: https://www.tfri.ca/docs/default-source/nodes/ontario/2016-symposiumbook.pdf.

Burgener et al. Abstract PR13: Comprehensive detection of ctDNA in localized head and neck cancer by genome- and methylome-based analysis. Clin. Cancer Res. Jun. 1, 2020. 26(11 Supple.) PR13.

Butcher, Lee M, and Stephan Beck. Nano-MeDIP-seq Methylome Analysis Using Low DNA Concentrations. Methods in molecular biology 1589:115-138 (2015).

Cao et al. Integrated epigenetic biomarkers in circulating cell-free DNA as a robust classifer for pancreatic cancer. Clinical Epigenetics (2020) 12:112; 1-14.

Cassidy, et al. Neutrophil to Lymphocyte Ratio is Associated With Outcome During Ipilimumab Treatment. EBioMedicine. Apr. 2017;18:56-61. doi: 10.1016/j.ebiom.2017.03.029. Epub Mar. 24, 2017.

Chakravarthy, et al. Human Papillomavirus Drives Tumor Devel-opment Throughout the Head and Neck: Improved Prognosis Is Associated With an Immune Response Largely Restricted to the Oropharynx. J Clin Oncol. Dec. 2016;34(34):4132-4141. doi: 10.1200/JCO.2016.68.2955. Epub Oct. 31, 2016.

Chan, K C Allen et al. Noninvasive Detection of Cancer-associated Genome-wide Hypomethylation and Copy Number Aberrations by

(56)        References Cited

OTHER PUBLICATIONS

Plasma DNA Bisulfite Sequencing. Proceedings of the National Academy of Sciences of the United States of America vol. 110,47: pp. 18761-18768 (2013).

Chen, et al. A Study of Cell-free DNA Fragmentation Pattern and Its Application in DNA Sample Type Classification. IEEE/ACM Trans Comput Biol Bioinform. Jul. 4, 2017. doi: 10.1109/TCBB.2017.2723388. Online ahead of print.

Chen, Kaifu. et al. The Overlooked Fact: Fundamental Need for Spike-In Control for Virtually All Genome-Wide Analyses. Molecular and cellular biology 36(5):662-667 (2015).

Chen, Shifu et al. Fastp: an Ultra-Fast All-in-One FASTQ Preprocessor. Bioinformatics vol. 34, 17: pp. 1884-1890 (2018).

Chiu, et al. Noninvasive prenatal diagnosis of fetal chromosomal aneuploidy by massively parallel genomic sequencing of DNA in maternal plasma. Proc Natl Acad Sci USA. Dec. 23, 2008;105(51):20458-20463. doi: 10.1073/pnas.0810641105. Epub Dec. 10, 2008.

Christensen, et al. DNA methylation, isocitrate dehydrogenase mutation, and survival in glioma. J Natl Cancer Inst. Jan. 19, 2011;103(2):143-153. doi: 10.1093/jnci/djq497. Epub Dec. 16, 2010.

CN Serial No. 2020800922328 Office Action dated Jun. 12, 2025.

Co-pending U.S. Appl. No. 18/954,991, inventors DINIZ; De Carvalho Daniel et al., filed on Nov. 21, 2024.

Co-pending U.S. Appl. No. 18/959,302, inventors DINIZ; De Carvalho Daniel et al., filed on Nov. 25, 2024.

Co-pending U.S. Appl. No. 19/028,028, inventors Diniz De Carvalho; Daniel et al., filed on Jan. 17, 2025.

Dai, et al. Identification of hub methylated-CpG sites and associated genes in oral squamous cell carcinoma. Cancer Med. May 2020; 9(9): 3174-3187. Published online Mar. 10, 2020. doi: 10.1002/cam4.2969.

Daniels et al. New Map of Bacteriophase Lambda DNA. Journal of Virology, Jan. 1980, p. 390-400.

De Carvalho D. Real-time liquid biopsy cancer diagnosis and monitoring. Flintbox. May 16, 2017; Available at URL: https://www.flintbox.com/public/project/31470 pp. 1.

Deininger, Prescott. Alu Elements: Know the SINEs. Genome Biology 12(12):236, 1-21 (2011).

Deveson et al., Representing genetic variation with synthetic DNA standards. Nature Methods 13: 784-791 (2016).

Di Giacomo, et al. Long-term survival and immunological parameters in metastatic melanoma patients who responded to ipilimumab 10 mg/kg within an expanded access programme. Cancer Immunol Immunother. Jun. 2013;62(6):1021-1028. doi: 10.1007/s00262-013-1418-6. Epub Apr. 17, 2013.

Diaz Jr, Luis A, and Alberto Bardelli. Liquid biopsies: genotyping circulating tumor DNA. Journal of clinical oncology 32(6):579-586 (2014).

Eckhardt, Florian, et al., DNA Methylation Profiling of Human Chromosomes 6, 20 and 22. Nature Genetics 38(12): 1378-1385 (2006).

Encode. Experiment summary for ENCSR000DFS. Stanford University. Date released: Sep. 30, 2011. 2 pages. doi:10.17989/ENCSR000DFS.

EP18874092.2 Extended European Search Report dated Jul. 5, 2021.

EP20240176389.5 Extended European Search Report dated Nov. 19, 2024.

EP20884272.4 Extended European Search Report dated Nov. 7, 2023.

EP21825516.4 European Search Report and Opinion dated Jan. 25, 2024.

EP24177800 Extended European Search Report dated Dec. 16, 2024.

Esteller, et al. Inactivation of the DNA-repair gene MGMT and the clinical response of gliomas to alkylating agents. N Engl J Med. Nov. 9, 2000;343(19):1350-1354. doi: 10.1056/NEJM200011093431901.

European search report and opinion dated Mar. 23, 2021 for EP Application No. 18832886.8.

European search report and opinion dated Oct. 31, 2019 for EP Application No. 17792306.7.

Ewing, et al. Base-Calling of Automated Sequencer Traces Using Phred. II. Error probabilities. Genome Research. 1998;8:186-194.

Fan et al., Noninvasive diagnosis of fetal aneuploidy by shotgun sequencing DNA from maternal blood. Proc Natl Acad Sci U S A :105(42):16266-71 (2008).

Fang, et al. Breast cancer methylomes establish an epigenomic foundation for metastasis. Sci Transl Med. Mar. 23, 2011;3(75):75ra25. doi: 10.1126/scitranslmed.3001875.

Feber, et al. Comparative methylome analysis of benign and malignant peripheral nerve sheath tumors. Genome Res. Apr. 2011; 21(4): 515-524. doi: 10.1101/gr.109678.110.

Ferrucci, et al. Baseline neutrophils and derived neutrophil-to-lymphocyte ratio: prognostic relevance in metastatic melanoma patients receiving ipilimumab. Ann Oncol. Apr. 2016;27(4):732-738. doi: 10.1093/annonc/mdw016. Epub Jan. 22, 2016.

Flach, Peter. et al. A Coherent Interpretation of AUC as a Measure of Aggregated Classification Performance. Proceedings of the 28th International Conference on Machine Learning: 1-8 (2011).

Fleischhacker, M et al. Circulating Nucleic Acids (CNAs) and Cancer—a Survey. Biochimica et Biophysica Acta vol. 1775,1: pp. 181-232 (2007).

Flusberg, Benjamin A, et al., Direct Detection of DNA Methylation During Single-molecule, Real-time Sequencing. Nature Methods vol. 7,6: pp. 461-465 (2010).

Fraga, et al. The affinity of different MBD proteins for a specific methylated locus depends on their intrinsic binding properties. Nucleic Acids Res. Mar. 15, 2003;31(6):1765-1774. doi: 10.1093/nar/gkg249.

Galardi et al., Cell-free DNA-methylation-based methods and applications in oncology. Biomolecules. 10(12):1677 (2020).

Gao, et al. miR-615-5p is epigenetically inactivated and functions as a tumor suppressor in pancreatic ductal adenocarcinoma. Oncogene. Mar. 2, 2015;34(13):1629-1640. doi: 10.1038/onc.2014.101. Epub Apr. 28, 2014.

Gevaert, et al. Pancancer analysis of DNA methylation-driven genes using MethylMix. Genome Biol. Jan. 29, 2015;16(1):17. doi: 10.1186/s13059-014-0579-8.

Gonzalgo, et al. Identification and characterization of differentially methylated regions of genomic DNA by methylation-sensitive arbitrarily primed PCR. Cancer Res. Feb. 15, 1997;57(4):594-599.

Gosho, et al. Study Designs and Statistical Analyses for Biomarker Research. Sensors (Basel). 2012; 12(7): 8966-8986. Published online Jun. 29, 2012. doi: 10.3390/s120708966.

Graves, et al. Quantitative and qualitative analysis of [(18)F]FDG and [(18)F]FAZA positron emission tomography of head and neck cancers and associations with HPV status and treatment outcome. Eur J Nucl Med Mol Imaging. Apr. 2016;43(4):617-625. doi: 10.1007/s00259-015-3247-7. Epub Nov. 18, 2015.

GTEx Consortium. Human genomics. The Genotype-Tissue Expression (GTEx) pilot analysis: multitissue gene regulation in humans. Science. May 8, 2015;348(6235):648-660. doi: 10.1126/science.1262110. Epub May 7, 2015.

Gu, et al. Preparation of reduced representation bisulfite sequencing libraries for genome-scale DNA methylation profiling. Nat Protoc. Apr. 2011;6(4):468-81. doi: 10.1038/nprot.2010.190. Epub Mar. 18, 2011.

Hegi et al., MGMT Gene Silencing and Benefit from Temozolomide in Glioblastoma. The New England Journal of Medicine 352(10): 997-1003 (2005).

Heinz, et al. Simple combinations of lineage-determining transcription factors prime cis-regulatory elements required for macrophage and B cell identities. Mol Cell. May 28, 2010;38(4):576-589. doi: 10.1016/j.molcel.2010.05.004.

Heyn, et al. DNA methylation profiling in the clinic: applications and challenges. Nature Reviews Genetics 13(10):679-692 (2012).

Hinoue, et al. Genome-scale analysis of aberrant DNA methylation in colorectal cancer. Genome Res. Feb. 2012;22(2):271-282. doi: 10.1101/gr.117523.110. Epub Jun. 9, 2011.

(56)          References Cited

OTHER PUBLICATIONS

Hoadley, et al. Multiplatform analysis of 12 cancer types reveals molecular classification within and across tissues of origin. Cell. Aug. 14, 2014;158(4):929-944. doi: 10.1016/j.cell.2014.06.049. Epub Aug. 7, 2014.

Holm, S. A Simple Sequentially Rejective Multiple Test Procedure. Scand J. Statist 6: 65-70, 1979.

Houseman, et al. Reference-free deconvolution of DNA methylation data and mediation by cell composition effects. BMC Bioinformatics. Jun. 29, 2016;17:259. doi: 10.1186/s12859-016-1140-4.

Hu, et al. DNA methylation presents distinct binding sites for human transcription factors. Elife. Sep. 3, 2013;2:e00726. doi: 10.7554/eLife.00726.

Huang, et al. Cell-Free DNA Methylation Profiling Analysis-Technologies and Bioinformatics. Cancers (Basel). Nov. 6, 2019;11(11):1741. doi: 10.3390/cancers11111741.

Hughey et al. Robust meta-analysis of gene expression using the elastic net. Nucleic Acids Research 2015, vol. 43, No. 12, e79, 11 pages.

Hung, et al. Detection of circulating fetal nucleic acids: a review of methods and applications. J Clin Pathol. Apr. 2009;62(4):308-313. doi: 10.1136/jcp.2007.048470.

International search report with written opinion dated Feb. 14, 2019 for PCT/CA2018/000203.

International search report with written opinion dated Jun. 28, 2017 for PCT/CA2017/000108.

International search report with written opinion dated Oct. 3, 2018 for PCT/CA2018/000141.

International search report with written opinion dated Oct. 5, 2021 for PCT/CA2021/050842.

Ji, Yinqiu. et al. SPIKEPIPE: A metagenomic pipeline for the accurate quantification of eukaryotic species occurrences and intraspecific abundance change using DNA barcodes or mitogenomes. BioRxiv :1-59 (2019).

Jiang et al., Synthetic spike-in standards for RNA-seq experiments. Genome Res. 21(9):1543-1551 (2011).

Jiang, Lichun et al. Synthetic spike-in standards for RNA-seq experiments. Genome research 21(9):1543-1551 (2011).

Juppner, H. Functional properties of the PTH/PTHrP receptor. Bone 17(2 Suppl):S39-S42 (1995).

Kalinich et al., An RNA-based signature enables high specificity detection of circulating tumor cells in hepatocellular carcinoma. Proc Natl Acad Sci USA.114(5):1123-1128 (2017).

Kandoth et al. Mutational landscape and significance across 12 major cancer types. Nature 502(7471):333-339 (2013).

Karimzadeh et al. Umap and Bismap: quantifying genome and methylome mappability. Nucleic Acids Research, 2018, vol. 46, No. 20, e120. 13 pages.

Karolchik, Donna, et al., The UCSC Table Browser Data Retrieval Tool. Nucleic Acids Research 32:D493-D496 (2004).

Keravnou, Anna. et al. MeDIP combined with in-solution targeted enrichment followed by NGS: Inter-individual methylation variability of fetal-specific biomarkers and their implementation in a proof of concept study for NIPT. Plos one 13(6):e0199010, 1-13 (2018).

Keravnou, Anna. et al. Whole-genome fetal and maternal DNA methylation analysis using MeDIP-NGS for the identification of differentially methylated regions. Genetics research 98:e15, 1-9 (2016).

Kirkwood, et al. Immunotherapy of cancer in 2012. CA Cancer J Clin. Sep.-Oct. 2012;62(5):309-35. doi: 10.3322/caac.20132. Epub May 10, 2012.

Koestler, et al. DNA Methylation-Derived Neutrophil-to-Lymphocyte Ratio: An Epigenetic Tool to Explore Cancer Inflammation and Outcomes. Cancer Epidemiol Biomarkers Prev. Mar. 2017;26(3):328-338. doi: 10.1158/1055-9965.EPI-16-0461. Epub Dec. 13, 2016.

Krueger, et al. Bismark: a flexible aligner and methylation caller for Bisulfite-Seq applications. Bioinformatics. Jun. 1, 2011;27(11):1571-2. doi: 10.1093/bioinformatics/btr167. Epub Apr. 14, 2011.

Kuzman, et al. Neutrophil-lymphocyte ratio as a predictive biomarker for response to high dose interleukin-2 in patients with renal cell carcinoma. BMC Urol. Jan. 5, 2017;17(1):1. doi: 10.1186/s12894-016-0192-0.

Langmead, Ben et al. Fast gapped-read alignment with Bowtie 2. Nature methods 9(4):357-359 (2012).

Lasseter et al. Plasma cell-free DNA variant analysis compared with methylated DNA analysis in renal cell carcinoma. Genetics in Medicine, vol. 22, No. 8, Aug. 2020, p. 1366-1373.

Law, et al. voom: precision weights unlock linear model analysis tools for RNA-seq read counts. Genome Biol (2014) 15, R29. https://doi.org/10.1186/GB-2014-15-2-r29 (17 pages).

Lee, et al. Strategy of Using Intratreatment Hypoxia Imaging to Selectively and Safely Guide Radiation Dose De-escalation Concurrent With Chemotherapy for Locoregionally Advanced Human Papillomavirus-Related Oropharyngeal Carcinoma. Int J Radiat Oncol Biol Phys. Sep. 1, 2016;96(1):9-17. doi: 10.1016/j.ijrobp.2016.04.027. Epub May 7, 2016.

Legendre, et al. Whole-genome bisulfite sequencing of cell-free DNA identifies signature associated with metastatic breast cancer. Clin Epigenet (2015). 7:100. https://doi.org/10.1186/s13148-015-0135-8 (10 pages).

Lehmann-Werman, et al. Identification of tissue-specific cell death using methylation patterns of circulating DNA. Proc Natl Acad Sci USA 2016;113:E1826-34.

Leontiou, et al. Bisulfite Conversion of DNA: Performance Comparison of Different Kits and Methylation Quantitation of Epigenetic Biomarkers that Have the Potential to Be Used in Non-Invasive Prenatal Testing. PLoS One. Aug. 6, 2015;10(8):e0135058. doi: 10.1371/journal.pone.0135058. eCollection 2015.

Liang, Wenhua. et al. Non-invasive diagnosis of early-stage lung cancer using high-throughput targeted DNA methylation sequencing of circulating tumor DNA (ctDNA). Theranostics 9(7):2056-2070 (2019).

Lienhard, et al. MEDIPS: genome-wide differential coverage analysis of sequencing data derived from DNA enrichment experiments. Bioinformatics. Jan. 15, 2014;30(2):284-286. doi: 10.1093/bioinformatics/btt650. Epub Nov. 13, 2013.

Lienhard et al. QSEA—modelling of genome-wide DNA methylation from sequencing enrichment experiments. Nucleic Acids Research, 2017, vol. 45, No. 6, e44. 13 pages.

Liggett, Thomas. et al. Differential methylation of cell-free circulating DNA among patients with pancreatic cancer versus chronic pancreatitis. Cancer 116(7):1674-1680 (2010).

Lisanti, et al. Standardization and quality controls for the methylated DNA immunoprecipitation technique. Epigenetics. Jun. 1, 2012;7(6):615-625. doi: 10.4161/epi.20028. Epub Jun. 1, 2012.

Liu, Bo. et al. Cloud-based Bioinformatics Workflow Platform for Large-scale Next-generation Sequencing Analyses. Journal of Biomedical Informatics 49:119-133 (2014).

Liu, Jianfang et al. An Integrated TCGA Pan-Cancer Clinical Data Resource to Drive High-Quality Survival Outcome Analytics. Cell. Apr. 5, 2018;173(2):400-416.e11. doi: 10.1016/j.cell.2018.02.052.

Ito, et al. Role of Tet Proteins in 5mC to 5hmC Conversion, ES Cell Self-Renewal, and ICM Specification. Nature 466 (2010): 1129-1133.

Lui, Yanni Y N et al. Predominant Hematopoietic Origin of Cell-free DNA in Plasma and Serum After Sex-mismatched Bone Marrow Transplantation. Clinical Chemistry vol. 48,3: pp. 421-427 (2002).

Mack, et al. Epigenomic alterations define lethal CIMP-positive ependymomas of infancy. Nature. Feb. 27, 2014;506(7489):445-450. doi: 10.1038/nature13108. Epub Feb. 19, 2014.

Martincorena et al. Tumor evolution. High burden and pervasive positive selection of somatic mutations in normal human skin. Science 348(6237):880-6 (May 22, 2015).

Mazurek, Agnieszka M. et al. Assessment of the total cfDNA and HPV16/18 detection in plasma samples of head and neck squamous cell carcinoma patients, Oral Oncology 54:36-41 (2016).

Mcgranahan, et al. Clonal status of actionable driver events and the timing of mutational processes in cancer evolution. Sci Transl Med. Apr. 15, 2015;7(283):283ra54. doi: 10.1126/scitranslmed.aaa1408. (22 pages).

(56) References Cited

OTHER PUBLICATIONS

Menden, et al. Machine learning prediction of cancer cell sensitivity to drugs based on genomic and chemical properties. PLoS One. Apr. 30, 2013;8(4):e61318. doi: 10.1371/journal.pone.0061318. Print 2013.

Michot et al., "Immune-Related Adverse Events With Immune Checkpoint Blockade: A Comprehensive Review," European Journal of Cancer 54:139-148 (Feb. 2016) (Epublished on Jan. 5, 2016) DOI: 10.1016/j.ejca.2015.11.016.

Mikeska, et al. DNA methylation biomarkers: cancer and beyond. Genes (Basel). Sep. 16, 2014;5(3):821-864. doi: 10.3390/genes5030821.

Moore, Lisa D. et al. DNA methylation and its basic function. Neuropsychopharmacology 38(1):23-38 (2013).

Mouliere et al. Enhanced Detection of Circulating Tumor DNA by Fragment Size Analysis. Science Translational Medicine 10(466):eaat4921 (2018).

Muhanna et al. Cell-Free DNA Kinetics in a Pre-Clinical Model of Head and Neck Cancer. Scientific Reports 2017 7: 16723. p. 1-11.

Narkhede, Sarang. Understanding AUC-ROC Curve. Towards Data Science, Jun. 26, 2018; [retrieved on Aug. 10, 2019]. Available at URL:https://towardsdatascience.com/understanding-auc-roc-curve-68b2303cc9c5. pp. 1-6.

Nassiri et al. Detection and discrimination of intracranial tumors using plasma cell-free DNA methylomes. Nat. Med. 2020; 26(7): 1044-1047.

NCBI. GEO accession GSM1465024. HCT116 whole genome bisulfite sequence. Public on Sep. 10, 2014. Last update May 15, 2019. 2 pages. URL: https://www.ncbi.nlm.nih.gov/geo/query/acc.cgi?acc=GSM1465024.

Neary, et al. Comparative analysis of MBD-seq and MeDIP-seq and estimation of gene expression changes in a rodent model of schizophrenia. Genomics. Jul. 2017;109(3-4):204-213. doi: 10.1016/j.ygeno.2017.03.004. Epub Mar. 29, 2017.

Newman, Aaron M. et al. An Ultrasensitive Method for Quantitating Circulating Tumor DNA With Broad Patient Coverage. Nature Medicine 20(5):548-554 (2014).

Newman, Aaron M. et al. Integrated Digital Error Suppression for Improved Detection of Circulating Tumor DNA. Nature Biotechnology 34(5):547-555 (2016).

NIH Guidelines for Research Involving Recombinant or Synthetic Nucleic Acid Molecules :1-149 (2019).

Northwestern University. Oligo Calc: Oligonucleotide Properties Calculator. Retrieved from the internet: http://biotools.nubic.northwestern.edu/OligoCalc.html (Year: 2022).

Notice of Allowance dated Mar. 19, 2021 for U.S. Appl. No. 16/098,620.

Notice of Allowance dated Aug. 31, 2022 for U.S. Appl. No. 17/519,350.

Notice of Allowance dated Sep. 15, 2022 for U.S. Appl. No. 17/519,350.

Nuzzo et al., Detection of renal cell carcinoma using plasma and urine cell-free DNA methylomes. Nat Med. 26(7):1041-1043 (2020).

Office action dated Jan. 28, 2022 for U.S. Appl. No. 17/519,350.

Office action dated Mar. 23, 2023 for U.S. Appl. No. 16/760,522.

Office action dated Apr. 26, 2023 for U.S. Appl. No. 16/630,299.

Office action dated May 11, 2022 for U.S. Appl. No. 16/630,299.

Office action dated Jun. 1, 2022 for U.S. Appl. No. 17/519,350.

Office action dated Jun. 25, 2020 for U.S. Appl. No. 16/098,620.

Office action dated Jun. 29, 2022 for U.S. Appl. No. 17/668,314.

Office action dated Jul. 19, 2023 for U.S. Appl. No. 18/061,273.

Office action dated Aug. 31, 2021 for U.S. Appl. No. 16/630,299.

Office action dated Oct. 6, 2023 for U.S. Appl. No. 16/760,522.

Office action dated Nov. 30, 2023 for U.S. Appl. No. 18/061,273.

Office action dated Dec. 6, 2023 for U.S. Appl. No. 16/630,299.

Office action dated Dec. 21, 2020 for U.S. Appl. No. 16/098,620.

Orlando et al. Quantitative ChIP-Seq Normalization Reveals Global Modulation of the Epigenome. Cell Reports 9, 2014, 1163-1170.

Owczarzy et al. IDT SciTools: a suite for analysis and design of nucleic acid oligomers. Nucleic Acids Research, 2008, vol. 36, W163-W169.

PCT/CA2017/000108 International Preliminary Report on Patentability dated Nov. 6, 2018.

PCT/CA2018/000141 International Preliminary Report on Patentability dated Jan. 14, 2020.

PCT/CA2018/000203 International Preliminary Report on Patentability dated May 5, 2020.

PCT/CA2020/051507 International Preliminary Report on Patentability dated May 10, 2022.

PCT/CA2020/051507 International Search Report and Written Opinion dated Jan. 11, 2021.

PCT/CA2021/050842 International Preliminary Report on Patentability dated Dec. 13, 2022.

PCT/US2022/052432 International Search Report and Written Opinion dated Mar. 21, 2023.

PCT/US2023/023625 International Preliminary Report on Patentability dated Dec. 5, 2024.

PCT/US2023/023625 International Search Report and Written Opinion dated Aug. 9, 2023.

PCT/US2024/020012 International Search Report and Written Opinion dated May 22, 2024.

PCT/US2024/024491 International Search Report and Written Opinion dated Jul. 5, 2024.

PCT/US2025/016672 International Search Report and Written Opinion dated Jun. 6, 2025.

Ponty et al. GenRGenS: software for generating random genomic sequences and structures. Bioinformatics, vol. 22, No. 12, 2006, pp. 1534-1535.

Potter et al., Validation of a real-time PCR-based qualitative assay for the detection of methylated SEPT9 Dna in human plasma. Clin Chem. 60(9):1183-1191 (2014).

QIAGEN®: QIAamp® Circulating Nucleic Acid Handbook. 64 pages, (2019).

Quinlan, Aaron R, and Ira M. Hall. BEDTools: a flexible suite of utilities for comparing genomic features. Bioinformatics 26(6):841-842 (2010).

R Core Team (2021). R: A language and environment for statistical computing. R Foundation for Statistical Computing, Vienna, Austria. URL: https://www.R-project.org/. Copy of homepage provided (3 pages); obtained online on Sep. 11, 2023.

Rahmani, et al. BayesCCE: a Bayesian framework for estimating cell-type composition from DNA methylation without the need for methylation reference. Genome Biol 19, 141 (2018). https://doi.org/10.1186/s13059-018-1513-2 (18 pages).

Rauch, et al. MIRA-assisted microarray analysis, a new technology for the determination of DNA methylation patterns, identifies frequent methylation of homeodomain-containing genes in lung cancer cells. Cancer Res. Aug. 15, 2006;66(16):7939-7947. doi: 10.1158/0008-5472.CAN-06-1888.

Re, A.C.D. compute.es: Compute Effect Sizes (2022).

ReGEO. GSE Accession GSE89473. DNA methylation patterns in twins discordant for ALS reveal concordant signatures of disease [RRBS]. Submission Date Nov. 2, 2016. Last Update Mar. 14, 2017. 1 page. URL: https://regeo.org:8443/details.jsp?gseld=GSE89473.

Rodríguez-Paredes, et al. Cancer epigenetics reaches mainstream oncology. Nat Med. Mar. 2011;17(3):330-339. doi: 10.1038/nm.2305.

Ruan, et al. Role of hypoxia in the hallmarks of human cancer. J Cell Biochem. Aug. 15, 2009;107(6):1053-1062. doi: 10.1002/jcb.22214.

Sanders, Alison et al. Cadmium exposure and the epigenome: Exposure-associated patterns of DNA methylation in leukocytes from mother-baby pairs. Epigenetics, 9(2), 212-221. Published online: Oct. 28, 2013. https://doi.org/10.4161/epi.26798.

Santos et al. Prognostic value of FLT3 mutations among different cytogenetic subgroups in acute myeloid leukemia. JNCI 117(10): 2145-2155. Year: 2011.

Saxonov S, et al. A genome-wide analysis of CpG dinucleotides in the human genome distinguishes two distinct classes of promoters. Proc Natl Acad Sci U S A. Jan. 31, 2006;103(5):1412-7. Epub Jan. 23, 2006.

(56)        References Cited

OTHER PUBLICATIONS

Schatz et al. Cloud computing and the DNA data race. Nature Biotechnology, vol. 28, No. 7, Jul. 2010. p. 691-693.

Schneider, Valerie A. et al. Evaluation of GRCh38 and De Novo Haploid Genome Assemblies Demonstrates the Enduring Quality of the Reference Assembly. Genome Research 27(5):849-864 (2017).

Schwarzenbach, Heidi. et al. Cell-free nucleic acids as biomarkers in cancer patients. Nature Reviews Cancer 11(6):426-437 (2011).

Shamay, et al. CpG methylation as a tool to characterize cell-free Kaposi sarcoma herpesvirus DNA. J Infect Dis. Apr. 1, 2012;205(7):1095-1099. doi: 10.1093/infdis/jis032. Epub Feb. 22, 2012.

Sharma, et al. Epigenetics in cancer. Carcinogenesis. Jan. 2010; 31(1): 27-36. Published online Sep. 13, 2009. doi: 10.1093/carcin/bgp220.

Shen, et al. Sensitive tumour detection and classification using plasma cell-free DNA methylomes. Nature. Nov. 2018; 563(7732): 579-583. doi: 10.1038/s41586-018-0703-0. Epub Nov. 14, 2018.

Shen, Shu Yi et al. Preparation of cfMeDIP-seq libraries for methylome profiling of plasma cell-free DNA. Nature Protocols 14(10):2749-2780 (2019).

Shen, Shu Yi et al. Sensitive Tumour Detection and Classification Using Plasma cell-free DNA Methylomes. Nature 563(7732):579-583(2018).

Simpson, Jared T. et al. Detecting DNA Cytosine Methylation Using Nanopore Sequencing. Nature methods 14(4):407-410 (2017).

Snyder, et al. Cell-free DNA comprises an in vivo nucleosome footprint that informs its tissues-of-origin. Cell 164(1-2):57-68 (2016).

Snyder, Thomas M et al. Universal Noninvasive Detection of Solid Organ Transplant Rejection. Proceedings of the National Academy of Sciences of the United States of America vol. 108, 15: pp. 6229-6234 (2011).

Song et al. Potential functional roles of DNA demethylation intermediates. Trends Biochem Sci Oct. 2013; 38(10): 480-484.

Staunstrup, et al. Genome-wide DNA methylation profiling with MeDIP-seq using archived dried blood spots. Clin Epigenetics. Jul. 26, 2016;8:81. doi: 10.1186/s13148-016-0242-1. eCollection 2016.

Steinmann, et al. Frequent promoter hypermethylation of tumor-related genes in head and neck squamous cell carcinoma. Oncol Rep. Dec. 2009;22(6):1519-26. doi: 10.3892/or_00000596.

Stevens, Michael. et al. Estimating Absolute Methylation Levels at Single-CpG Resolution From Methylation Enrichment and Restriction Enzyme Sequencing Methods. Genome Research 23(9):1541-1553 (2013).

Stirzaker et al: "Methylome sequencing in triple-negative breast cancer reveals distinct methylation clusters with prognostic value", Nature Communications, vol. 6, No. 5899, Jan. 1, 2015 (Jan. 1, 2015), XP055418632, GB ISSN: 2041-1723, DOI: 10.1038/ncomms6899.

Stransky, Nicolas. et al. The Mutational Landscape of Head and Neck Squamous Cell Carcinoma. Science 333(6046):1157-1160 (2011).

Strichman-Almashanu et al. A Genome-Wide Screen for Normally Methylated Human CpG Islands That Can Identify Novel Imprinted Genes. Genome Research 12:543-554. 2002.

Sturm, et al. Hotspot mutations in H3F3A and IDH1 define distinct epigenetic and biological subgroups of glioblastoma. Cancer Cell. Oct. 16, 2012;22(4):425-437. doi: 10.1016/j.ccr.2012.08.024.

Stutheit-Zhao, Eric Y. et al. Early Changes in Tumor-Naive Cell-Free Methylomes and Fragmentomes Predict Outcomes in Pembrolizumab-Treated Solid Tumors. Cancer Discov. Feb. 22, 2024;14(6):1048-1063. doi: 10.1158/2159-8290.CD-23-1060.

Su, Andrew I. et al. A gene atlas of the mouse and human protein-encoding transcriptomes. Proceedings of the National Academy of Sciences 101(16):6062-6067 (2004).

Sun et al., Plasma DNA tissue mapping by genome-wide methylation sequencing for noninvasive prenatal, cancer, and transplantation assessments. Proc Natl Acad Sci USA. 112(40): E5503-E5512 (2015).

Taiwo, Oluwatosin. et al. Methylome Analysis Using MeDIP-seq With Low DNA Concentrations. Nature protocols 7(4):617-636 (2012).

Tarailo-Graovac, et al. Using RepeatMasker to identify repetitive elements in genomic sequences. Curr Protoc Bioinformatics. Mar. 2009; Chapter 4:Unit 4.10. doi: 10.1002/0471250953.bi0410s25.

Templeton, et al. Prognostic role of neutrophil-to-lymphocyte ratio in solid tumors: a systematic review and meta-analysis. J Natl Cancer Inst. May 29, 2014;106(6):dju124. doi: 10.1093/jnci/dju124. Print Jun. 2014.

Teschendorff, et al. A comparison of reference-based algorithms for correcting cell-type heterogeneity in Epigenome-Wide Association Studies. BMC Bioinformatics. Feb. 13, 2017;18(1):105. doi: 10.1186/s12859-017-1511-5.

TFCheckpoint. Transcription Factor checkpoint 2.0. Website. Retrieved online Feb. 21, 2025. 6 pages. URL: https://www.tfcheckpoint.org/.

The Cancer Genome Atlas Network. Comprehensive genomic characterization of head and neck squamous cell carcinomas. Nature 517:576-582 (2015a).

The Cancer Genome Atlas Program (TCGA). National Cancer Institute. Available at URL: https://www.cancer.gov/ccg/research/genome-sequencing/tcga pp. 1-4 (2022).

Thienpont, et al. Tumor hypoxia causes DNA hypermethylation by reducing TET activity. Nature. Sep. 1, 2016; 537(7618): 63-68. Published online Aug. 17, 2016. doi: 10.1038/nature19081.

Thierry, Alain R. et al. Origins, structures, and functions of circulating DNA in oncology. Cancer and metastasis reviews 35:347-376 (2016).

Titus, et al. Cell-type deconvolution from DNA methylation: a review of recent applications. Hum Mol Genet. Oct. 1, 2017;26(R2):R216-R224. doi: 10.1093/hmg/ddx275.

Toustrup, et al. Gene expression classifier predicts for hypoxic modification of radiotherapy with nimorazole in squamous cell carcinomas of the head and neck. Radiother Oncol. Jan. 2012;102(1):122-129. doi: 10.1016/j.radonc.2011.09.010. Epub Oct. 11, 2011.

Travis, W.D. Pathology of lung cancer, Clin Chest Med., Dec. 2011;32(4):669-92. doi:10.1016/j.ccm.2011.08.005. PMID: 22054879.

Underhill, Hunter R. et al. Fragment length of circulating tumor DNA. PLoS genetics 12(7):e1006162, 1-24 (2016).

U.S. Appl. No. 16/630,299 Notice of Allowance dated Feb. 26, 2024.

U.S. Appl. No. 16/760,522 Corrected Notice of Allowability dated Jun. 10, 2025.

U.S. Appl. No. 16/760,522 Notice of Allowance dated Jun. 2, 2025.

U.S. Appl. No. 16/760,522 Office Action dated Sep. 20, 2024.

U.S. Appl. No. 17/353,756 Office Action dated Aug. 22, 2024.

U.S. Appl. No. 17/353,756 Office Action dated May 28, 2025.

U.S. Appl. No. 17/736,570 Office Action dated Feb. 19, 2025.

U.S. Appl. No. 18/061,273 Corrected Notice of Allowability dated Jan. 16, 2025.

U.S. Appl. No. 18/061,273 Notice of Allowance dated Aug. 27, 2024.

U.S. Appl. No. 18/067,661 Office Action dated May 8, 2024.

U.S. Appl. No. 18/067,661 Office Action dated Nov. 22, 2024.

U.S. Appl. No. 18/820,166 Office Action dated Apr. 8, 2025.

Van De Voorde, et al. DNA methylation-based biomarkers in serum of patients with breast cancer. Mutat Res. Oct.-Dec. 2012;751(2):304-325. doi: 10.1016/j.mrrev.2012.06.001. Epub Jun. 12, 2012.

Van Der Maaten, et al. Visualizing Data using t-SNE. Journal of Machine Learning Research 9 (2008) pp. 2579-2605.

Vandeweyer, Geert et al. VariantDB: A Flexible Annotation and Filtering Portal for Next Generation Sequencing Data. Genome Medicine 6(10):74, 1-10 (2014).

Varley, et al. Dynamic DNA methylation across diverse human cell lines and tissues. Genome Res. Mar. 2013;23(3):555-567. doi: 10.1101/gr.147942.112. Epub Jan. 16, 2013.

Visvanathan, et al. Monitoring of Serum DNA Methylation as an Early Independent Marker of Response and Survival in Metastatic Breast Cancer: TBCRC 005 Prospective Biomarker Study. J Clin Oncol. Mar. 2017;35(7):751-758. doi: 10.1200/JCO.2015.66.2080. Epub Nov. 21, 2016.

(56)        References Cited

OTHER PUBLICATIONS

Wang et al. DNA methylation signatures in circulating cell-free DNA as biomarkers for the early detection of cancer. Science China. 2017, vol. 60, No. 4: 356-362.

Wang et al. High efficiency error suppression for accurate detection of low-frequency variants. Nucleic Acids Research 2019, vol. 47, No. 15, e87. 11 pages.

Wang, Yong, and Frederick C.C. Leung. An Evaluation of New Criteria for CpG Islands in the Human Genome as Gene Markers. Bioinformatics 20(7):1170-1177 (2004).

Wang, Zheng. et al. MGMT promoter methylation in serum and cerebrospinal fluid as a tumor-specific biomarker of glioma. Biomedical reports 3(4):543-548 (2015).

Warton, et al. Methylated circulating tumor DNA in blood: power in cancer prognosis and response. Endocr Relat Cancer. Mar. 2016;23(3):R157-R171. doi: 10.1530/ERC-15-0369. Epub Jan. 13, 2016.

Warton, et al. Methylation of cell-free circulating DNA in the diagnosis of cancer. Front Mol Biosci. Apr. 22, 2015;2:13. doi: 10.3389/fmolb.2015.00013. eCollection 2015.

Weisenberger, D. Characterizing DNA methylation alterations from The Cancer Genome Atlas. J Clin Invest. Jan. 2014;124(1):17-23. doi: 10.1172/JCI69740. Epub Jan. 2, 2014.

Wen, Lu. et al. Genome-scale detection of hypermethylated CpG islands in circulating cell-free DNA of hepatocellular carcinoma patients. Cell research 25(11):1250-1264 (2015).

Wiencke, et al. Immunomethylomic approach to explore the blood neutrophil lymphocyte ratio (NLR) in glioma survival. Clin Epigenetics. Feb. 2, 2017;9:10. doi: 10.1186/s13148-017-0316-8. eCollection 2017.

Wong, Karen et al. Point-of-care outcome assessment in the cancer clinic: Audit of data quality. Radiotherapy and Oncology. vol. 95, Issue 3, Jun. 2010, pp. 339-343.

Wu et al. A novel cell-free DNA methylation-based model improves the early detection of colorectal cancer. Molecular Oncology 15 (2021) 2702-2714.

Wu, et al. BioGPS: building your own mash-up of gene annotations and expression profiles. Nucleic Acids Res. Jan. 4, 2016;44(D1):D313-316. doi: 10.1093/nar/gkv1104. Epub Nov. 17, 2015.

Wu, et al. Genome-wide Analysis of 5-Hydroxymethylcytosine Distribution Reveals its Dual Function in Transcriptional Regulation in Mouse Embryonic Stem Cells. Genes & Development 25 (2011): 679-684.

Wu, Xiwei. et al. CpG island hypermethylation in human astrocytomas. Cancer research 70(7):2718-2727 (2010). With supplementary Information.

Xia, et al. Recent advances in hypoxia-inducible factor (HIF)-1 inhibitors. Eur J Med Chem. Mar. 2012;49:24-40. doi: 10.1016/j.ejmech.2012.01.033. Epub Jan. 24, 2012.

Xiang, Yuqian. et al. DNA methylome profiling of maternal peripheral blood and placentas reveal potential fetal DNA markers for non-invasive prenatal testing. Molecular human reproduction 20(9):875-884 (2014).

Xu et al. Secondary structure prediction of single sequences using RNA structure. RNA Structure Determination. Springer, 2016, pp. 15-34.

Yagi, et al. DNA methylation profile of tissue-dependent and differentially methylated regions (T-DMRs) in mouse promoter regions demonstrating tissue-specific gene expression. Genome Res. Dec. 2008;18(12):1969-1978. doi: 10.1101/gr.074070.107. Epub Oct. 29, 2008.

Zauber, et al. KRAS gene mutations are more common in colorectal villous adenomas and in situ carcinomas than in carcinomas. Int J Mol Epidemiol Genet. 2013;4(1):1-10. Epub Mar. 18, 2013.

Zhang, Lin et al. Cancer progression prediction using gene inter-action regularized elastic net. IEEE/ACM transactions on computational biology and bioinformatics 14(1):145-154 (2015)..

Zhao, Ming-Tao. et al. Methylated DNA immunoprecipitation and high-throughput sequencing (MeDIP-seq) using low amounts of genomic DNA. Cellular reprogramming 16(3):175-184 (2014).

Zhou et al. Alterations of biomarker profiles after neoadjuvant chemotherapy in breast cancer: tumor heterogeneity should be taken into consideration. Oncotarget 6(34): 36894-36902. 2015.

Zhou et al. SeSAMe: reducing artifactual detection of DNA methylation by Infinium BeadChips in genomic deletions. Nucleic Acids Research, 2018, vol. 46, No. 20. e123. 15 pages.

Zou, et al. Epigenome-wide association studies without the need for cell-type composition. Nat Methods. Mar. 2014;11(3):309-11. doi: 10.1038/nmeth.2815. Epub Jan. 26, 2014.

Zymo Research. 5-Methylcytosine & 5-Hydroxymethylcytosine DNA Standard Set. 2010. 2 pages.

Chabon, Jacob J., et al. Integrating genomic features for non-invasive early lung cancer detection. Nature 580.7802: 245-251. (2020).

Choy, L.Y.; et al. Single-Molecule Sequencing Enables Long Cell-Free DNA Detection and Direct Methylation Analysis for Cancer Patients, Clinical Chemistry, vol. 68, Issue 9, pp. 11511163. (2022).

DNA Methylation Control Package Manual. Technical Data Sheet. Diagenode, Mar. 28, 2019. Available at URL: https://www.diagenode.com/files/products/kits/Datasheet_DNA_methylation_control_package.pdf pp. 1-2.

MagMeDIP qPCR Kit Manual: Magnetic Methylated DNA Immunoprecipitation Kit. Version 2. Diagenode, Mar. 2019. Available at URL: https://www.diagenode.com/files/products/kits/MagMeDIP-kit-complete-manual.pdf pp. 1-52.

Pappalardo, Xena Giada; et al. Losing DNA methylation at repetitive elements and breaking bad. Epigenetics & chromatin 14.1: 25. (2021).

Razavi, Pedram. et al. High-intensity sequencing reveals the sources of plasma circulating cell-free DNA variants. Nature Medicine 25(12):1928-1937 (2019).

U.S. Appl. No. 17/736,570 Office Action dated Aug. 8, 2025.

U.S. Appl. No. 18/820,166 Corrected Notice of Allowability dated Nov. 25, 2025.

U.S. Appl. No. 18/820,166 Notice of Allowance dated Oct. 14, 2025.

* cited by examiner

Saturation Analysis

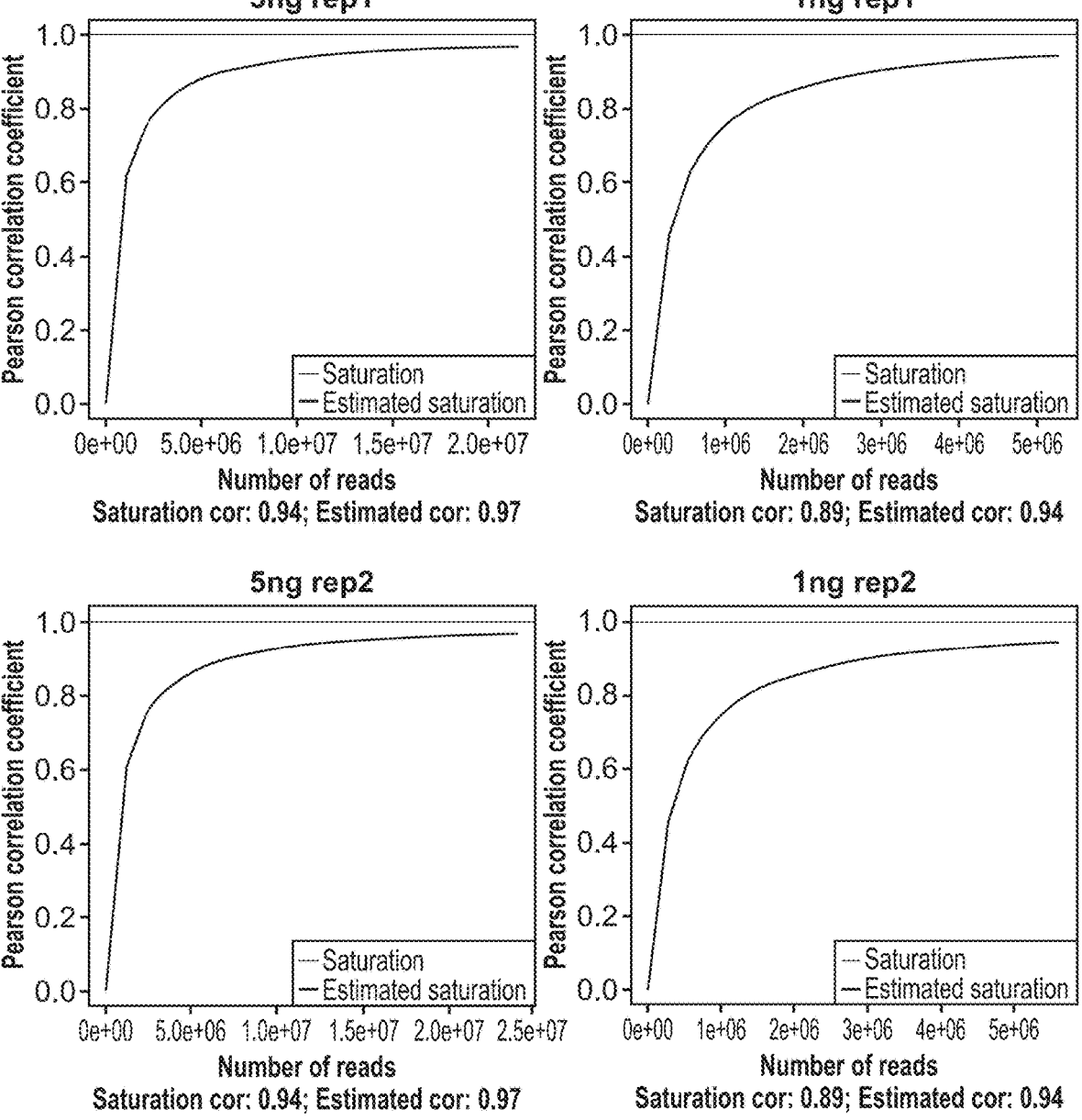
FIG. 3A (Cont. 1)
Saturation Analysis

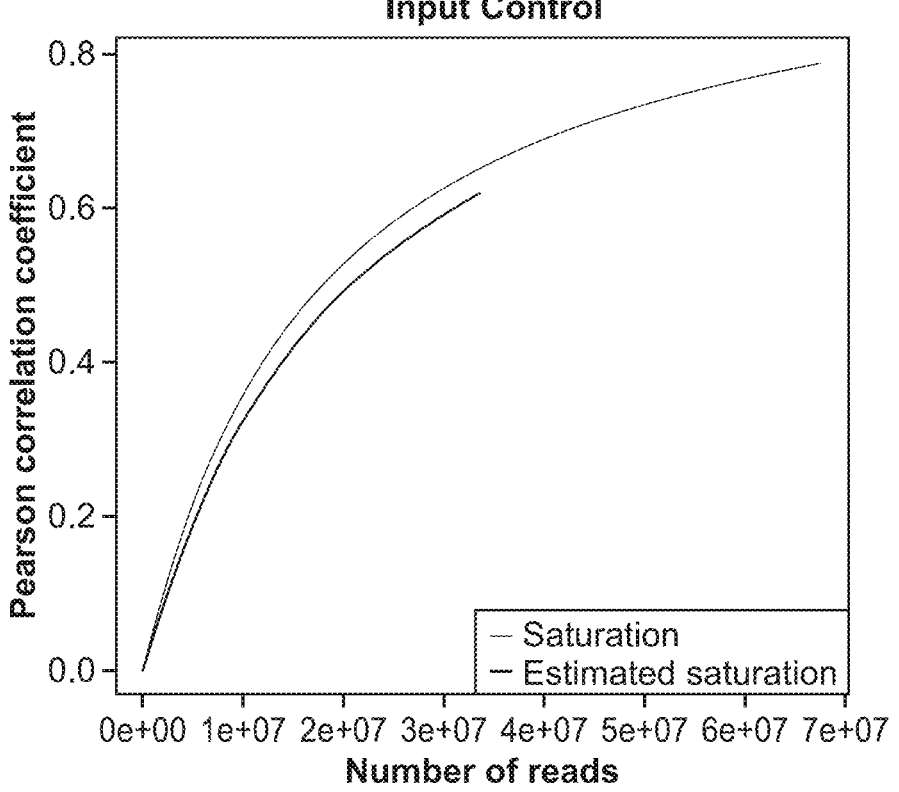
FIG. 3A (Cont. 2)
Saturation Analysis

| % of CRC DNA | 100% | 10% | 1% | 0.1% | 0.01% | 0.001% | 0% |
| --- | --- | --- | --- | --- | --- | --- | --- |
| % of MM DNA | 0% | 90% | 99% | 99.9% | 99.99% | 99.999% | 100% |

Saturation cor: 0.94; Estimated cor: 0.97     Saturation cor: 0.94; Estimated cor: 0.97

Saturation cor: 0.93; Estimated cor: 0.95

METHODS OF CAPTURING CELL-FREE METHYLATED DNA AND USES OF SAME

CROSS-REFERENCE TO RELATED APPLICATIONS

This application is a continuation of U.S. patent application Ser. No. 18/059,370, filed Nov. 28, 2022, which is a continuation of U.S. patent application Ser. No. 17/519,350, filed Nov. 4, 2021, now U.S. Pat. No. 11,560,558, which is a continuation of U.S. patent application Ser. No. 17/353, 756, filed Jun. 21, 2021, which is a continuation of U.S. patent application Ser. No. 16/098,620, filed Nov. 2, 2018, now U.S. Pat. No. 11,078,475, which is a U.S. National Stage Application under 35 U.S.C. 0371 of International Patent Application No. PCT/CA2017/000108, filed May 3, 2017, which claims priority to U.S. Provisional Patent Application No. 62/331,070, filed May 3, 2016, each of which is entirely incorporated herein by reference.

SEQUENCE LISTING

The instant application contains a Sequence Listing which has been submitted electronically in XML format and is hereby incorporated by reference in its entirety. Said XML copy, created on Jun. 18, 2025, is named 59572-702.305_SL.xml and is 16,662 bytes in size.

FIELD OF THE INVENTION

The invention relates to the field of cell free DNA and, more specifically, to methods and uses of capturing cell-free methylated DNA.

BACKGROUND OF THE INVENTION

DNA methylation is a covalent modification of DNA and a stable gene regulatory mechanism that plays an important role in the chromatin architecture. In humans, DNA methylation primarily occurs at cytosine residues in CpG dinucleotides. Unlike other dinucleotides, CpGs are not evenly distributed across the genome but are instead concentrated in short CpG-rich DNA regions called CpG islands. DNA methylation can lead to gene repression by two main mechanisms: 1) recruiting methyl binding domain proteins, which can in turn recruit histone deacetylases (HDACs) and 2) blocking the access to binding sites of transcription factors (TFs), such as c-MYC[1].

In general, the majority of the CpG sites in the genome are methylated, while most of the CpG islands remain unmethylated during normal development and in differentiated tissues[1]. Despite this fact, it is possible to identify tissue-specific patterns of DNA methylation in normal primary tissues[2]. Moreover, during malignant transformation, global DNA hypomethylation, and focal hypermethylation at CpG islands are frequently observed. In fact, DNA methylation patterns have been used to stratify cancer patients into clinically relevant subgroups with prognostic value in glioblastoma[3], ependyrnomas[4], colorectal[5], breast[6,7], among many other cancer types.

Due to its stability and role in normal differentiation and diseases such as cancer, DNA methylation is a good biomarker that can be used to represent tumor characteristics and phenotypic states and therefore, has high potential for personalized medicine.

Many sample types are suitable for DNA methylation mapping and for biomarker discovery including fresh and FFPE tumor tissue, blood cells, urine, saliva, stool, among others[8]. More recently, the use of circulating cell-free DNA (cfDNA) as a biomarker is gaining momentum, especially in situations where genomic distinctions exist, such as in cancer (somatic mutations) 9, transplants (donor versus recipient DNA)[10] and pregnancy (fetus versus mother DNA)[11,12]. Use of DNA methylation mapping of cfDNA as a biomarker could have a significant impact, as it could allow for the identification of the tissue-of-origin and stratify cancer patients in a minimally invasive fashion. Moreover, it could enable the use of cfDNA as a biomarker in situations where genomic distinctions do not exist, such as monitoring immune response, neurodegenerative diseases or myocardial infarction, where the epigenetic aberration can be detected in the cfDNA.

Furthermore, using genome-wide DNA methylation mapping of cfDNA could overcome a critical sensitivity problem in detecting circulating tumor DNA (LIMA) in patients with early-stage cancer with no radiographic evidence of disease. Existing ctDNA detection methods are based on sequencing mutations and have limited sensitivity in part due to the limited number of recurrent mutations available to distinguish between tumor and normal circulating cfDNA[13,14]. On the other hand, genome-wide DNA methylation mapping leverages large numbers of epigenetic alterations that may be used to distinguish circulating tumor DNA (ctDNA) from normal circulating cell-free DNA (cfDNA). For example, some tumor types, such as ependymomas, can have extensive DNA methylation aberrations without any significant recurrent somatic mutations[4].

Moreover, pan-cancer data from The Cancer Genome Atlas (TCGA) shows large numbers of DMRs between tumor and normal tissues across virtually all tumor types[15]. Therefore, these findings highlighted that an assay that successfully recovered cancer-specific DNA methylation alterations from ctDNA could serve as a very sensitive tool to detect, classify, and monitor malignant disease with low sequencing-associated costs.

However, genome-wide mapping DNA methylation in cfDNA is extremely challenging due to the low amount of DNA available and to the fact that cfDNA is fragmented to less than 200 bp in length[16]. This makes it impossible to perform traditional MeDIP-seq, which needs at least 50-100 ng of DNA[17] or RRBS (Reduced Representation Bisulfite Sequencing), which needs non-fragmented DNA[18]. Another issue to mapping DNA methylation in cfDNA, is the low abundance of the DNA of interest within the normal cfDNA[19]. This makes it impractical to perform WGBS, as the cost of sequencing with enough depth to capture the low abundance DNA is prohibitive. On the other hand, a method that selectively enriches for CpG-rich features prone to methylation is likely to maximize the amount of useful information available per read, decrease the cost, and decrease the DNA losses.

SUMMARY OF INVENTION

According to one aspect, there is provided a method of capturing cell-free methylated DNA from a sample having less than 100 ng of cell free DNA, comprising the steps of: subjecting the sample to library preparation to permit subsequent sequencing of the cell-free methylated DNA; adding a first amount of filler DNA to the sample, wherein at least a portion of the filler DNA is methylated; denaturing the sample; and capturing cell-free methylated DNA using a binder selective for methylated polynucleotides.

BRIEF DESCRIPTION OF FIGURES

Embodiments of the invention may best be understood by referring to the following description and accompanying drawings. In the drawings:

FIG. 1A shows Computer Simulation of the probability to detect at least one epimutation as a function of the concentration of ctDNA (columns), number of DMRs being investigated (rows), and the sequencing depth (x-axis). FIG. 1B shows Genome-wide Pearson correlation between DNA methylation signal for 1 to 100 ng of input DNA from HCT116 cell line fragmented to mimic plasma cfDNA. Each concentration has two biological replicates. FIG. 1C shows a DNA methylation profile obtained from cfMeDIP-seq from different concentrations of input DNA from HCT116 (Green Tracks) plus RRBS (Reduced Representation Bisulfite Sequencing) HCT116 data obtained from ENCODE (ENCSR000DFS) and WGBS (Whole-Genome Bisulfite Sequencing) HCT116 data obtained from GEO (GSM1465024). For the heatmap (RRBS track), yellow means methylated, blue means unmethylated and gray means no coverage. FIGS. 1D-1E show Serial dilution of the CRC cell line HCT116 into the Multiple Myeloma (MM) cell line MM1.S. cfMeDIP-seq was performed in pure HCT116 DNA (100% CRC), pure MM1.S DNA (100% MM) and 10%, 1%, 0.1%, 0.01%, and 0.001% CRC DNA diluted into MM DNA. All DNA was fragmented to mimic plasma cfDNA. We observed an almost perfect linear correlation ($r^2$=0.99, p<0.0001) between the observed versus expected (D) numbers of DMRs and (E) the DNA methylation signal (in RPKM) within those DMRs. FIG. 1F shows in the same dilution series, known somatic mutations are only detectable at $\frac{1}{100}$ allele fraction by ultra-deep (>10,000×) targeted sequencing, above the background sequencer and polymerase error rate. Shown are the fractions of reads containing each base or an insertion/deletion at the site of each mutation in the CRC cell line. FIG. 1G shows Frequency of ctDNA (human) as a percentage of total cfDNA (human+mice) in the plasma of mice harboring patient-derived xenograft (PDX) from two colorectal cancer patients.

FIG. 3A shows the results of the saturation analysis from the Bioconductor package MEDIPS analyzing cfMeDIP-seq data from each replicate for each input concentration from the HCT116 DNA fragmented to mimic plasma cfDNA. FIG. 3B shows the protocol was tested in two replicates of four starting DNA concentrations (100, 10, 5, and 1 ng) of HCT116 cell line. Specificity of the reaction was calculated using methylated and unmethylated spiked-in A. thaliana DNA. Fold enrichment ratio was calculated using genomic regions of the fragmented HCT116 DNA (Primers for methylated testis-specific H2B, TSH2BO and unmethylated human DNA region (GAPDH promoter)). The horizontal dotted line indicates a fold-enrichment ratio threshold of 25. Error bars represent ±1 s.e.m. FIG. 3C shows CpG Enrichment Scores of the sequenced samples show a robust enrichment of CpGs within the genomic regions from the immunoprecipitated samples compared to the input control. The CpG Enrichment Score was obtained by dividing the relative frequency of CpGs of the regions by the relative frequency of CpGs of the human genome. Error bars represent ±1 s.e.m.

FIG. 4A shows schematic representation of the CRC DNA (HCT116) dilution into MM DNA (MM1.S). FIG. 4B shows specificity of reaction for each dilution was calculated using methylated and unmethylated spiked-in A. thaliana DNA. C) CpG Enrichment Scores of the sequenced samples show a strong enrichment of CpGs within the genomic regions from the immunoprecipitated samples. The CpG Enrichment Score was obtained by dividing the relative frequency of CpGs of the regions by the relative frequency of CpGs in the human genome. FIG. 4D shows the results of the saturation analysis from each dilution point.

FIG. 5A shows experimental design. FIG. 5B shows volcano plot for circulating cfDNA from pancreatic cancer (cases, n=24) versus healthy donors (controls, n=24) using cfMeDIP-seq. Red dots indicate the windows that reached significance after correction for multiple tests. FIG. 5C shows heatmap of the 38,085 DMRs identified in the plasma DNA from healthy donors and pancreatic cancer patients. Hierarchical clustering method: Ward. FIG. 5D shows permutation analysis to estimate the frequency of expected versus the observed overlap between the DMRs identified in the plasma (cases versus controls) and the cancer-specific DMCs identified in the primary tumor tissue (primary tumor versus normal tissue). The box-plots represent the null distribution for the overlap. The diamonds represent the experimentally observed number of overlap between primary tumor tissue and DNA methylation from circulating cfDNA. Red diamonds mean the observed number of overlaps is significantly more than expected by chance. Green diamonds mean that the observed number of overlaps is significantly less than expected by chance and blue diamonds are non-significant. We calculated four possible overlaps: Hypermethylated in the primary tumor tissue and hypermethylated in the circulating cfDNA (Enriched, P-value: $6.4\times10^{-22}$); Hypermethylated in the tumor tissue and hypomethylated in the circulating cfDNA (Depleted, P-value: $9.43\times10^{-17}$); Hypomethylated in the tumor tissue and hypomethylated in the circulating cfDNA (Enriched, P-value: $1.88\times10^{-283}$); Hypomethylated in the tumor tissue and hypermethylated in the circulating cfDNA (P-value: 0.105). FIG. 5E shows permutation analysis to estimate the frequency of expected versus the observed overlap between the DMRs identified in the plasma (cases versus controls) and the cancer-specific DMCs identified in the primary tumor tissue (primary tumor versus normal PBMCs).

FIGS. 6A-B show specificity of reaction for each case (A) and each control (B) sample was calculated using methylated and unmethylated spiked-in A. thaliana DNA. Fold enrichment ratio was not calculated due to the very limited amount of DNA available. FIGS. 6C-D shows CpG Enrichment Scores of the sequenced samples show a strong enrichment of CpGs within the genomic regions from the immunoprecipitated samples.

FIG. 8A shows expression profile of all TFs (n=33) whose motifs were enriched (using the software HOMER[20]) in the regions hypomethylated in the cfDNA from healthy donors (hypomethylated footprints in controls) across multiple human tissues. The expression data was obtained from the Genotype-Tissue Expression (GTEx) project[21]. Several TFs preferentially expressed in the hematopoietic system were identified (PU.1, Fli1, STAT5B, KLF1). FIG. 8B shows expression profile of all TFs with hypomethylated motifs in controls (n=33) versus the expression profile of 1,000 random sets of 33 TFs in whole blood (GTEx data). FIG. 8C shows expression profile of all TFs (n=85) whose motifs were enriched in the regions hypomethylated in the cfDNA from pancreatic adenocarcinoma patients (hypomethylated footprints in cases). Several pancreas-specific or pancreatic cancer-associated TFs were identified. Moreover, hallmark TFs that drive molecular subtypes of pancreatic cancer were also identified. FIG. 8D shows expression profile of all TFs with hypomethylated motifs in cases (n=85) versus the expression profile of 1,000 random sets of 85 TFs in normal pancreas (GTEx data). FIG. 8E shows Expression profile of all TFs with hypomethylated motifs in cases (n=85) versus the expression profile of 1,000 random sets of 85 TFs in pancreatic adenocarcinoma tissue (TCGA data).

DETAILED DESCRIPTION

Figure 1A:
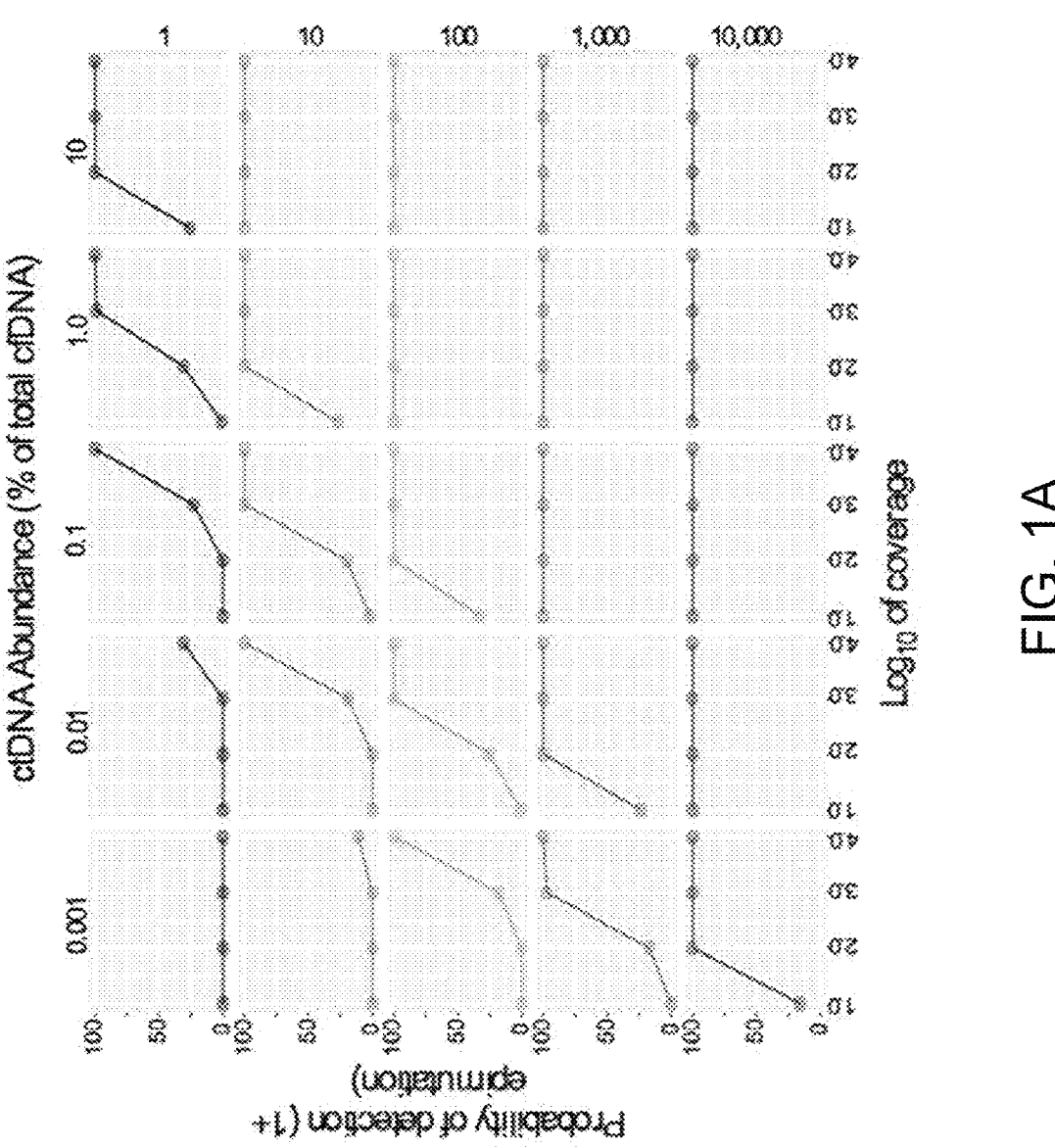
FIGS. 1A-1G shows the methylome analysis of cfDNA is a highly sensitive approach to enrich and detect ctDNA in low amounts of input DNA.

We bioinformatically simulated mixtures with different proportions of ctDNA, from 0.001% to 10% (FIG. 1A, column facets). We also simulated scenarios where the ctDNA had 1, 10, 100, 1000, or 10000 DMRs (Differentially Methylated Regions) as compared to normal cfDNA (FIG. 1A, row facets). Reads were then sampled at varying sequencing depths at each locus (10×, 100×, 1000×, and 10000×) (FIG. 1A, x-axis). We found an increasing probability of detecting of at least 1 cancer-specific event (FIG. 1A) as the number of DMRs increased, even at low abundance of cancer cfDNA and shallow coverage.

Figure 2:
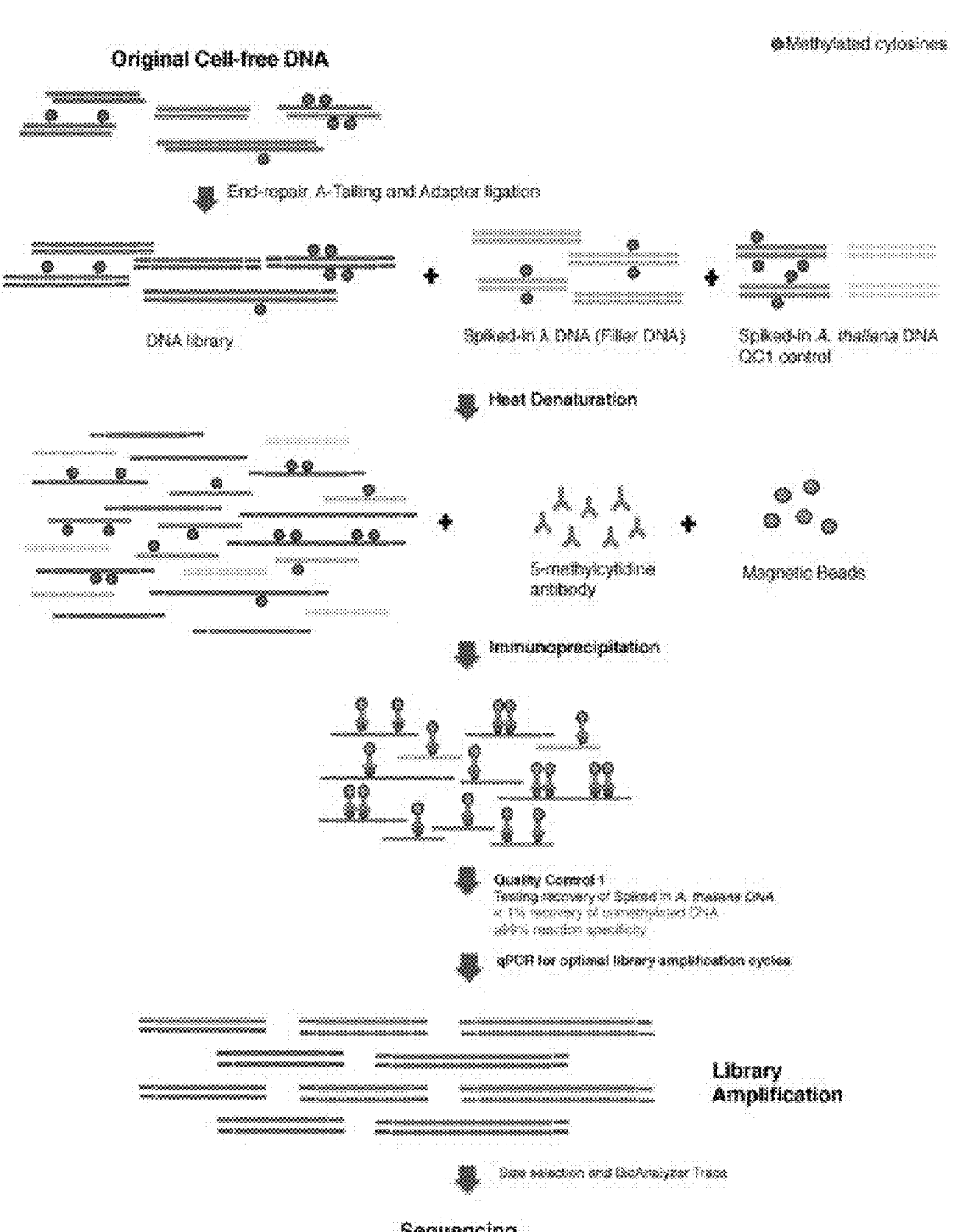
FIG. 2 shows the schematic representation of the cfMeDIP-seq protocol.
Figure 9:
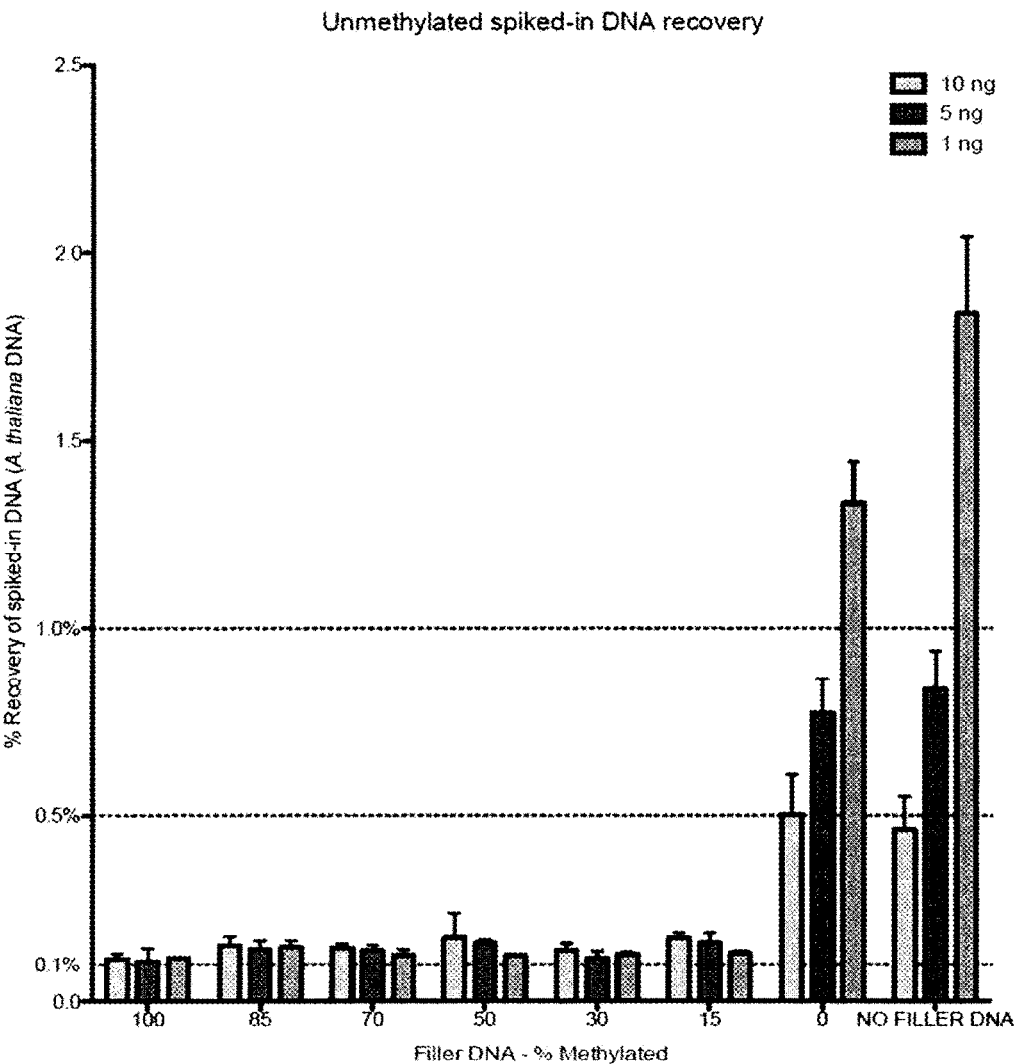
FIG. 9 shows % Recovery of spiked-in unmethylated *A. thaliana* DNA after cfMeDIP-seq using 10 ng, 5 ng and 1 ng of starting cancer cell-free DNA amounts (n=3), combined with 90 ng, 95 ng and 99 ng of filler DNA respectively or no filler DNA, prior to immunoprecipitation. The filler DNA used varied in the composition of % artificially methylated to % unmethylated lambda DNA present to increase final amount prior to immunoprecipitation to Wang. The % recovery of spiked-in unmethylated DNA desired is <1.0%, with lower recovery resulting in higher % specificity of reaction.
Figure 10:
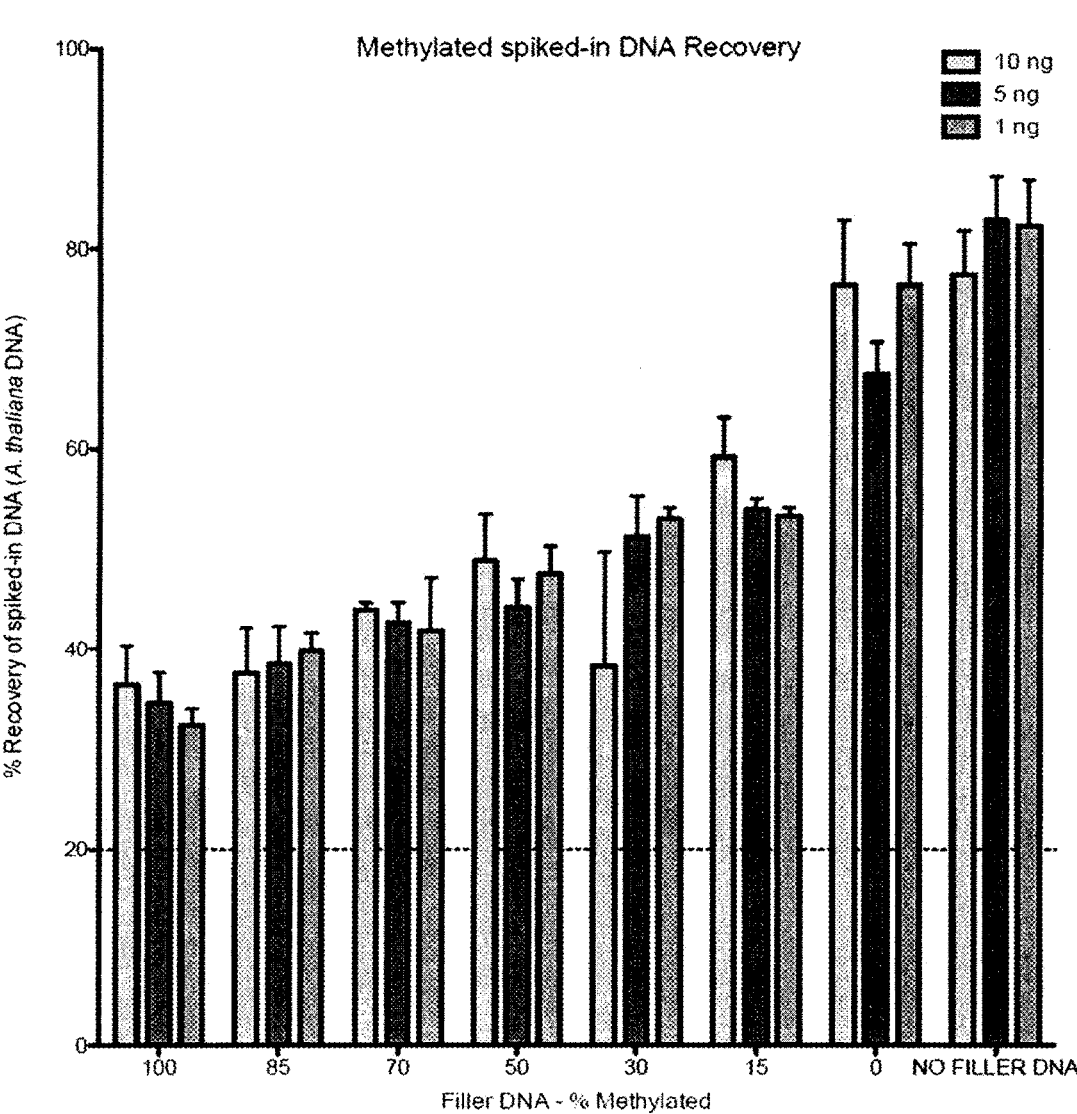
FIG. 10 shows % Recovery of spiked-in methylated *A. thaliana* DNA after cfMeDIP-seq using long, 5 ng and 1 ng of starting cancer cell-free DNA amounts (n=3), combined with 90 ng, 95 ng and 99 ng of filler DNA respectively or no filer DNA, prior to immunoprecipitation. The filler DNA used varied in the composition of % artificially methylated to % unmethylated lambda DNA present to increase final amount prior to immunoprecipitation to 100 ng. Minimum % recovery of spiked-in methylated DNA desired is 20%.

To overcome these challenges, we have developed a new method called cfMeDIP-seq (cell-free Methylated DNA Immunoprecipitation and high-throughput sequencing) to perform genome-wide DNA methylation mapping using cell-free DNA. The cfMeDIP-seq method described here was developed through the modification of an existing low input MeDIP-seq protocol[17] that is robust down to 100 ng of input DNA. However, the majority of plasma samples yield much less than 100 ng of DNA. To overcome this challenge, we added exogenous λ DNA (filler DNA) to the adapter-ligated cfDNA library in order to artificially inflate the amount of starting DNA to 100 ng (FIG. 2). This minimizes the amount of non-specific binding by the antibody and also minimizes the amount of DNA lost due to binding to plasticware. The filler DNA consisted of amplicons similar in size to an adapter-ligated cfDNA library and was composed of unmethylated and in vitro methylated DNA at different methylation levels (FIG. 9 and FIG. 10). The addition of this filler DNA also serves a practical use, as different patients will yield different amounts of cfDNA, allowing for the normalization of input DNA amount to 100 ng. This ensures that the downstream protocol remains exactly the same for 21i samples regardless of the amount of available cfDNA, According to one aspect, there is provided a method of capturing cell-free methylated DNA from a sample having less than 100 ng of cell-free DNA, comprising the steps of:

a. subjecting the sample to library preparation to permit subsequent sequencing of the cell-free methylated DNA;

b. adding a first amount of filler DNA to the sample, wherein at least a portion of the filler DNA is methylated;

c. denaturing the sample; and d. capturing cell-free methylated DNA using a binder selective for methylated polynucleotides.

In some embodiments, this method further comprises the step of amplifying and subsequently sequencing the captured cell-free methylated DNA.

Various sequencing techniques are known to the person skilled in the art, such as polymerase chain reaction (PCR) followed by Sanger sequencing. Also available are next-generation sequencing (NGS) techniques, also known as high-throughput sequencing, which includes various sequencing technologies including: Illumina (Solexa) sequencing, Roche 454 sequencing, Ion torrent Proton/PGM sequencing, SOLID sequencing. NGS allow for the sequencing of DNA and RNA much more quickly and cheaply than the previously used Sanger sequencing. In some embodiments, said sequencing is optimized for short read sequencing.

Cell-free methylated DNA is DNA that is circulating freely in the blood stream, and are methylated at various known regions of the DNA. Samples, for example, plasma samples can be taken to analyze cell-free methylated DNA.

As used herein, library preparation" includes List end-repair, A-tailing, adapter ligation, or any other preparation performed on the cell free DNA to permit subsequent sequencing of DNA.

As used herein, "filler DNA" can be noncoding DNA or it can consist of amplicons. DNA samples may be denatured, for example, using sufficient heat.

In some embodiments, samples have less than 50 ng of cell-free DNA.

In some embodiments, the first amount of filler DNA comprises about 10%, 20%, 30%, 40%, 50%, 60%, 70%, 80%, 90%, or 100% methylated filler DNA. In preferred embodiments, the first amount of filler DNA comprises about 50% methylated filler DNA.

In some embodiments, the first amount of filler DNA is from 20 ng to 100 ng. In preferred embodiments, 30 ng to 100 ng of filler DNA. In more preferred embodiments 50 ng to 100 ng of filler DNA. When the cell-free DNA from the sample and the first amount of filler DNA are combined together, there comprises at least 50 ng of total DNA, and preferably at least 100 ng of total DNA.

In some embodiments, the filler DNA is 50 bp to 800 bp long. In preferred embodiments, 100 bp to 600 bp long; and in more preferred embodiments 200 bp to 600 bp long.

The filler DNA is double stranded. For example, the filler DNA can be junk DNA. The filler DNA may also be endogenous or exogenous DNA. For example, the filler DNA is non-human DNA, and in preferred embodiments, A DNA. As used herein, "A DNA" refers to Enterobacteria phage A DNA. In some embodiments, the filler DNA has no alignment to human DNA.

In some embodiments, the binder is a protein comprising a Methyl-CpG-binding domain. One such exemplary protein is MBD2 protein. As used herein, "Methyl-CpG-binding domain (MBD)" refers to certain domains of proteins and enzymes that is approximately 70 residues long and binds to DNA that contains one or more symmetrically methylated CpGs. The MED of MeCP2, MBD1, MBD2, MBD4 and BAZ2 mediates binding to DNA, and in cases of MeCP2, MBD1 and MBD2, preferentially to methylated CpG. Human proteins MECP2, MBD1, MBD2, MBD3, and MBD4 comprise a family of nuclear proteins related by the presence in each of a methyl-CpG-binding domain (MBD). Each of these proteins, with the exception of MBD3, is capable of binding specifically to methylated DNA.

In other embodiments, the binder is an antibody and capturing cell-free methylated DNA comprises irnmunoprecipitating the cell-free methylated DNA using the antibody. As used herein, "immunoprecipitation" refers a technique of precipitating an antigen (such as polypeptides and nucleotides) out of solution using an antibody that specifically binds to that particular antigen. This process can be used to isolate and concentrate a particular protein or DNA from a sample and requires that the antibody be coupled to a solid substrate at some point in the procedure. The solid substrate includes for examples beads, such as magnetic beads. Other types of beads and solid substrates are known in the art.

One exemplary antibody is 5-MeC antibody. For the immunoprecipitation procedure, in some embodiments at least 0.05 µg of the antibody is added to the sample; while in more preferred embodiments at least 0.16 µg of the antibody is added to the sample. To confirm the immunoprecipitation reaction, in some embodiments the method described herein further comprises the step of adding a second amount of control DNA to the sample after step (b).

Another exemplary antibody is or 5-hydroxymethyl cytosine antibody.

In other embodiments, the method described herein further comprises the step of adding a second amount of control DNA to the sample after step (b) for confirming the capture of cell-free methylated DNA.

As used herein, the "control" may comprise both positive and negative control, or at least a positive control.

According to a further aspect, there is provided use of the methods described herein for measuring a DNA methylation profile within the sample.

According to a further aspect, there is provided use of the methods described herein to identify the presence of cell free DNA from cancer cells within the sample by correlating the profile with known methylation profiles of tumour tissue.

According to a further aspect, there is provided use of the DNA methylation profile as described herein for identifying tissue-of-origin of the cell-free DNA within the sample by correlating the profile with known methylation profiles of specific tissues.

In some embodiments, the use further comprising the use of described herein for identifying tissue of origin of the cancer cells within the cell-free DNA within the sample.

According to a further aspect, there is provided the use described herein for monitoring immune therapy.

According to a further aspect, there is provided the use described herein for the diagnosis of autoimmune conditions.

According to a further aspect, there is provided the use described herein for determining cell turnover in a subject from which the sample is taken.

The following examples are illustrative of various aspects of the invention, and do not limit the broad aspects of the invention as disclosed herein.

EXAMPLES

Methods

Donor Recruitment and Sample Acquisition

Pancreatic adenocarcinoma (PDAC) patient samples were obtained from the University Health Network BioBank; healthy controls were recruited through the Family Medicine Centre et Mount Sinai Hospital (MSH) in Toronto, Canada. All samples collected with patient consent, were obtained with institutional approval from the Research Ethics Board, from University Health Network and Mount Sinai Hospital in Toronto, Canada.

Specimen Processing—Purified Tumor and Normal Cells

For primary PDAC samples, specimens were processed immediately following resection and representative sections were used to confirm the diagnosis. Laser capture micro-dissection (LCM) of freshly liquid nitrogen-frozen tissue samples was performed on a Leica LIVID 7000 instrument. Briefly, frozen tissue maintained in vapor-phase liquid nitro-gen was embedded in OCT cutting medium and sectioned in a cryotome into 8-pm thick sections. Sections were mounted on PEN membrane slides (Leica) and lightly stained with hematoxylin to facilitate microscopic identification of tumor areas. LCM was performed on the same day when sections were cut to minimize nucleic acid degradation.

Microdissected tumor cells were collected by gravity into the caps of sterile, RNAse-free microcentrifuge tubes. Approximately 150,000-200,000 tumor cells were collected for DNA sample and stored at −80 C. until further process-ing. LCM typically took 1-2 days per case to collect suffi-cient amounts of purified tumor cells. Qiagen Cell Lysis buffer was used to extract genomic DNA. Matched normal, histologically reviewed reference tissue was collected for each patient from frozen duodenal or gastric mucosa by scraping unstained frozen sections on glass slides into the appropriate DNA extraction buffer.

Specimen Processing—cfDNA

EDTA and ACD plasma samples were obtained from the BioBank and from the Family Medicine Centre at Mount Sinai Hospital (MSH) in Toronto, Canada. All samples were either stored at −80° C. or in vapour phase liquid nitrogen until use. Cell-free DNA was extracted from 0.5-3.5 ml of plasma using the QIAamp Circulating Nucleic Acid Kit (Qiagen). The extracted DNA was quantified through Qubit prior to use.

Specimen Processing—PDX cfDNA

Human colorectal tumor tissue obtained with patient consent from the University Health Network I3iobank as approved by the Research Ethics Board at University Health Network, was digested to single cells using collagenase A. Single cells were subcutaneously injected into 4-6 week old NOD/SUED male mouse. Mice were euthanized by CO2 inhalation prior to blood collection by cardiac puncture and stored in EDTA tubes. From the collected blood samples, the plasma was isolated and stored at −80 C. Cell-free DNA was extracted from 0.3-0.7 ml of plasma using the QIAamp Circulating Nucleic Acid Kit (Qiagen). All animal work was carried out in compliance with the ethical regulations approved by the Animal Care Committee at University Health Network.

RRBS

Genomic DNA extracted from the LCM-enriched tumor and normal samples coming from the same patients, for who the cell-free DNA had been obtained, was subjected to RRES following the protocol from Gu et al., 201119 with minor modifications. Briefly, 10 rig of genomic DNA, determined through Qubit, was digested using restriction enzyme Mspl, then subjected to end-repair, A-tailing and adapter ligation to Illumina TruSeq methylated adapters. The prepared libraries were then subjected to bisulfate conversion using the Zymo EZ DNA methylation kit fol-lowing manufacturer's protocol, followed by gel size selec-tion for fragments of 160 bp-300 bp_ The optimal number of cycles to amplify each purified library was determined through the use of qPCR, after which the samples were amplified using the KAPA HiFi Uracil+ Mastermix (Kapa Biosystems) and purified with AMPure beads (Beckman Coulter). The final libraries were submitted for BioAnalyzer analysis prior to sequencing at the UHN Princess Margaret Genomic Centre in an Illumina HiSeq 2000.

Preparation of Exogenous Enterobacteria Phage λ PCR Product

Enterobacteria phage λ DNA (ThermoFischer Scientific) was amplified using the primers indicated in Table 1, gen-erating 6 different PCR amplicons products. The PCR reac-tion was carried out using KAPA HiFi Hotstart ReadyMix with the following condition: activation of enzyme at 95° C. for 3 min, 30 cycles of 98° C. for 20 sec, 60° C. for 15 sec, 72° C. for 30 sec and a final extension at 72° C. for 1 min. The PCR amplicons were purified with 01ACIuick PCR purification kit (Qiagen) and ran on a gel to verify size and amplification. Amplicons for 1 CpG, 5 CpG, 10 CpG, 15 CpG and 20 CpGL were methylated using CpG Methyl-transferase (M.Sssl) (ThermoFischer Scientific) and purified with the OIAQuick PCR purification kit Methylation of the PCR amplicons was tested using restriction enzyme HpyCH4lV (New England Biolabs Canada) and ran on a gel to ensure its methylation. The DNA concentration of the unmethylated (20 CpGS) and methylated (1 CpG, 5 CpG, 10 CpG, 15 CpG, 20 CpGL) amplicons was measured using picogreen prior to pooling with 50% of methylated and 50% unmethylated λ PCR product.

cfMeDIP-seq

A schematic representation of the cfMeDIP-seq protocol is shown in FIG. 2. Prior to cfMeDIP, the DNA samples were subjected to library preparation using the Kapa Hyper Prep Kit (Kapa Biosystems). The manufacturer protocol was followed with some modifications. Briefly, the DNA of interest was added to 0.2 mL PCR tube and subjected to end-repair and A-Tailing. Adapter ligation was followed using NEBNext adapter (from the NEBNext Multiplex Oligos for Illumina kit, New England Giolabs) at a final concentration of 0.181 µM, incubated at 20° C. far 20 mins and purified with AMPure XP beads. The eluted library was digested using the USER enzyme (New England I3iolabs Canada) followed by purification with Qiagen MinElute PCR Purification Kit prior to MeDIP.

The prepared libraries were combined with the pooled methylated/unmethylated λ PCR product to a final DNA amount of 100 ng and subjected to MeDIP using the protocol from Taiwo et al. 201217 with some modifications. For MeDIP, the Diagenode MagIVIeDIP kit (Cat #C02010021) was used following the manufacturer's protocol with some modifications. After the addition of 0.3 ng of the control methylated and 0.3 ng of the control unmethylated *A. thaliana* DNA, the filler DNA (to complete the total amount of DNA [cfDNA Filler+Controls] to 100 ng) and the buffers to the PCR tubes containing the adapter ligated DNA, the samples were heated to 95° C. for 10 mins, then immediately placed into an ice water bath for 10 mins. Each sample was partitioned into two 0.2 mt. PCR tubes: one for the 10% input control and the other one for the sample to be subjected to immunoprecipitation. The included 5-mC monoclonal antibody 33D3 (Cat #C15200081) from the MagMeDIP kit was diluted 1:15 prior to generating the diluted antibody mix and added to the sample. Washed magnetic beads (following manufacturer instructions) were also added prior to incubation at 4° C. for 17 hours. The samples were purified using the Diagenode iPure Kit and eluted in 50 μl of Buffer C. The success of the reaction (QC1) was validated through qPCR to detect the presence of the spiked-in *A. thaliana* DNA, ensuring a % recovery of unmethylated spiked-in DNA<1% and the % specificity of the reaction >99% (as calculated by 1-[recovery of spiked-in unmethylated control DNA aver recovery of spiked-in methylated control DNA]), prior to proceeding to the next step. The optimal number of cycles to amplify each library was determined through the use of qPCR, after which the samples were amplified using the KAPA HiFi Hotstart Mastermix and the NEBNext multiplex oligos added to a final concentration of 0.3 μM. The PCR settings used to amplify the Libraries were as follows: activation at 95° C. for 3 min, followed by predetermined cycles of 98° C. for 20 sec, 65¹° C. for 15 sec and 72° C. for 30 sec and a final extension of 72° C. for 1 min. The amplified libraries were purified using MinElute PCR purification column and then gel size selected with 3% Nusieve GTG agarose gel to remove any adapter dimers. Prior to submission for sequencing, the fold enrichment of a methylated human DNA region (testis-specific H2B, TSH2B) and an unmethylated human DNA region (GAPDH promoter) was determined for the MeDIP-seq and cfMeDIP-seq libraries generated from the HCT116 cell line DNA sheared to mimic cell free DNA (Cell line obtained from ATCC, *mycoplasma* free). The final Libraries were submitted for BioAnalyzer analysis prior to sequencing at the UHN Princess Margaret Genomic Centre on an Illumina HiSeq 2000. Differing % of Methylation in the Filler DNA cfMeDIP-seq was performed using different % of methylated to unmethylated lambda DNA in the filler component of the protocol as follows:

Using filler (lambda) DNA to increase final amount of ONA to 100 ng prior to immunoprecipitation, with the starting amounts of cell-free DNA ranging from 10 ng, 5 ng and 1 ng

| % Methylated Filler | % Unmethylated Filler |
| --- | --- |
| 100 | 0 |
| 85 | 15 |
| 70 | 30 |
| 50 | 50 |
| 30 | 70 |
| 15 | 85 |
| 0 | 100 |

No Filler DNA used-as is only 10 ng, 5 ng or 1 ng of starting DNA prior to immunoprecipitation As shown in FIGS. 9 and 10, the filler DNA (lambda DNA) used to increase the final amounts prior to immunoprecipitation to 10 Ong, should preferably have some artificially methylated DNA in its composition (from 100%-15%) in order to have the minimal recovery unmethylated DNA (FIG. 9), while still getting a good yield in terms of recovery of methylated DNA (FIG. 10). In the samples where we have 100% unmethylated filler DNA or no filler DNA present, although there is really higher recovery of methylated DNA, we also have high % recovery of unmethylated DNA. This shows that the additional methylated DNA in the filler DNA helps to occupy the excess antibody present in the reaction, minimizing the amount of unspecific binding to unmethylated DNA found in the sample. Given that optimizing antibody amounts is not very economical or even feasible in cases where different cell-free DNA samples are used, as it is unknown how much methylated DNA is present throughout the sample and this could differ drastically sample to sample, this filler DNA helps normalize the different starting amounts and allow for different cell-free DNA samples to be processed the same way (i.e use same amount of antibody), while still recovering good methylation data from it.

Ultra-Deep Targeted Sequencing for Point Mutation Detection

We used the QIAgen Circulating Nucleic Acid kit to isolate cell-free DNA from ~20 mL of plasma (4-5×10 mL EDTA blood tubes) from patients with matched tumor tissue molecular profiling data generated prior to enrolment in early phase clinical trials at the Princess Margaret Cancer Centre, DNA was extracted from cell lines (dilution of CRC and MM cell lines) using the PureGene Gentra kit, fragmented to ~180 bp using a Covaris sonicator, and larger size fragments excluded using Ampure beads to mimic the fragment size of cell-free DNA. DNA sequencing libraries were constructed from 83 ng of fragmented DNA using the KAPA Hyper Prep Kit (Kapa Biosystems, Wilmington, MA) utilizing NEXTflex-96 DNA Barcode adapters (Bio Scientific, Austin, TX) adapters. To isolate DNA fragments containing known mutations, we designed biotinylated DNA capture probes (xGen Lockdown Custom Probes Mini Pool, Integrated DNA Technologies, Coralville, IA) targeting mutation hotspots from 48 genes tested by the clinical laboratory using the Illumina TruSeq Amplicon Cancer Panel. The barcoded libraries were pooled and then applied the custom hybrid capture library following manufacturer's instructions (MT xGEN Lockdown protocol version 2.1). These fragments were sequenced to >10,000× read coverage using an Illumina HiSeq 2000 instrument. Resulting reads were aligned using bwa-mem and mutations detected using samtools and muTect version 1.1.4.

Modelling Relationships Between Number of Tumor-Specific Features and Probability of Detection by Sequencing Depth We created 145,000 simulated genomes, with the proportion of cancer-specific methylated DMRs set to 0.001%, 0.01%, 0.1%, 1%, and 10% and consisting of 1, 10, 100, 1000 and 10000 independent DMRs respectively. We sampled 14,500 diploid genomes (representing 'Wong of DNA) from these original mixtures and further sampled 10, 100, 1000, and 10000 reads per locus to represent sequencing coverage at those depths. This process was repeated 100 times for each combination of coverage, abundance, and number of features. We estimated the frequency of successful detection of at least 1 DIM for each combination of parameters and plotted probability curves (FIG. 1A) to visually evaluate the influence of the number of features on the probability of successful detection conditional on sequencing depths.

Figure 5A:
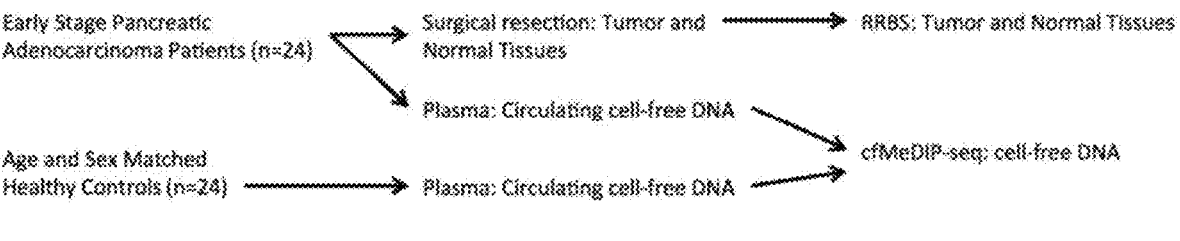
FIGS. 5A-5E show that the cfMeDIP-seq method can identify thousands of differentially methylated regions on circulating cfDNA obtained from pancreatic adenocarcinoma patients.
Figure 5B:
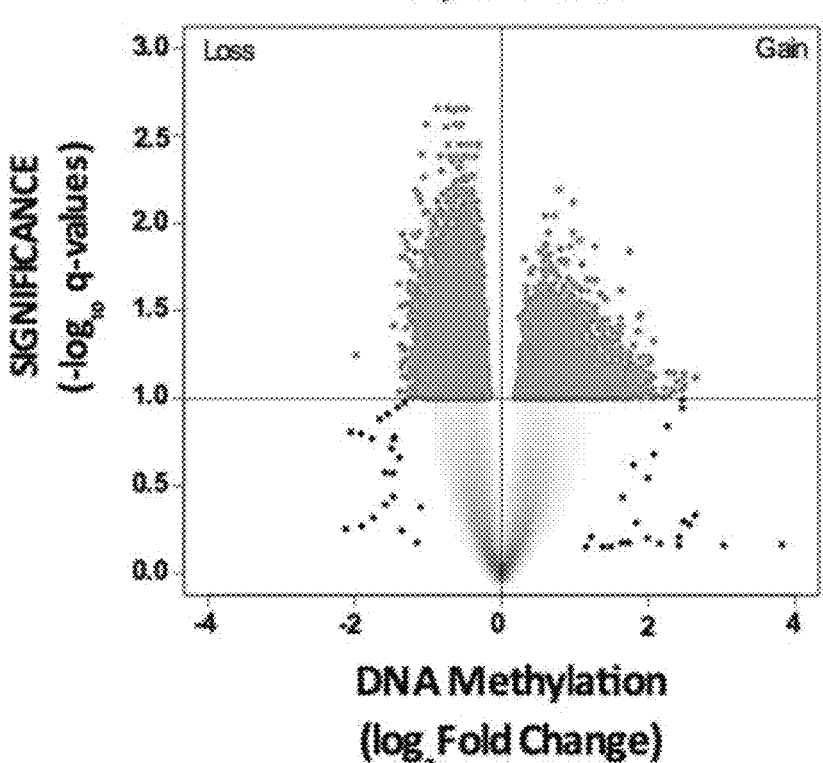
Figure 5C:
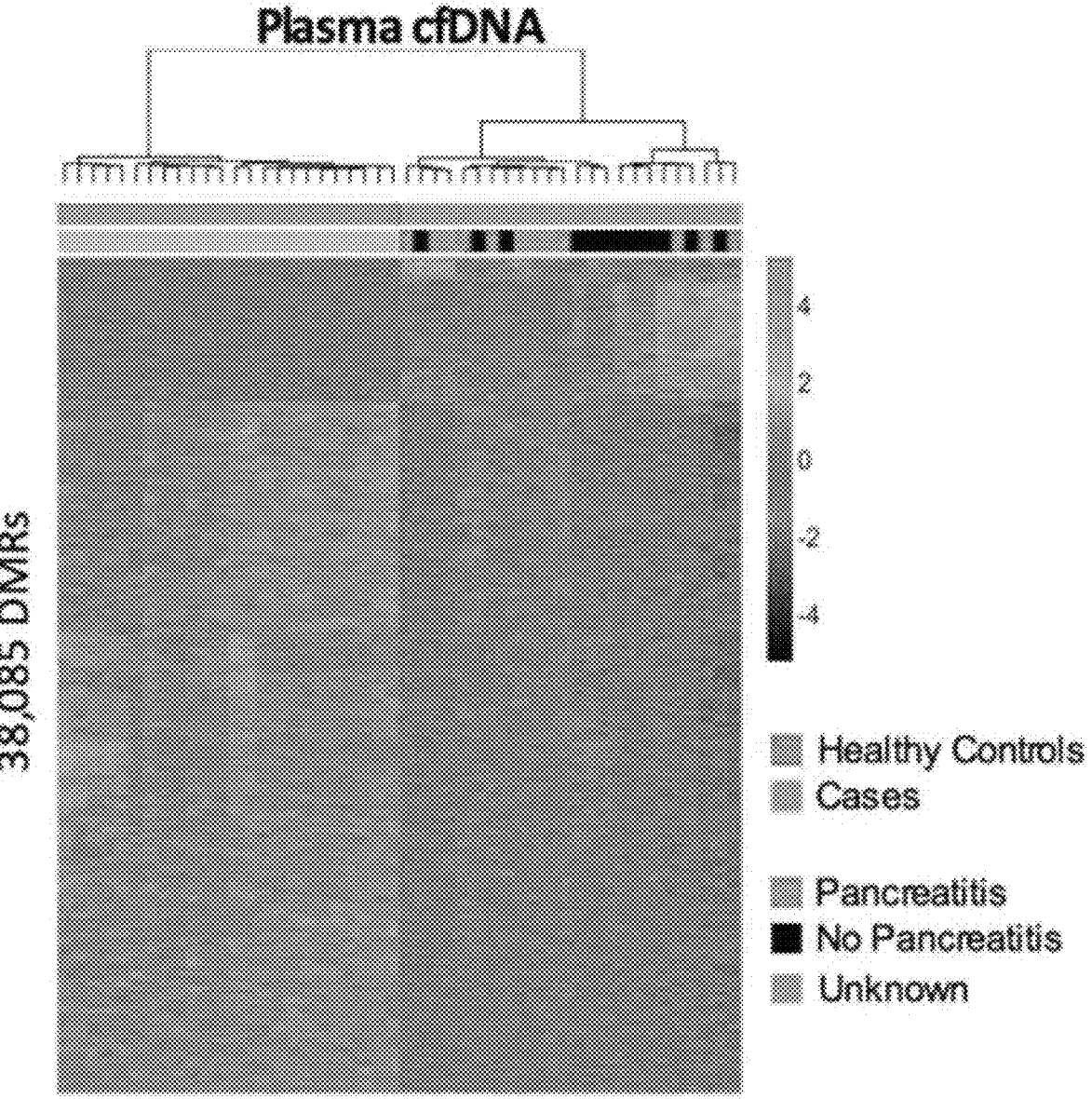

Calculation and Visualization of Differentially Methylated Regions from cfDNA of Pancreatic Cancer Patients and Healthy Donors Differentially Methylated Regions (DMRs) between cfDNA samples from 24 Pancreatic Cancer (PC) patients and 24 Healthy Donors were calculated using the MEDIPS R package[25]_For each sample, the BAM alignment (to human genome hg19) files were used to create MEDIPS R objects. Next, DMRs were calculated by comparing the RPKMs from the two sets of samples using Wests. The raw p-values from the t-tests were adjusted using the Benjamini-Hochberg procedure. DMRs were then defined as all the windows with adjusted p-values less than 0.1; 38,085 total DMRs were found: 6,651 Hyper in Pancreatic Cancer patients and 31,544 Hypo, The scaled RPKM values from these DMRs were presented as a heatmap (FIG. 5C). This heatmap was made with the distance function "euclidean", and the clustering function "ward" for column-wise clustering and "average" for row-wise clustering.

Comparison of RRBS Samples from 24 Pancreatic Cancer Tissues and 5 Normal PBMCs

Five normal PBMC samples profiled by RRBS were downloaded from GEO (all control samples under Accession ID GSE89473) to compare their methylation profiles to those of 24 Pancreatic Cancer tissue RRBS samples. Downloaded bed files were parsed and processed with the R methylKit package[25]. These five samples were next compared to similarly processed RRBS samples from 24 Pancreatic Cancer patients. Custom functions were used to extract GpGs that were present in at least 18 of the 24 PC samples, and 4 of the 5 PBMC samples, and only the CpGs in autosomes were retained, to yield a Background set of 1,806,808 CpGs. From these, DMCs were obtained using the criteria of Benjamini-Hochberg adjusted p-value <0.01 and Delta Beta >0.25, and 134,021 DMCs were found to be Hyper in Pancreatic Cancer compared to PBMCs. Analogously, using the same q-value cutoff and Delta Beta <0.25, we obtained 179,662 Hypo DMCs. The total of 313,683 DMCs are represented by the red points in the corresponding volcano plot (FIG. 7F), in which the negative log 10 of the q-values are plotted against the Delta Betas (the horizontal line at negative log 10 q-value=2 represents the q-value cutoff for calling DMCs, and the dotted vertical lines represents the Delta Beta cutoffs).

Assessment of Overlap of Differential Methylation Signals from Primary Tumors Vs Normal PBMCs and from cfDNA of Pancreatic Cancer Patients and Healthy Donors Permutation analysis was carried out to compare the frequency of expected versus the observed overlap between the DMRs identified in the plasma (with circulating cfDNA subjected to our cfMeDIP-seq protocol) and the cancer-specific DMCs identified in the primary tumor tissue (with RRBS). We examined four possible cases: Hyper DMCs overlapping with Hyper DMRs, Hyper DMCs with Hypo DMRs, Hypo DMCs with Hypo DMRs, and finally, Hypo DMCs with Hyper DMRs. For each case, the Hyper or Hypo DMCs were overlapped with the Hyper or Hypo DMRs to get the number of "biological intersections"; each set of DMCs was then randomly shuffled across the Background set of 1,806,808 CpGs 1000 times, and overlapped again with each set of the DMRs. These random and biological intersections were put on the same scale using Z-scores and are shown with boxplots and diamonds, respectively (FIG. 5E). The dashed horizontal lines in these plots represent the cutoff Z-scores associated with a Bonferroni adjustment-derived q-value of 0.05.

Comparison of RRBS Samples from 24 Pancreatic Cancer Tissues and 24 Normal Tissues & Assessment of Overlap of Differential Methylation Signal from these Tissues and from cfDNA of Pancreatic Cancer Patients and Healthy Donors The 24 PC samples that were compared to 5 Normal PBMC samples were also compared separately to 24 normal tissues from the same patients. The Background set (763,874 CpGs) and DMCs Hyper & Hypo in PC (34,013 & 11,160 respectively) were calculated using the same methodology, and these were used to construct a volcano plot (FIG. 7C) & boxplots (FIG. 50) in the same manner as well.

PCA Plots on 24 PC and 24 Healthy cfDNA Samples

We performed unsupervised clustering analysis with PCA (FIG. 7A-B) on the 24 PC and 24 Healthy cfDNA samples using the top million most variable genome-wide windows. For each window, variability was calculated using the MAD (Mean Absolute Deviation) metric. This is a robust measurement that returns the median of the absolute deviations from the data's median value, where the data is the RPKM values across these 48 samples for a given window.

Heatmaps with GTEx Expression Profiles of TFs Associated with Motifs Hypomethylated in 24 PC and 24 Healthy cfDNA Samples RNA-Seq data was obtained from the GTEx database in the form of median RPKMS by tissue for all human genes (obtained from file GTEx_Analysis_v6p_RNA-seq_RNA-SeQCv1.1.8_gene_median_rpkm.gct.gz under https://gtex-portal.org/home/datasets). TFs of interest were matched to their gene names, and heatmaps (FIG. 8A, 8C) were constructed with the median RPKMs of each TF scaled across all tissues. The distance function "manhattan" and clustering function "average" were used for both row-wise and column-wise clustering.

Violin Plots with GTEx Expression Profiles of TFs Associated with Motifs Hypomethylated in 24 PC and 24 Healthy cfDNA Samples In order to estimate if the TFs for which we detected significantly enriched motifs in hypomethylated regions in cases versus controls were significantly upregulated in pancreatic cancer samples, we used a randomisation test with the ssGSEA score as the test statistic. For each sample, we computed the scores using the 85 TFs found significantly associated with hypomethylated motifs, and 1000 random sets of 85 TFs (the list of all human TFs was obtained from file TFCheckpoint_dovvnload_1 80515.txt under http://www.tfcheekpoint.org/data/); expression levels from 178 pancreatic adenocarcinoma patients on TCGA were used.

Figure 8A:
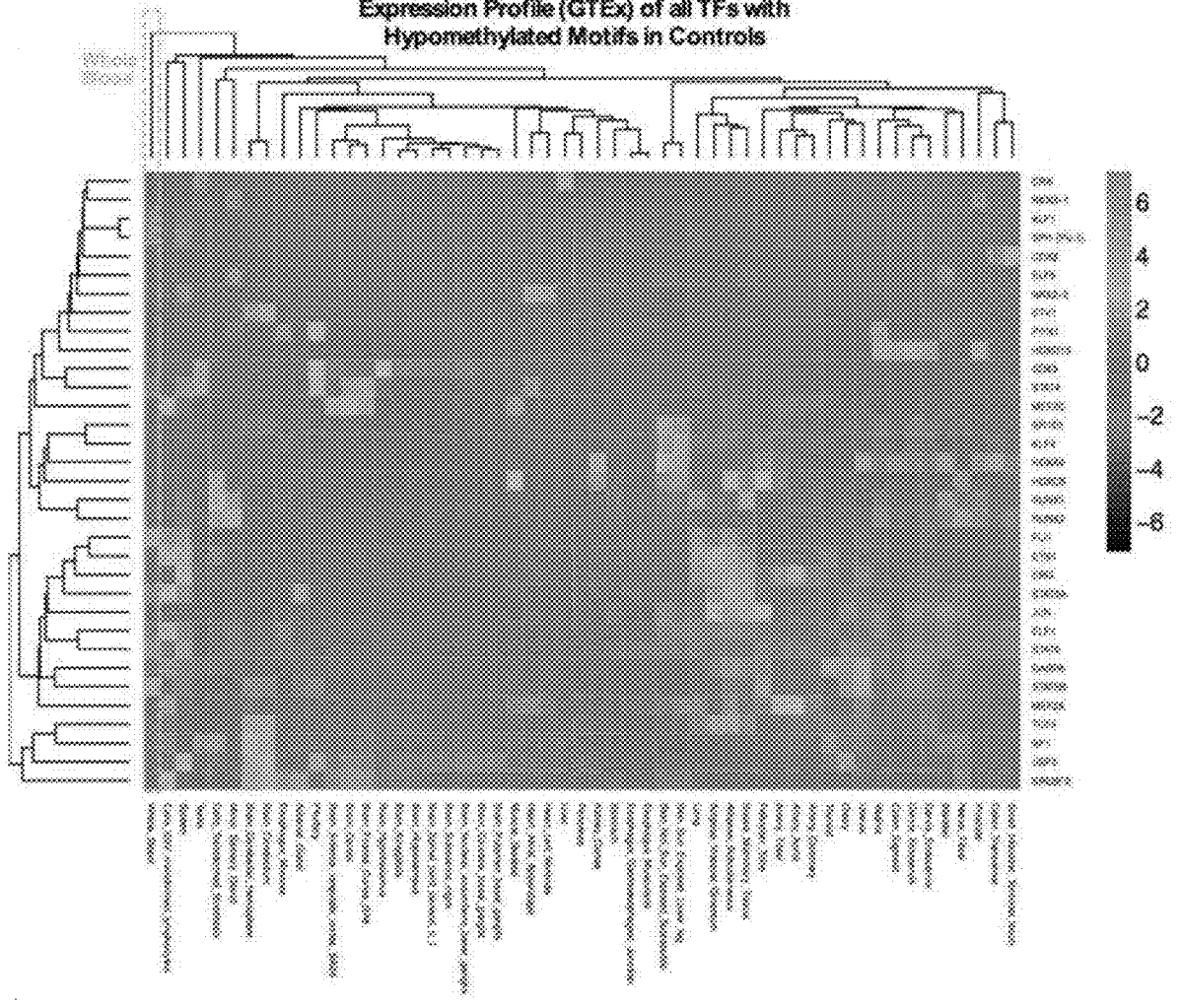
FIGS. 8A-8E show circulating cfDNA methylation profile can be used to identify transcription factors (TFs) footprints and infer active transcriptional networks in the tissue-of-origin.
Figure 8B:
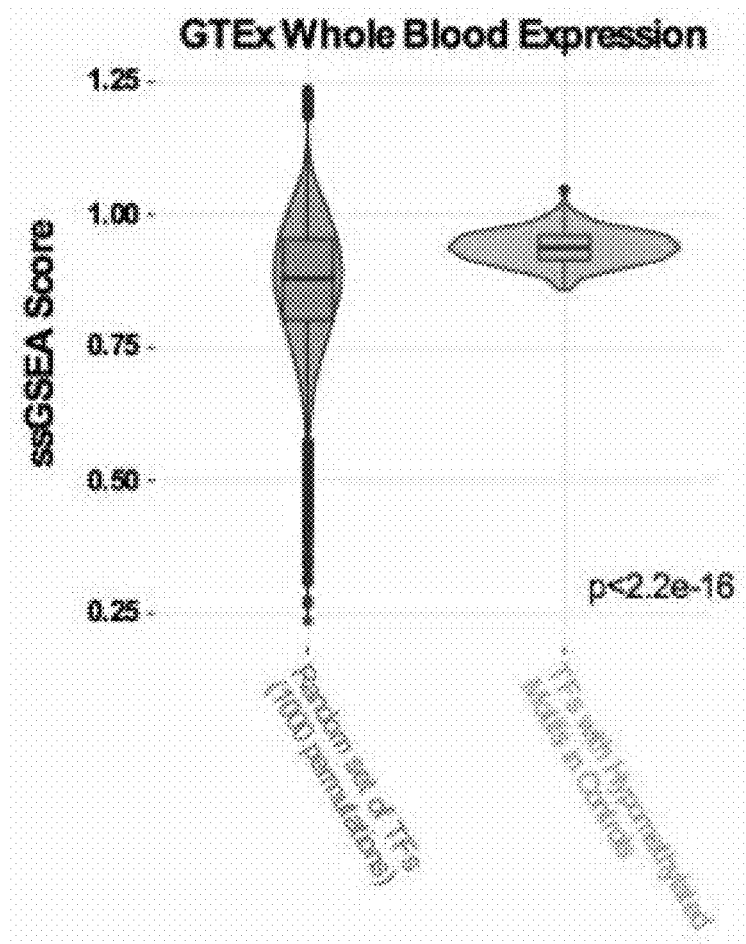
Figure 8C:
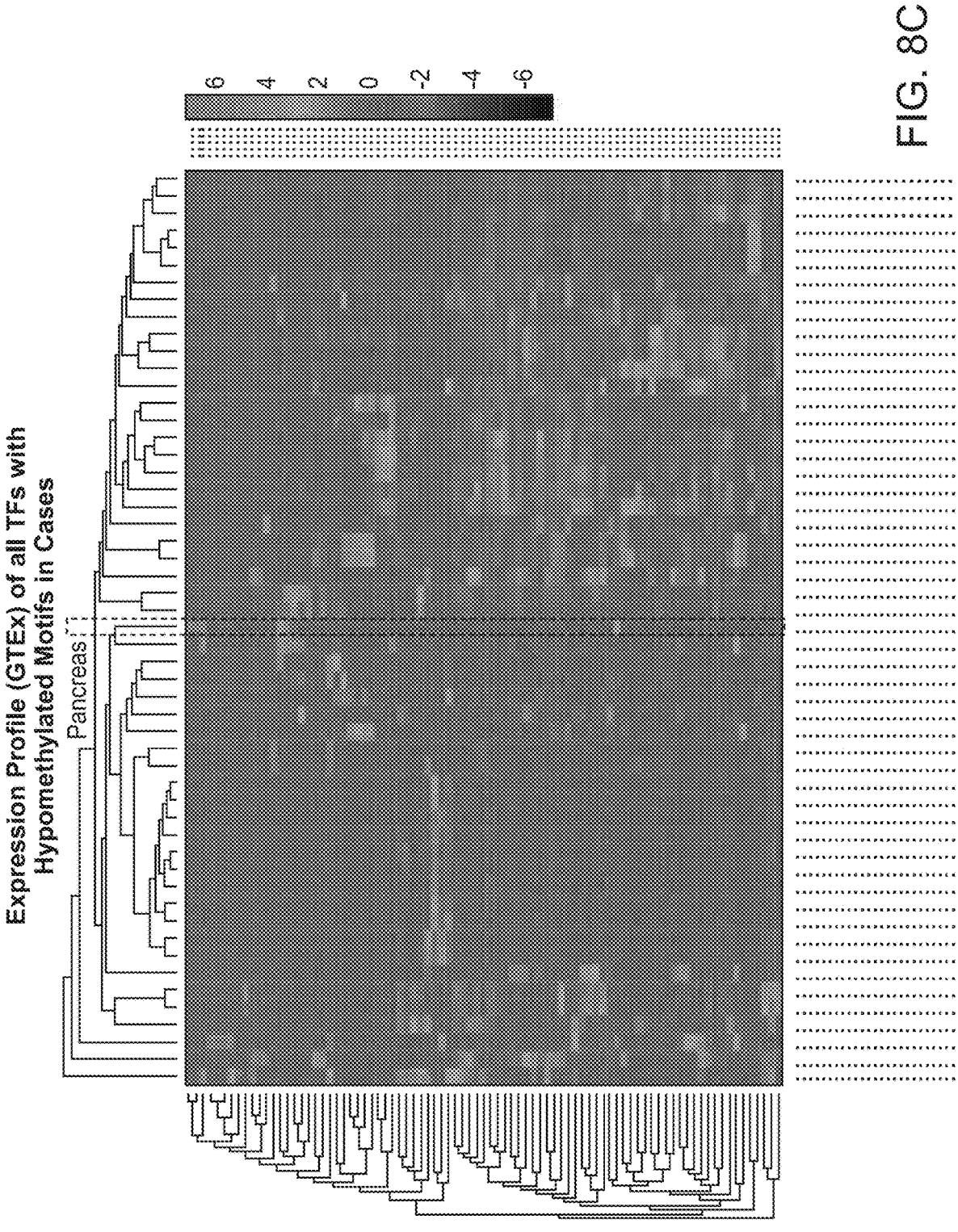
Figure 8D:
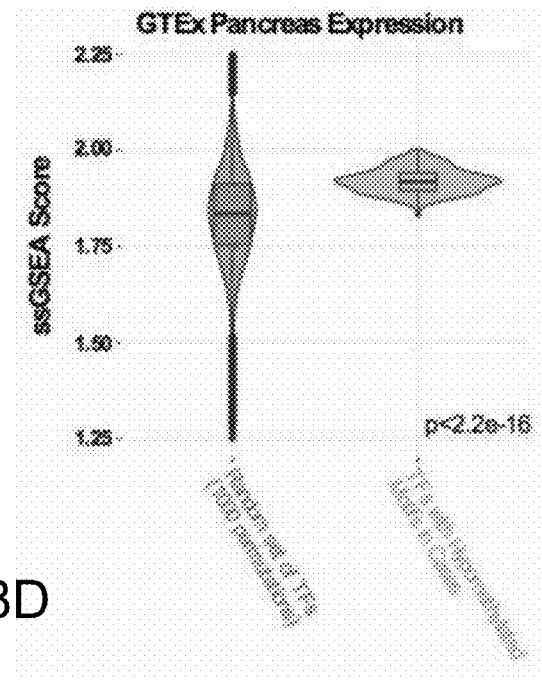
Figure 8E:
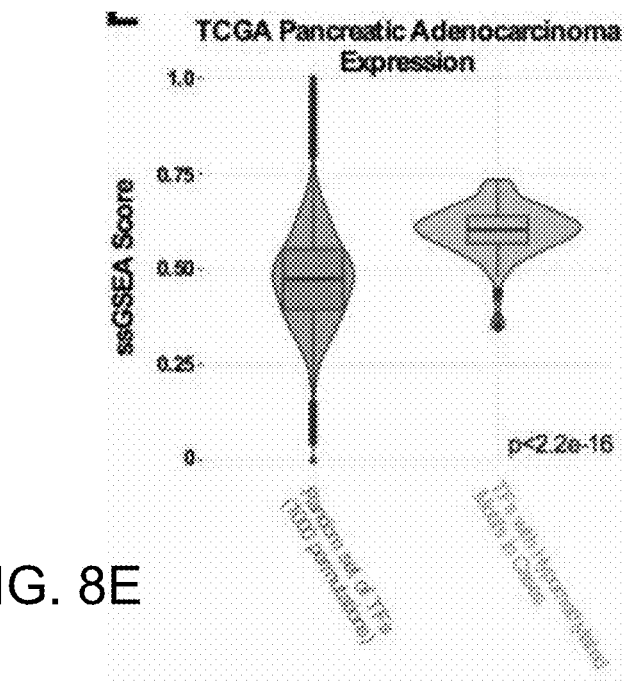

The distribution of these scores can be seen in the associated violin plots (FIG. 8E).

A Wilcoxon's Rank Sum test was then used to compare the random distribution versus the observed distribution, yielding a p-value<2.2e-16.

Figure 3A:
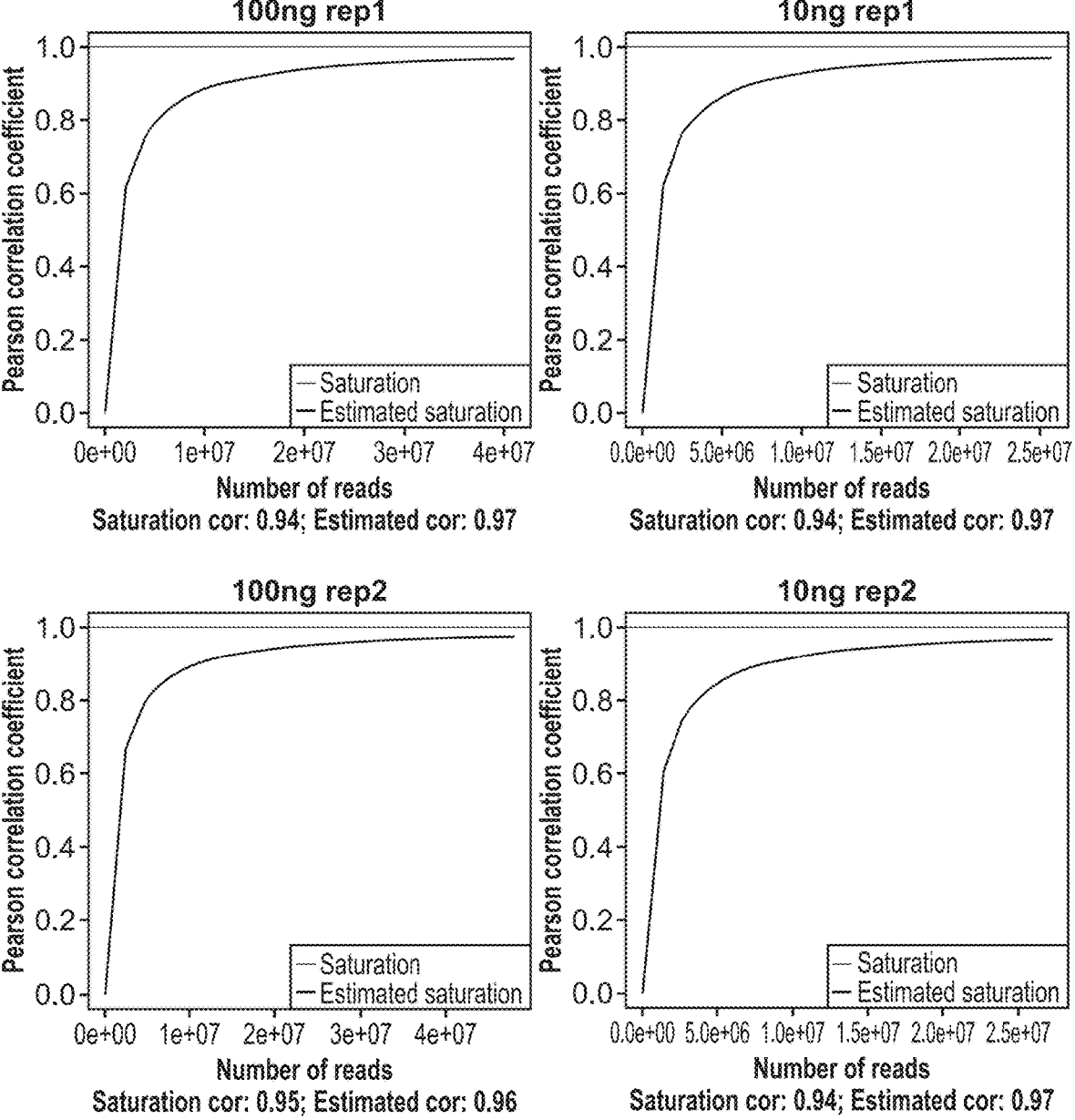
FIGS. 3A-3C show sequencing saturation analysis and quality controls.

The same analysis was done on the GTEx data with normal pancreas (FIG. 3D). The analysis was also repeated with TFs (n=33) whose motifs were identified as hypomethylated footprints in the plasma cfDNA from healthy donors, on the GTEx data with whole blood (FIG. 88).

Results/Discussion

A Genome-Wide Method Suitable for cfDNA Methylation Mapping

The cfMeDIP-seq method described here was developed through the modification of an existing low input MeDIP-seq protocol[17] that is robust down to 100 ng of input DNA.

However, the majority of plasma samples yield much less than 100 ng of DNA. To overcome this challenge, we added exogenous λ DNA (filler DNA) to the adapter-ligated of DNA library in order to artificially inflate the amount of starting DNA to 100 ng (FIG. 2). This minimizes the amount of non-specific binding by the antibody and also minimizes the amount of DNA lost due to binding to plasticware. The filler DNA consisted of amplicons similar in size to an adapter-ligated cfDNA library and was composed of unmethylated and in vitro methylated DNA at different CpG densities. The addition of this filler DNA also serves a practical use, as different patients will yield different amounts of cfDNA, allowing for the normalization of input DNA amount to 100 ng. This ensures that the downstream protocol remains exactly the same for all samples regardless of the amount of available cfDNA.

Figure 3B:
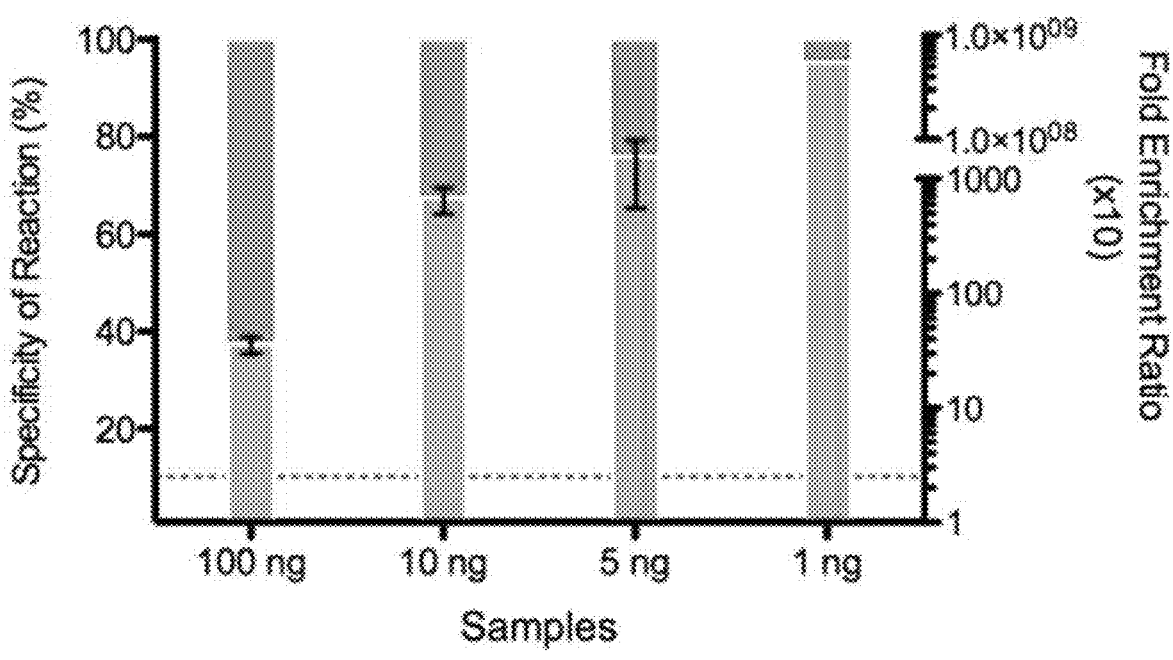

We first validated the cfMeDIP-seq protocol using DNA from human colorectal cancer cell line HCT116, sheared to a fragment size similar to that observed in cfDNA. HCT116 was chosen because of the availability of public DNA methylation data. We simultaneously performed the gold standard MeDIP-seg protocol" using 100 ng of sheared cell line DNA and the cfMeDIP-seq protocol using 10 ng. 5 ng, and 1 ng of the same sheared cell line DNA. This was performed in two biological replicates. For all the conditions, we obtained more than 99% specificity of the reaction (1-[recovery of spiked-in unmethylated control DNA over recovery of spiked-in methylated control DNA]), and a very high enrichment of a known methylated region over an unmethylated region (TSH2BO and GAPDH, respectively) (FIG. 3B).

Figure 3C:
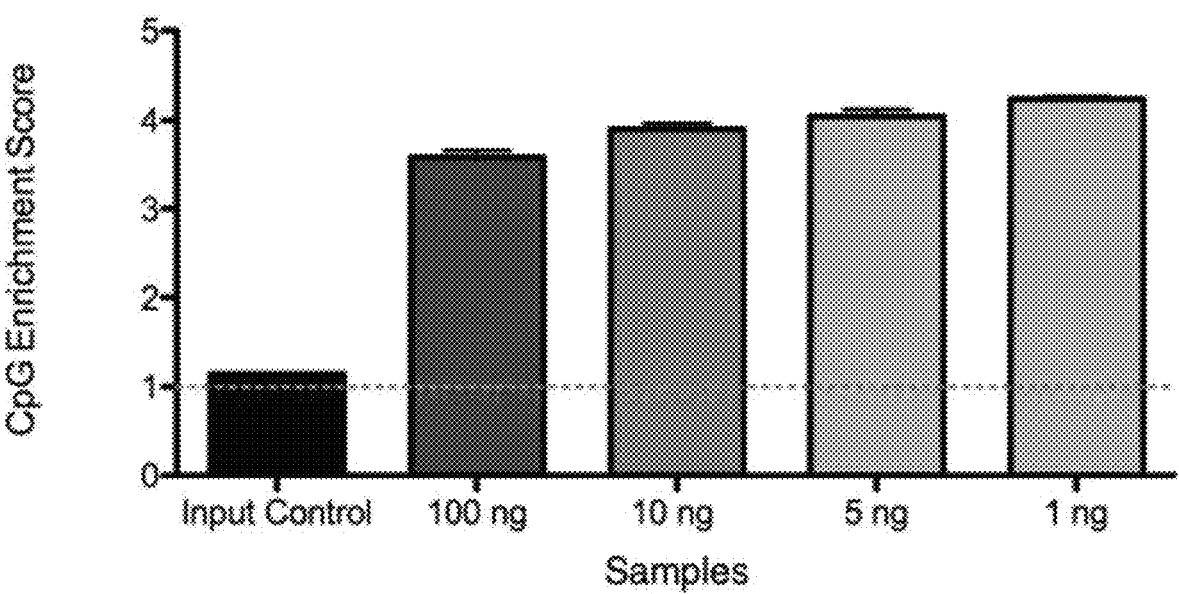
Figure 4A:
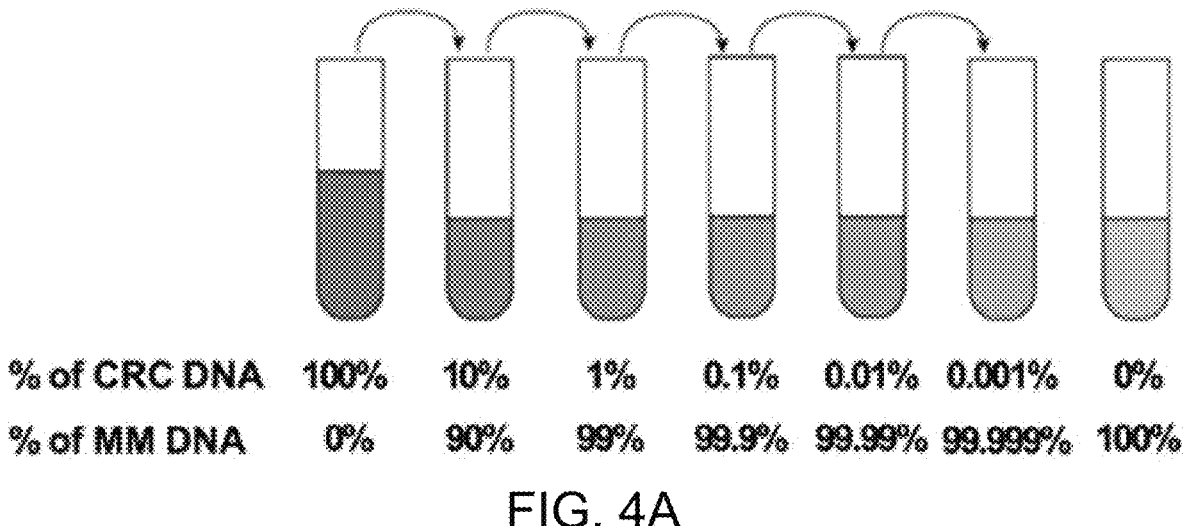
FIGS. 4A-4D show quality controls from cfMeDIP-seq from serial dilution.
Figure 4B:
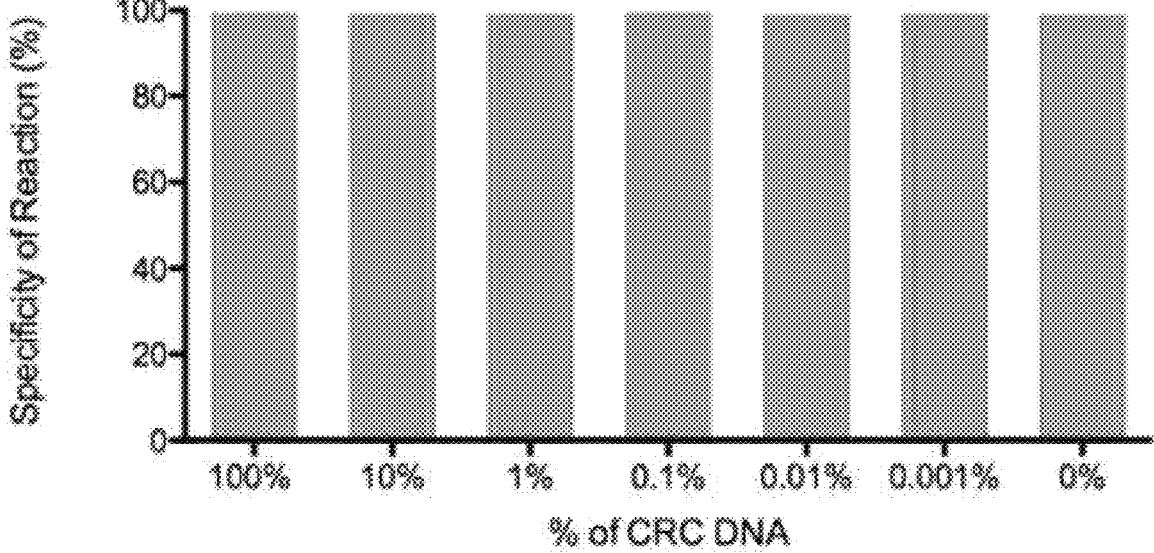
Figure 4C:
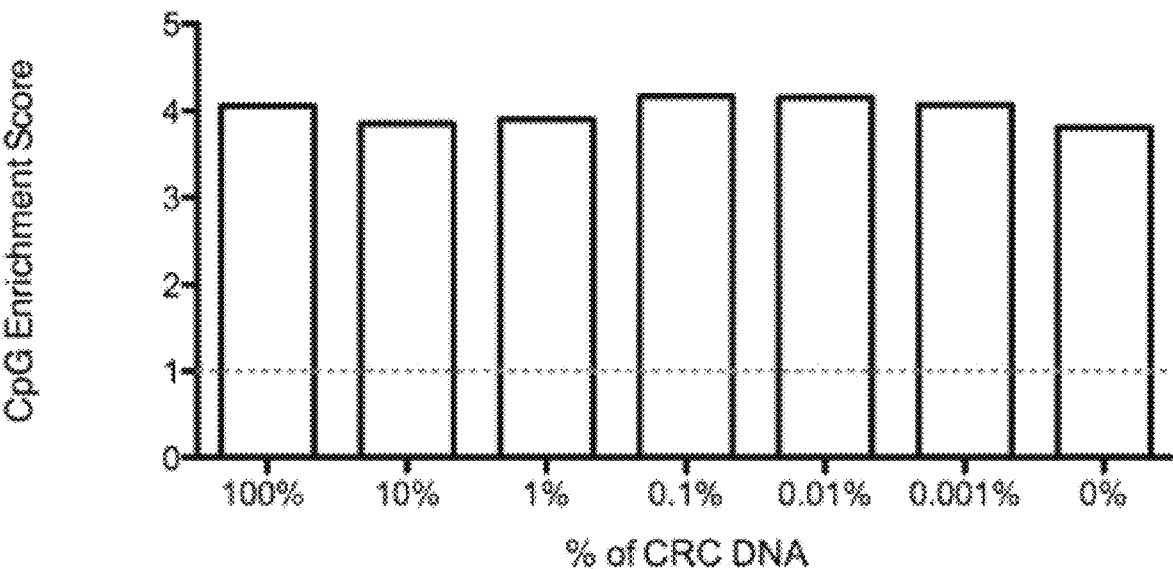
Figure 4D:
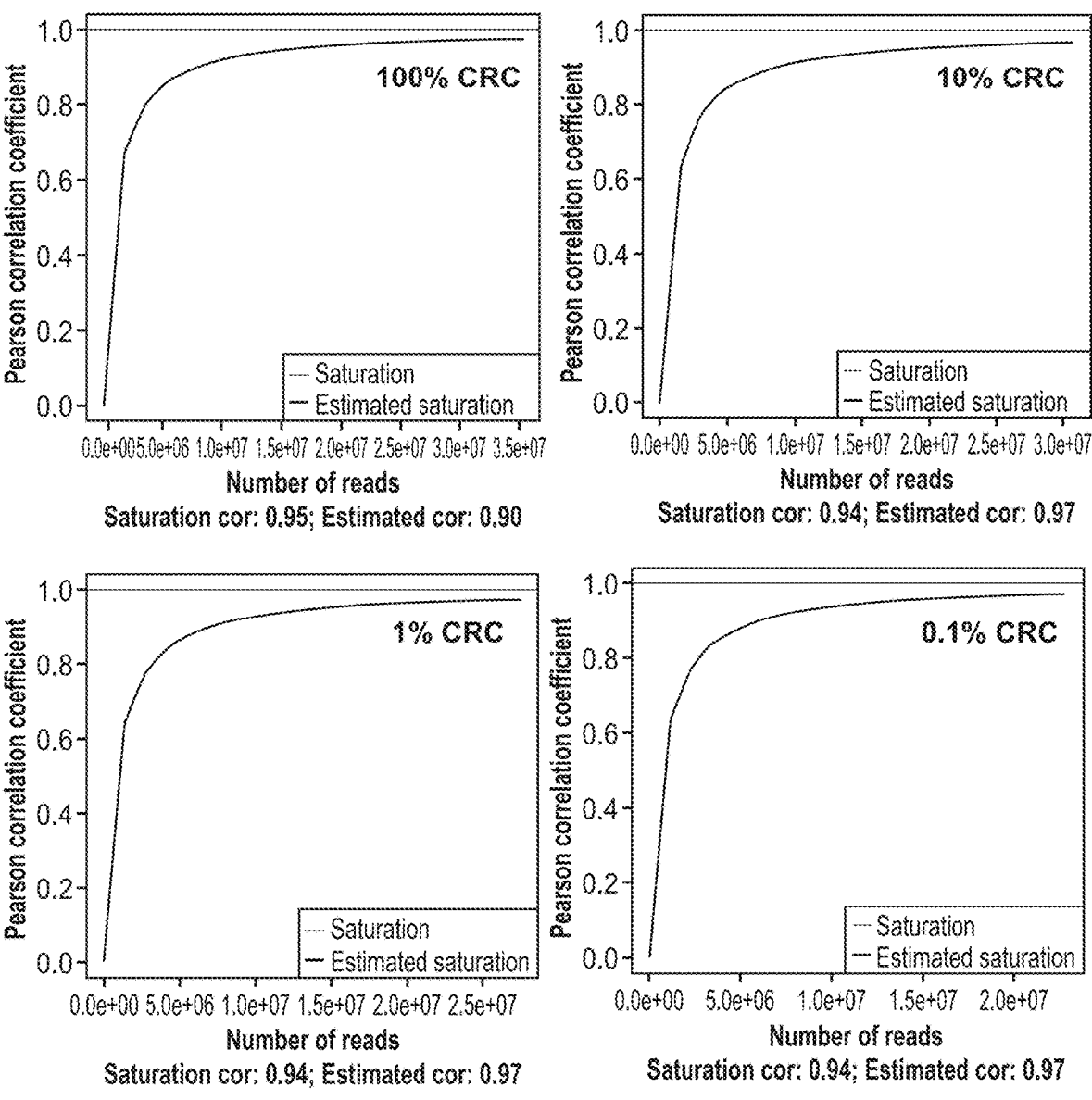
Figure 4D:
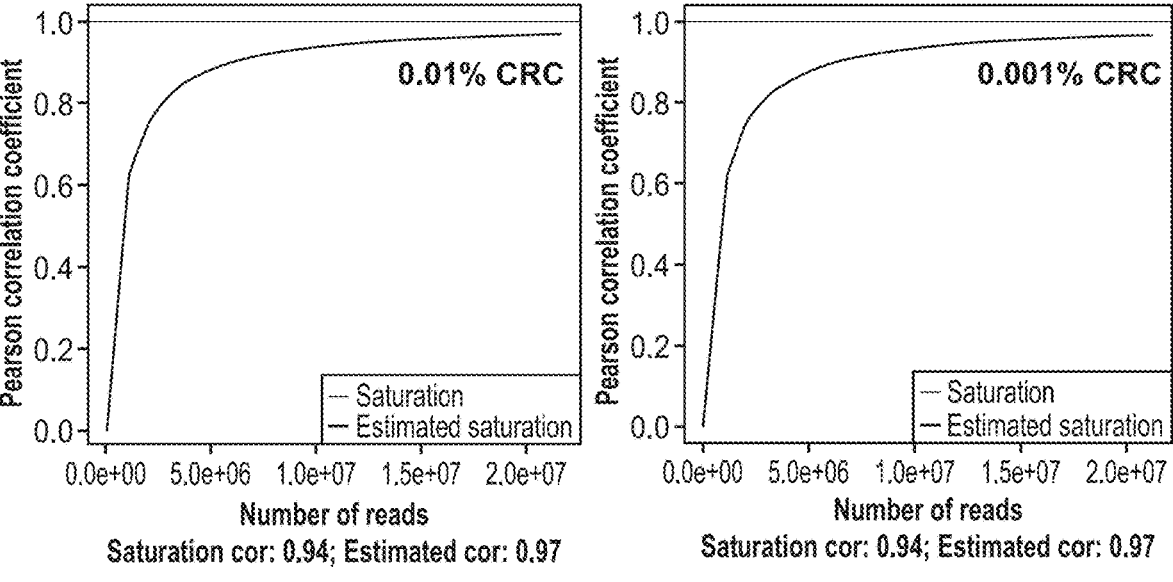
Figure 4D:
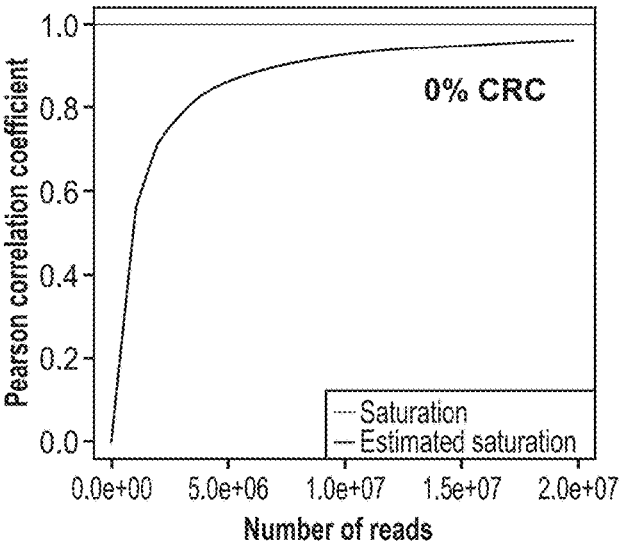

The libraries were sequenced to saturation (FIG. 3A) at around 30 to 70 million reads per library (Table 2). The raw reads were aligned to both the human genome and the λ genome, and found virtually no alignment was found to the A genome (Table 3A and 3B). Therefore, the addition of the exogenous λ DNA as filler DNA did not interfere with the generation of sequencing data. Finally, we calculate the CpG Enrichment Score as a quality control measure for the immunoprecipitation steps. All the libraries showed similar enrichment for CpGs while the input control, as expected, showed no enrichment (FIG. 3C), validating our immunoprecipitations even at extremely low inputs (1 ng).

Figure 1B:
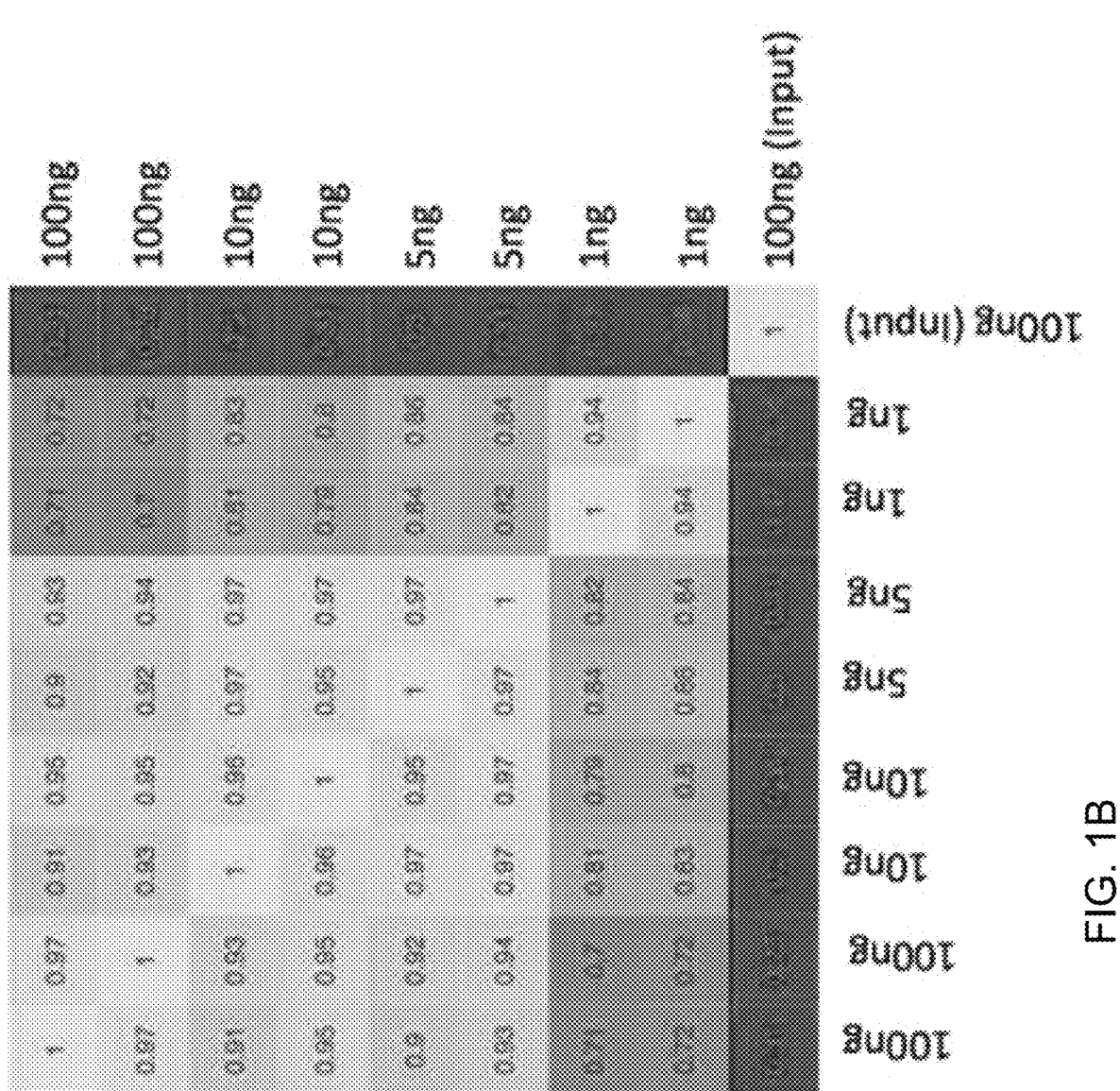
Figure 1C:
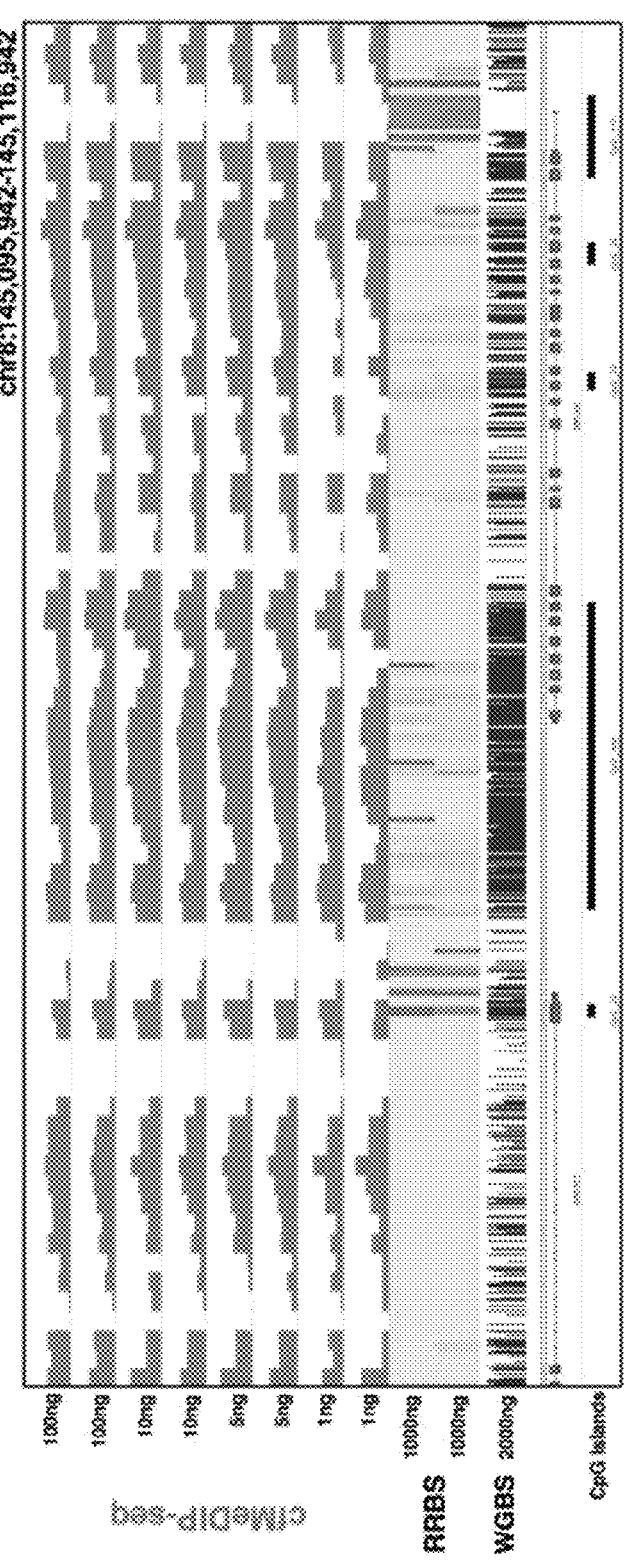

Genome-wide correlation estimates comparing different input DNA levels show that both MeDIP-seq (100 ng) and cfMeDIP-seq (10, 5, and 1 ng) methods were very robust, with Pearson correlation of at least 0.94 between any two biological replicates (FIG. 1B). The analysis also demonstrates that cfMeDIP-seq at 5 and 10 ng of input DNA can robustly recapitulate the methylation profile obtained by traditional MeDIP-seq at 100 ng (Pairwise Pearson correlation of at least 0.9) (FIG. 1B). The performance of cfMeDIP-seq at 1 ng of input DNA is reduced compared to MeDIP-seq at 100 ng but still shows a strong Pearson correlation at >0.7 (FIG. 1B). We also observed that the cfMeDIP-seq protocol recapitulates the DNA methylation profile of HCT116 using gold standard RRBS (Reduced Representation Bisulfite Sequencing) and WGBS (Whole-Genome Bisulfite Sequencing) (FIG. 1C). Altogether, our data suggests that cfMeDIP-seq is a robust protocol for genome-wide methylation mapping of fragmented and low input DNA material, such as circulating cfDNA.

cfMeDIP-Seo Displays High-Sensitivity for Detection of Tumor-Derived ctDNA

To evaluate the sensitivity of the cfMeDIP-seq protocol, we performed a serial dilution of Colorectal Cancer (CRC) HCT116 cell line DNA into a Multiple Myeloma (MM) MM1.5 cell line DNA, both sheared to mimic cfDNA sizes_

Figure 1D:
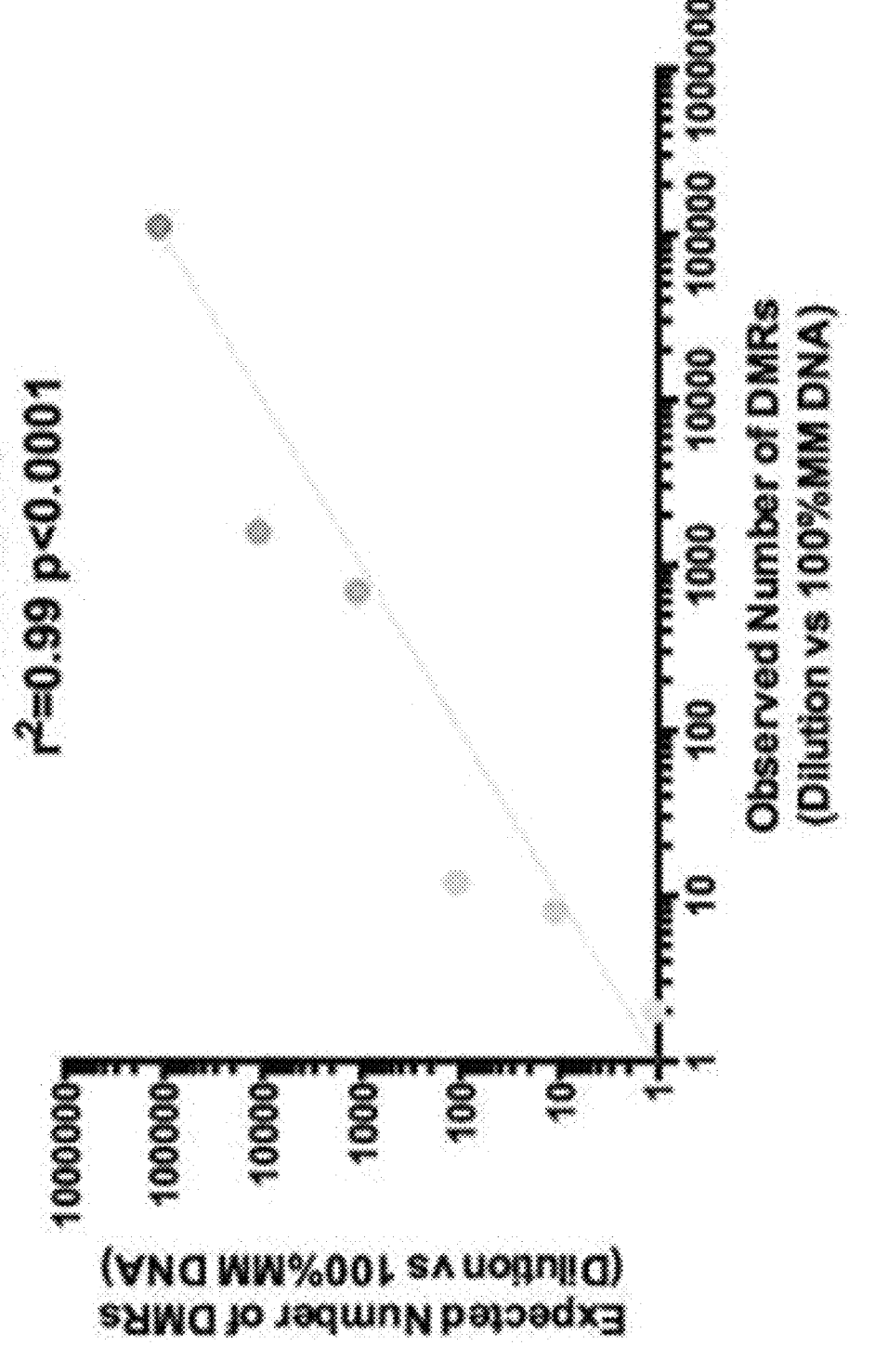
Figure 1E:
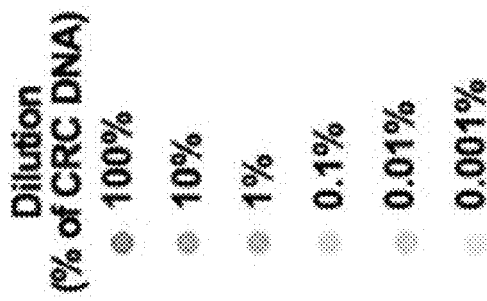
Figure 1E:
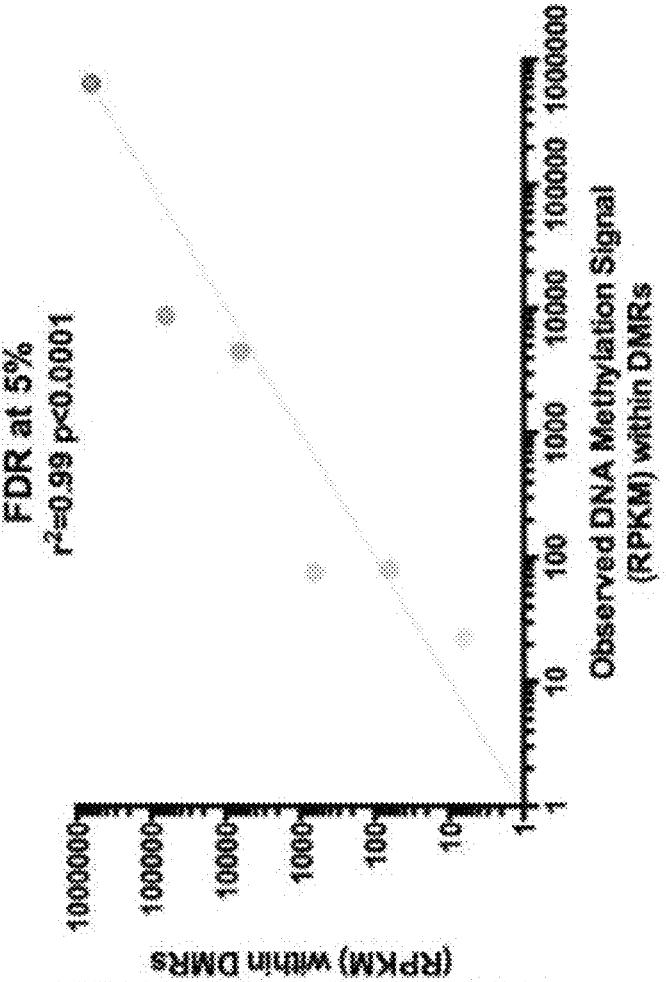
Figure 1F:
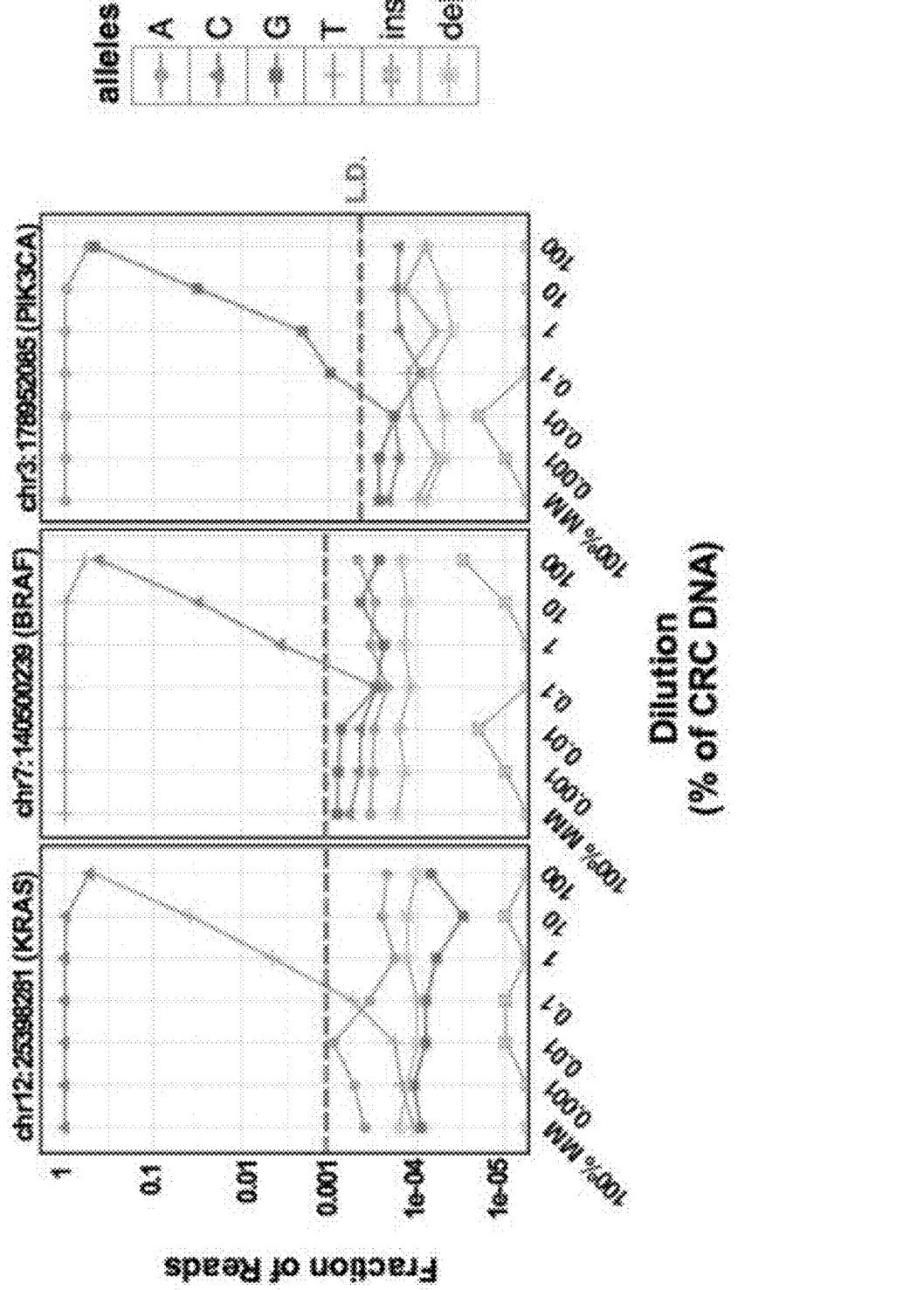

We diluted the CRC DNA from 100%, 10%, 1%, 0.1%, 0.01%, 0.001%, to 0% and performed cfMeDIP-seq on each of these dilutions (FIG. 4A-D). We also performed ultra-deep (10,000× median coverage) targeted sequencing for detection of three point mutations in the same samples. The observed number of DMRs identified at each CRC dilution point versus the pure MM DNA using a 5% False Discovery rate (FDR) threshold was almost perfectly linear ($r^2$=0.99, p<0.0001) with the expected number of DMRs based on the dilution factor (FIG. 1D) down to a 0.001% dilution. Moreover, the DNA methylation signal within these DMRs also shows almost perfect linearity ($r^2$=0.99, p<0.0001) between the observed versus expected signal (FIG. 1E). In comparison, beyond the 1% dilution, ultra-deep targeted sequencing could not reliably distinguish between the CRC-specific variants and the spurious variants due to PCR or sequencing-errors (FIG. 1F). Thus, cfMeDIP-seq displays excellent sensitivity for the detection of cancer-derived DNA, exceeding the performance of variant detection by ultra-deep targeted sequencing using a standard protocol.

Figure 1G:
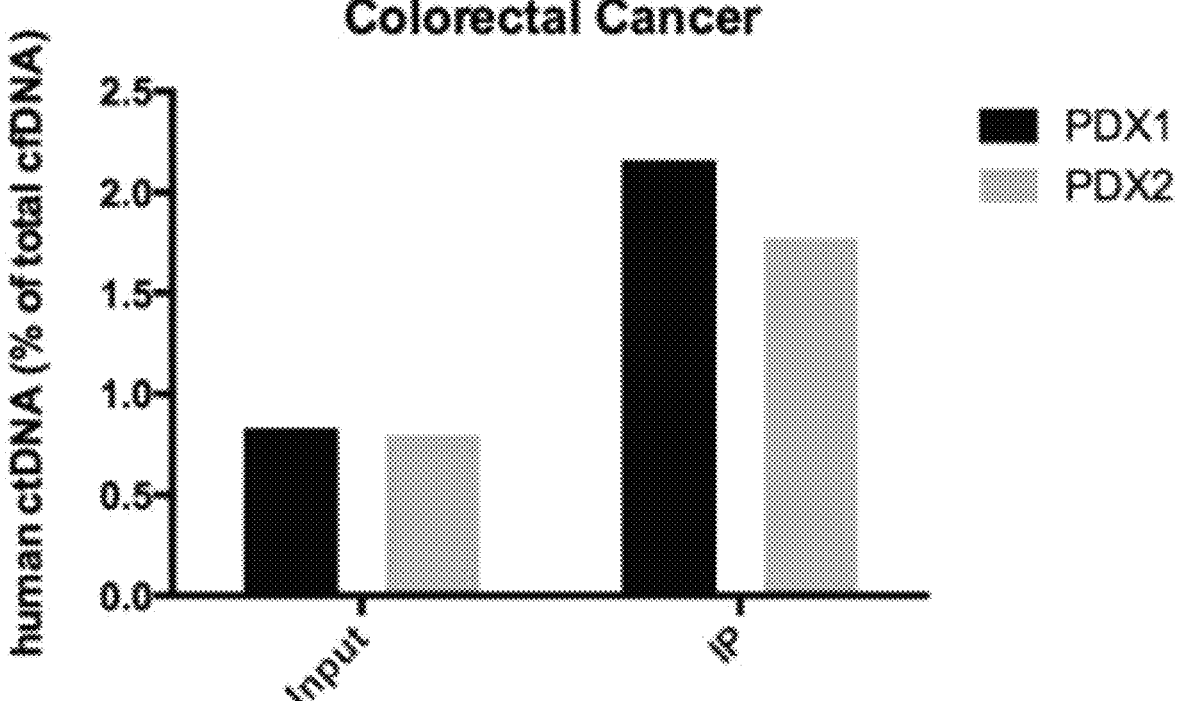

Cancer DNA is frequently hypermethylated at CpG-rich regional. Since cfMeDIP-seq specifically targets methylated CpG-rich sequences, we hypothesized that ctDNA would be preferentially enriched during the immunoprecipitation procedure. To test this, we generated patient-derived xenografts (PDXs) from two colorectal cancer patients and collected the mouse plasma. Tumor-derived human cfDNA was present at less than 1% frequency within the total cfDNA pool in the input samples and at 2-fold greater abundance following immunoprecipitation (FIG. 1G). These results suggest that through biased sequencing of ctDNA, the cfMeDIP procedure could further increase ctDNA detection sensitivity.

Methylome Analysis of Plasma cfDNA Distinguishes Early Stage Pancreatic Adenocarcinoma Patients from Healthy Donors We sought to investigate whether methylome analysis of plasma cfDNA could be used to detect ctDNA in early stage cancer. We performed the methylome analysis in the pre-surgery plasma of 24 early stage pancreatic cancer patients (cases) and 24 age and sex-matched healthy donors (controls) (Tables 4A, 4B and 5). For each patient, laser-capture microdissected (LCM) tumor samples with high tumor purity and normal tissue samples were examined. cfMeDIP-seq was performed on the circulating cfDNA and RRBS on the tumor and normal tissues (FIG. 5A and FIG. 6, Tables BA and 81a). Using a t-test and Benjamini-Hochberg correction for multiple testing, we obtained 38,085 DMRs (p<0.01, q<0.1) between the cases and controls cfDNA (FIG. 5B-C).

Figure 7A:
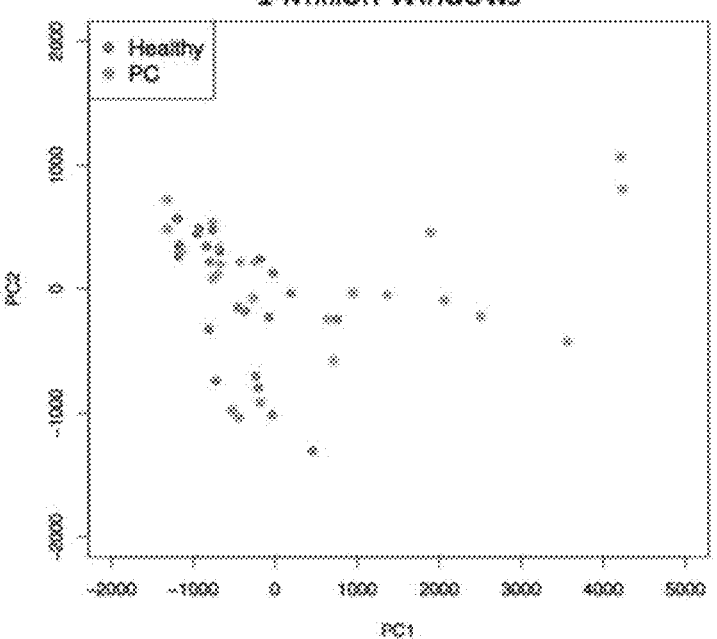
FIG. 7A shows PCA on the 48 plasma cfDNA methylation from healthy donors and early stage pancreatic adenocarcinoma patients using the top million most variable genome-wide windows. For each window, variability was calculated using the MAD (Mean Absolute Deviation) metric, which is a robust measurement that returns the median of the absolute deviations from the data's median value; in this case, the data is the RPKM values across all the 48 samples for a given window. PC1 versus PC2 (left) and PC1 versus PC3 (right) are shown.
Figure 7A:
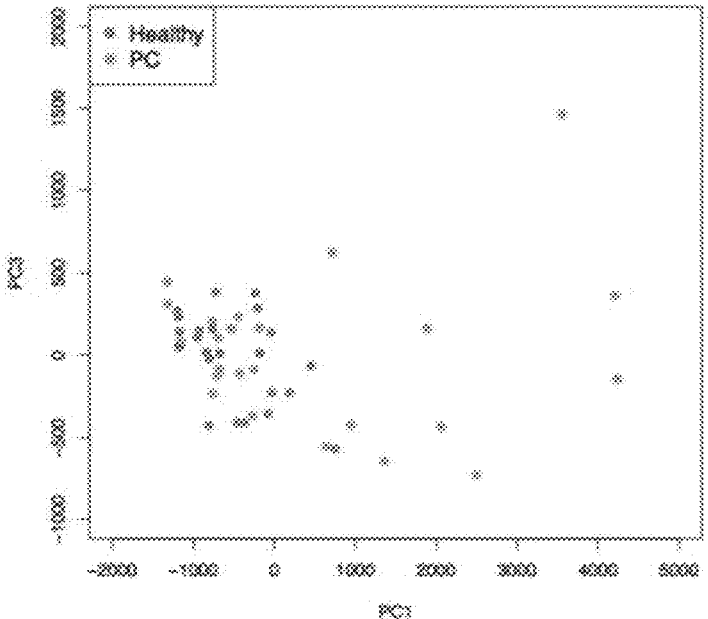
Figure 7B:
FIG. 7B shows percentage of variance for each principal component.
Figure 7B:
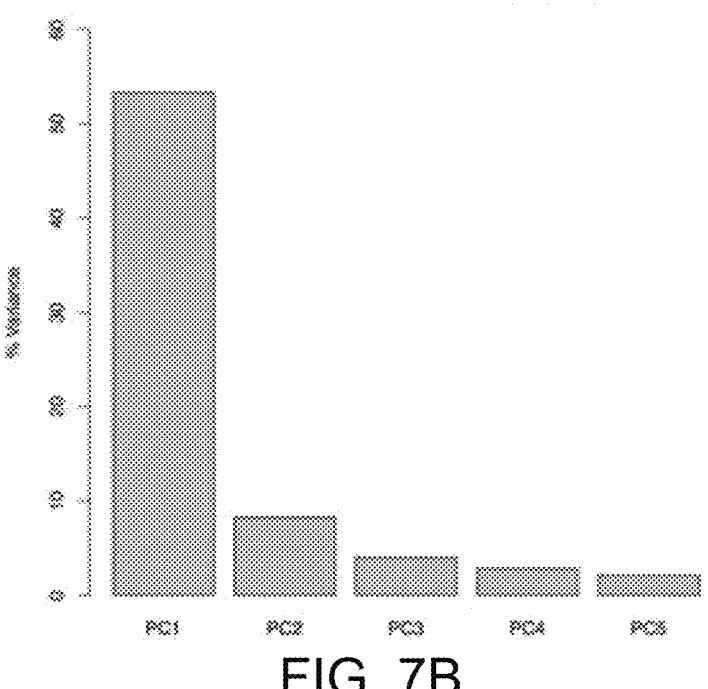
Figure 7C:
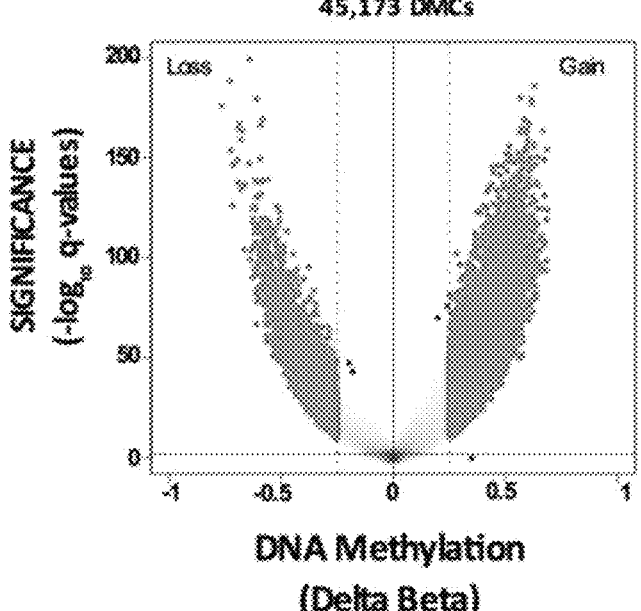
FIG. 7C shows volcano plot for tumor versus normal LCM tissue from pancreatic adenocarcinoma patients using RRBS. Total numbers of DMCs (Differentially Methylated CpGs) identified are listed. Red dots indicate the windows that reached significance after correction for multiple tests and having absolute methylation difference (absolute delta beta)>0.25.

In order to evaluate whether the differences in the cfDNA methylation profiles between cases and controls were due to the presence of ctDNA, the DNA methylation patterns of the primary tumors and normal tissue, obtained from the same patients after surgical resection, were mapped using RRBS. We identified 45,173 differentially methylated CpGs (DMCs) between tumors (n=24) versus normal (n=24) tissues (FIG. 7A-C).

The utility of cfDNA methylation profiles in recapitulating methylation profiles of their original tumor was tested by examining combinations of DMCs in tumors and DMRs in cfDNA (hypermethylated in both. hypomethylated in both. hypermethylated in one and hypomethylated in the other) for enrichment relative to the background. We observed significant enrichment for tumor-specific hypermethyated and hypomethylated sites in the concordant direction in cfDNA, while tumor-specific hypermethylated sites were under-rep-

US 12,655,417 B2

Figure 5D:
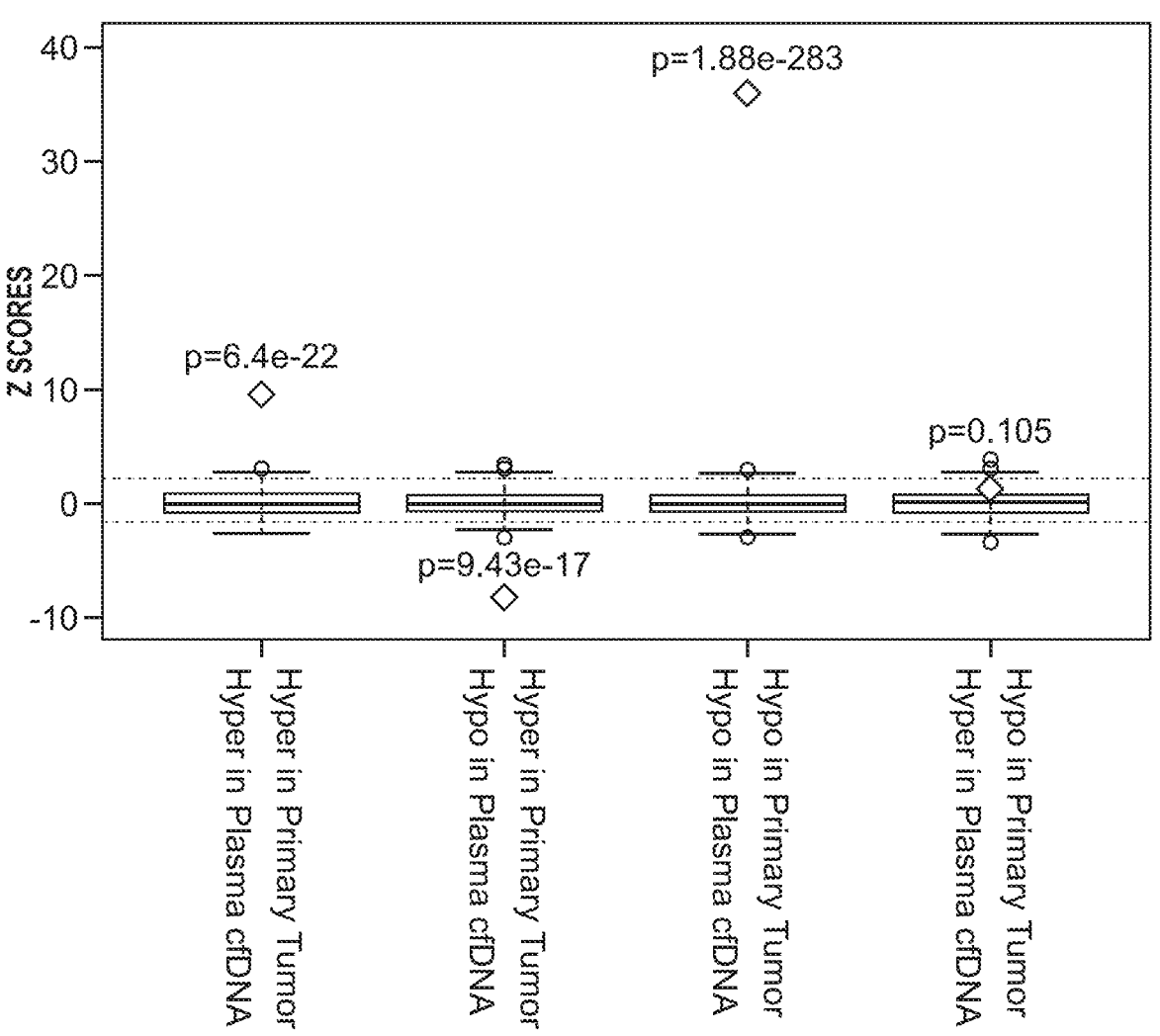
Figure 5E:
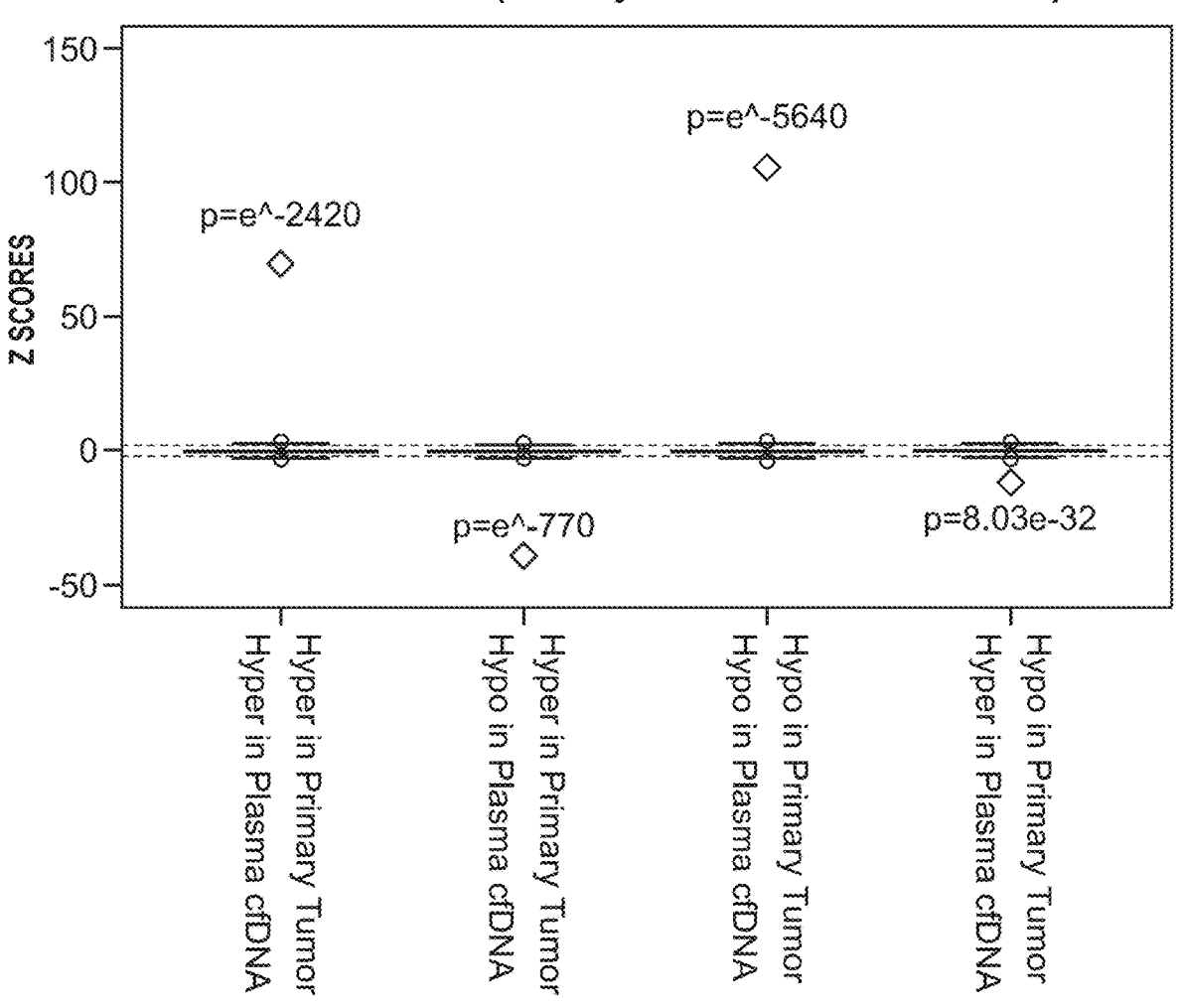
Figure 6A:
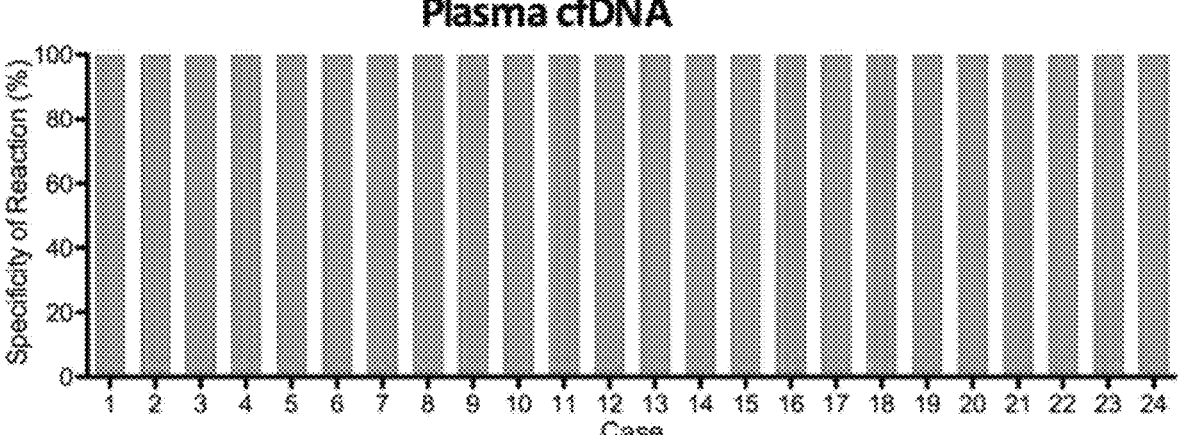
FIGS. 6A-6D shows quality controls for cfMeDIP-seq from circulating cfDNA from pancreatic adenocarcinoma patients (cases) and healthy donors (controls).
Figure 6B:
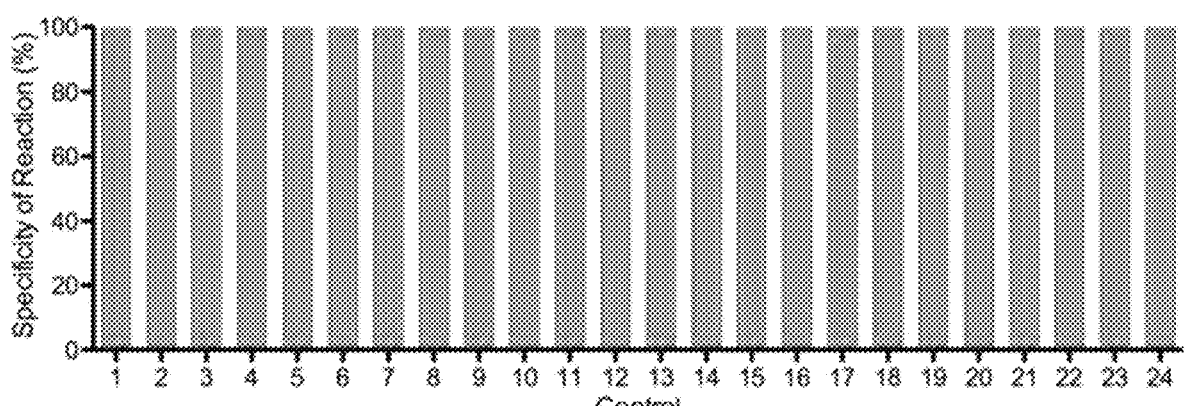
Figure 6C:
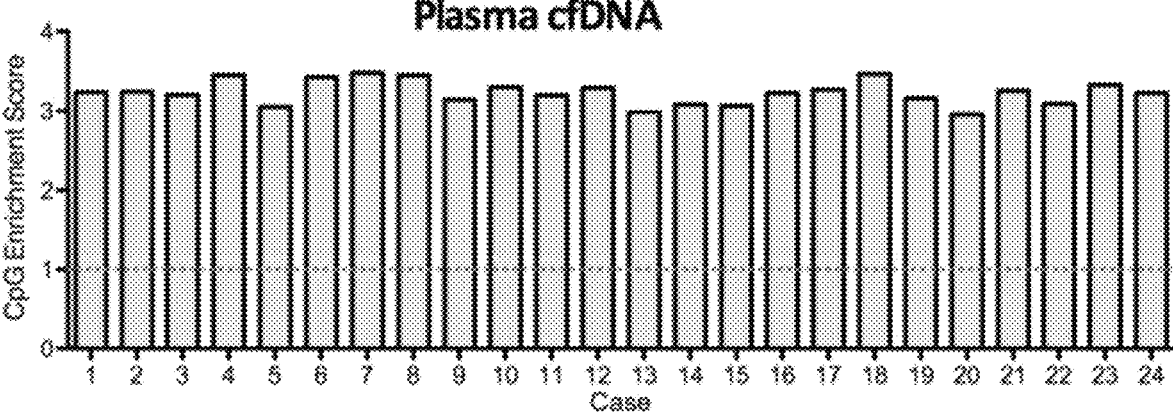
Figure 6D:
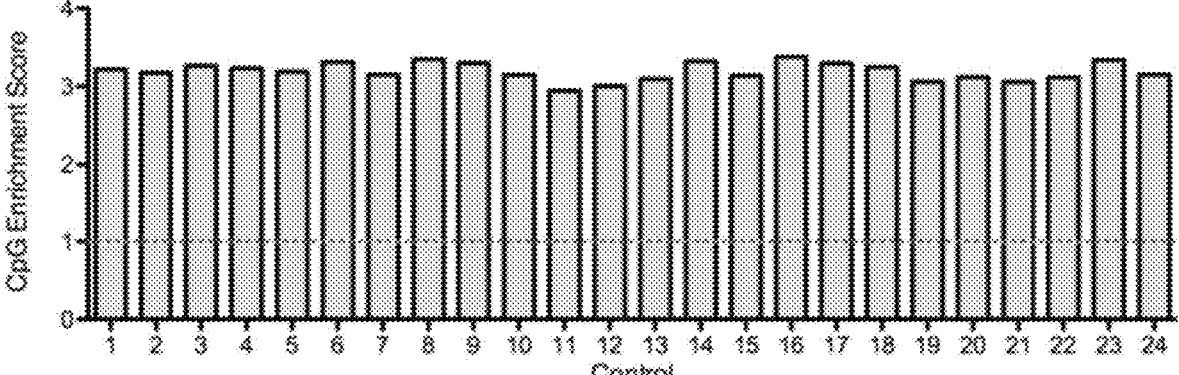
Figure 7D:
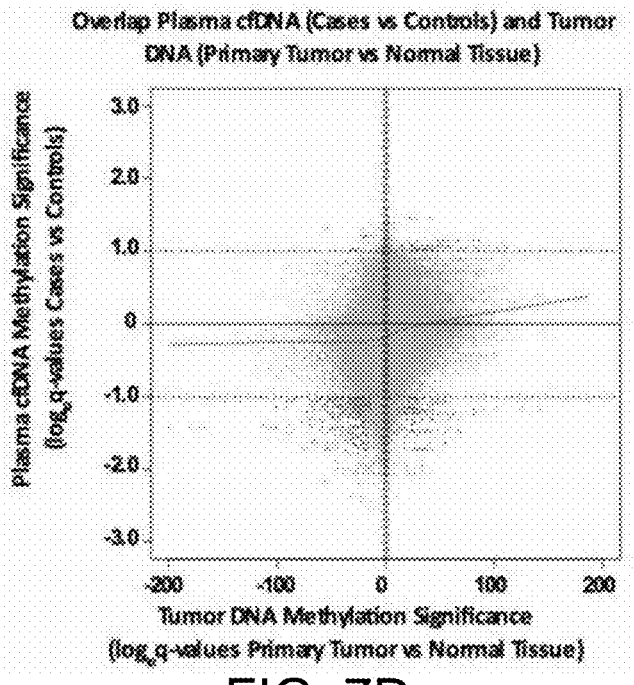
FIG. 7D shows the scatter-plot showing the significance of the DNA methylation difference for each overlapping window. X-axis shows the log 10 q values for the primary pancreatic adenocarcinoma tumor versus normal tissue from the RRBS data. If the region is hypermethylated in the tumor, the significance is showed on a positive scale. Hypomethylated regions are shown on a negative scale. Y-axis shows the log 10 q values for the plasma cfDNA methylation from pancreatic adenocarcinoma patients versus healthy donors from the cfMeDIP-seq data. Blue dots are significant in both. Red line shows the trend line.
Figure 7E:
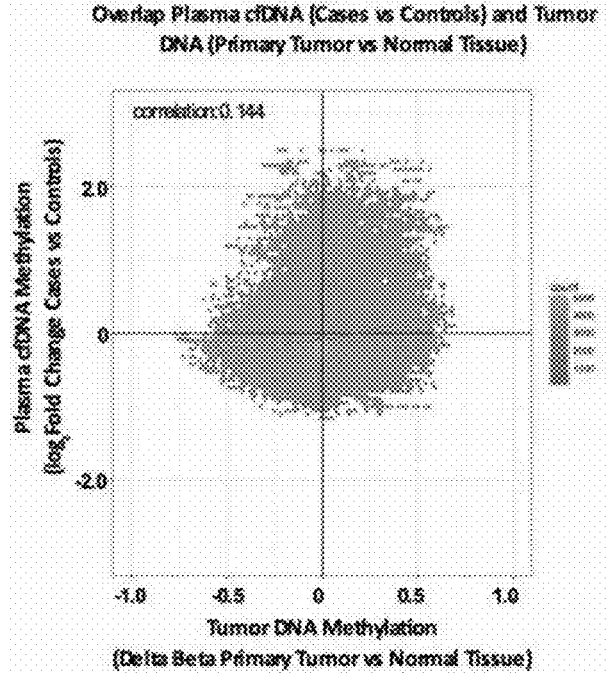
FIG. 7E shows scatter-plot showing the DNA methylation difference for each overlapping window. X-axis shows the DNA methylation difference for the primary pancreatic adenocarcinoma tumor versus normal tissue from the RRBS data. Y-axis shows the DNA methylation difference for the plasma cfDNA methylation from pancreatic adenocarcinoma patients versus healthy donors from the cfMeDIP-seq data. Blue line shows the trend line.

17 resented in cfDNA hypomethylated DMRs (FIG. 5D). Indeed, there is a correlation between the DNA methylation status for a given region in the tumor and the methylation profile in the plasma cfDNA (FIG. 7D-E).

Figure 7F:
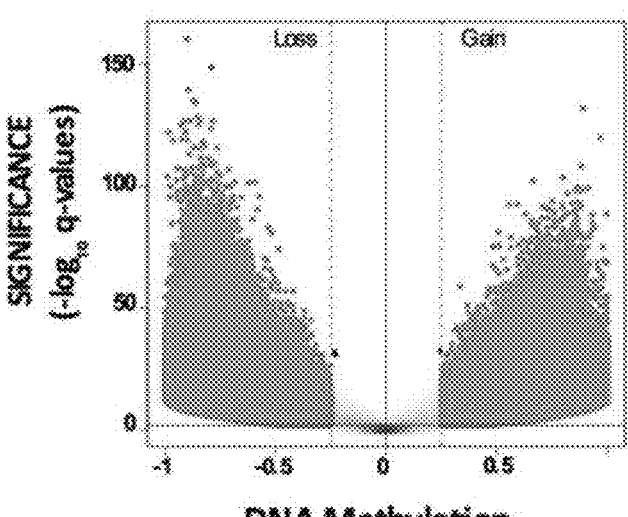
FIG. 7F shows volcano plot for LCM pancreatic adenocarcinoma tissue versus normal PBMCs using RRBS. Total numbers of DMCs (Differentially Methylated CpGs) identified are listed. Red dots indicate the windows that reached significance after correction for multiple tests and having absolute methylation difference (absolute delta beta)>0.25.
Figure 7G:
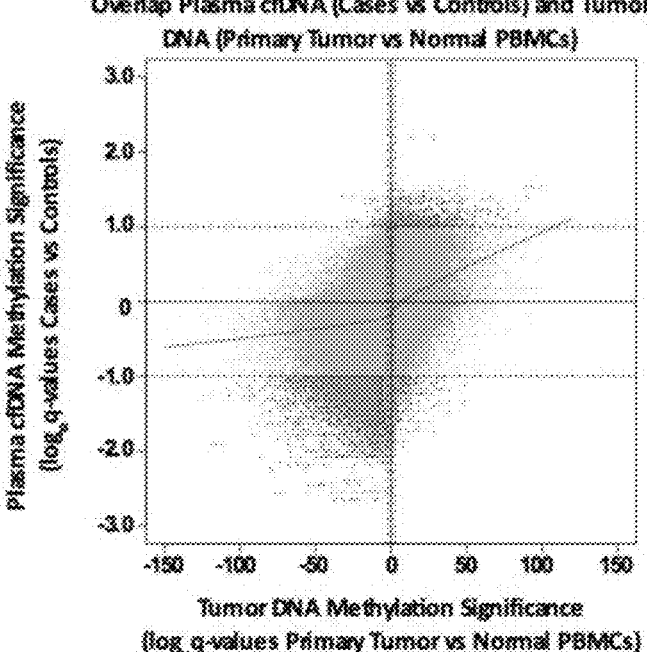
FIG. 7G shows Scatter-plot showing the significance of the DNA methylation difference for each overlapping window. X-axis shows the log 10 q values for the primary pancreatic adenocarcinoma tumor versus normal PBMCs from the RRBS data. If the region is hypermethylated in the tumor, the significance is showed on a positive scale. Hypomethylated regions are shown on a negative scale. Y-axis shows the log 10 q values for the plasma cfDNA methylation from pancreatic adenocarcinoma patients versus healthy donors from the cfMeDIP-seq data. Blue dots are significant in both Red line shows the trend line.
Figure 7H:
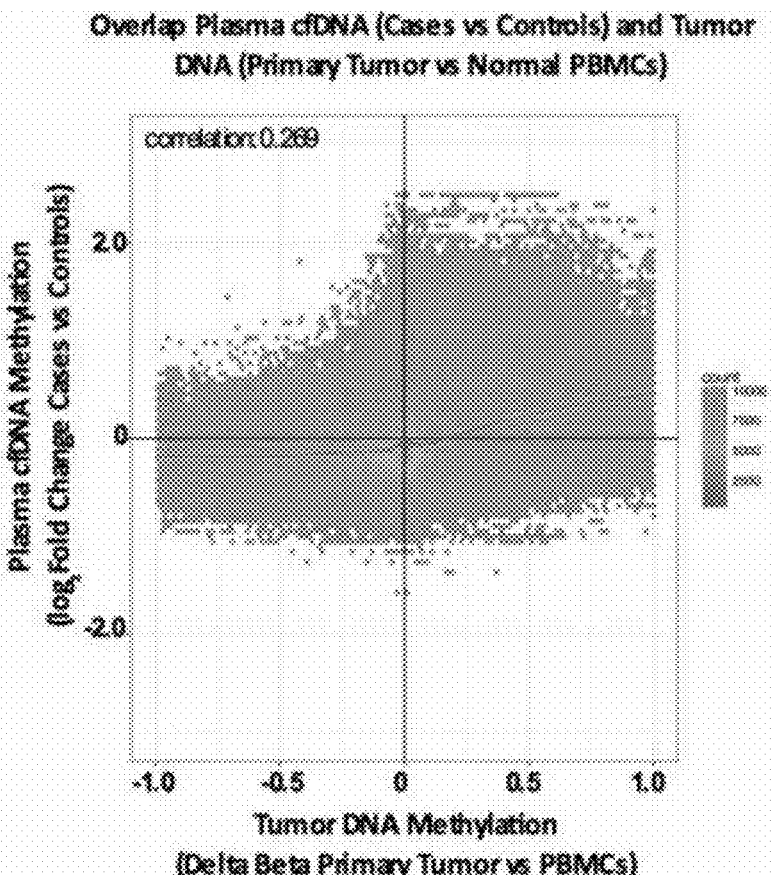
FIG. 7H shows scatter-plot showing the DNA methylation difference for each overlapping window. X-axis shows the DNA methylation difference for the primary pancreatic adenocarcinoma tumor versus normal PBMCs from the RRBS data. Y-axis shows the DNA methylation difference for the plasma cfDNA methylation from pancreatic adenocarcinoma patients versus healthy donors from the cfMeDIP-seq data.

Finally, since the majority of the plasma cfDNA molecules in cancer patients, especially at early stage, are non-tumor-derived and likely released from blood cells[14], we evaluated the DNA methylation differences between the pancreatic adenocarcinoma tumor tissue against normal Peripheral Blood Mononuclear Cells (PBMCs). We identified 313,683 DMCs between tumors (n=24) versus PBMCs (n=5) (FIG. 7F). We observed significant enrichment for tumor-specific hypermethyated and hypomethylated sites in the concordant direction in cfDNA, while tumor-specific hypermethylated sites were under-represented in cfDNA hypomethylated DMRs (FIG. 5E). Again, there is a correlation between the DNA methylation status for a given region in the tumor and the methylation profile in the plasma cfDNA (FIG. 7G-H).

Altogether, these results suggest that the difference in the circulating cfDNA methylation profile between cases and controls was largely due to the presence of tumor-derived DNA in the circulating system (FIGS. 5D-E and FIGS. 7C-H).

Plasma cfDNA Methylomes Permit Inference of Tumor-Associated Active Transcription Factor Networks Since the DMRs between cases and controls were highly enriched for tumor-derived DMRs (FIG. 5D-E), we hypothesized that cfDNA methylomes would reveal enrichment for motifs related to tumor-specific or tissue-related active transcription factors. These cfDNA methylomes could be used to infer active transcriptional networks in the tissue-of-origin of these DNA molecules. To infer the active transcriptional networks, we investigated whether the DMRs in cfDNA could uncover enrichment for transcription factor (TF) footprints, as the majority of TFs display variable binding based on DNA-methylation states of target sequences[28]. Motif analysis was carried out with the HOMER software[28] on the hypomethylated DMRs[2o], separately for healthy donors (Figure BA) and pancreatic cancer patients (FIG. 8C), to uncover potential TF footprints.

We identified 33 motifs as hypomethylated footprints in the healthy donors as compared to the pancreatic adenocarcinoma cases and 85 motifs as hypomethylated footprints in the pancreatic adenocarcinoma cases as compared to the healthy donors.

Out of the 33 motifs identified as hypomethylated footprints in the healthy donors, we identified several TFs preferentially expressed in the hematopoietic lineage, including PU.1, Fli1, STAT5B, and KLF1 (FIG. 8A-B).

Similarly, out of the 85 motifs identified as hypomethylated footprints in the pancreatic adenocarcinoma cases, we identified several IFs preferentially expressed in the pancreas, including RBPJL, PTF1a, Onecut1 (HNFG), and NR5A2 (FIG. 8C-D). The TF motifs identified as hypomethylated footprints in the pancreatic adenocarcinoma cases were also frequently overexpressed in pancreatic adenocarcinoma patients from TCOA (FIG. 8E). Furthermore, we were able to identify several hypomethylated footprints in the pancreatic adenocarcinoma cases that correspond to TFs previously identified as drivers of each molecular subtypes of pancreatic cancer[24]. These included c-MYC and HIFI a (Squamous subtype drivers), NR5A2, MAFA, RBPJL, and NEUROD1 (ADEX drivers) and finally FOXA2 and HNF4A (pancreatic progenitor subtype).

Altogether, these results suggest that methylome analysis of circulating cfDNA can be used to infer active transcriptional networks within the tumor based on the differentially methylated IF footprints and potentially identify systemic shifts in immune cell populations between healthy donors and cancer patients.

Here we present a novel genome-wide DNA methylation method suitable for ultra-low input and fragmented DNA, such as circulating cell-free DNA. We were able to show that cfMeD11[3]-seg is very robust at low level of input DNA and allows for rapid generation of libraries. Moreover, since our method relies on the enrichment of methylated DNA, to sequence the libraries to saturation required only around 30 to 70 million reads per library, making whole genome sequencing unnecessary and significantly decreasing the associated cost. The rapid turnaround time in addition to the relatively small cost may allow for a quick translation of cfMeDIP-seq to a clinical setting.

Moreover, since cfMeDIP-seq relies on epigenetic, rather than genomic information, it could potentially be used to non-invasively monitor tissue damage in a broad set of non-malignant diseases. For instance, it could be used to monitor immune response to an infection or after cancer immunotherapy; it could be used to monitor heart DNA in the circulation after myocardial infarction or brain DNA during early stages of neurodegenerative diseases.

Finally, in the context of oncology, multiple cancer types have shown to have clinically distinct subgroups. These subgroups can be stratified by different DNA methylation profiles with prognostic value in glioblastoma[3], ependymomas[4], colorectal, breast, and pancreatic cancer[24] among many other cancer types. Recent data suggests that pancreatic cancer patients can be stratified into four subgroups driven by several mechanisms[24]: squamous, pancreatic progenitor, immunogenic and aberrantly differentiated endocrine exocrine (ADEX). In the circulating cfDNA methylome of pancreatic cancer patients, we were able to identify the hypomethylated footprints from TFs that drive these subtypes. For instance, we identified MYC and HIFI alpha (Hypoxia-inducible factor 1-alpha), two pathways enriched in the squamous subtype'. We were also able to identify HNF4A and FOXA2; two TFs enriched in the progenitor subtype[24]. Finally, we were able to identify NR5A2, RBPJL, and MAFA, three TFs enriched in the ADEX subtype. This suggests that cfMeDIP-seq could also be used as a biomarker to stratify cancer patients with a minimally invasive approach.

The invention has been described with regard to specific embodiments. It will be apparent to a person skilled in the art that variations and changes may be made while keeping within the spirit and scope of the invention. Specific embodiments disclosed herein are not intended to limit the scope of protection, which should be determined solely by the claims. All publications and references disclosed herein are incorporated in their entirety by reference.

Tables

TABLE 1

| FOR primers used to generate *Enterobacteria phage* λ PCR product from Taiwo et al., 2012 | | |
|---|---|---|
| Name | Forward Primer | Reverse Primer |
| 1CpG | GAGGTGATAAAATTAACTG C (SEQ ID NO: 1) | GGCTCTACCATATCTCCTA (SEQ ID NO: 2) |

TABLE 1-continued

FOR primers used to generate *Enterobacteria phage λ* PCR product from Taiwo et al., 2012

| Name | Forward Primer | Reverse Primer |
|---|---|---|
| 5CpG | CATGTCCAGAGCTCATTC (SEQ ID NO: 3) | GTTTAAAATCACTAGGCGA (SEQ ID NO: 4) |
| 1 OC pG | CTGACCATTTCCATCATTC (SEQ ID NO: 5) | GTAACTAAACAGGAGCCG (SEQ ID NO: 6) |
| 150p0 | ATGTATCCATTGAGCATTG CC (SEQ ID NO: 7) | CACGAATCAGCGGTAAAGG T( SEQ ID NO: 8) |
| 20CpGL | GAGATATGGTAGAGCCGCA GA (SEQ ID NO: 9) | TTTCAGCAGCTACAGTCAG AATTT (SEQ ID NO: 10) |
| 20CpGS | CGATGGGTTAATTCGCTCG TTGTGG (SEQ ID NO: 11) | GCACAACGGAAAGAGCACT G (SEQ ID NO: 12) |

TABLE 2

Number of reads and mapping efficiency of sequenced MeDIP-seq and cfMeDIP-seq libraries prepared using various concentrations of HCT116 cell line DNA sheared to mimic cfDNA, to human Hg19 genome and A genome. For starting concentrations less than 100 ng, the samples were topped up with exogenous λ DNA to artificially increase the starting amount to 100 ng prior to MeDIP.

| Sample | # of Raw reads | # of Aligned reads to human genome (Hg19) | Mapping efficiency to human genome (Hg19) | # of Aligned reads to λ genome | Mapping efficiency to λ genome |
|---|---|---|---|---|---|
| Input | 74,504,053 | 71,343,168 | 95.76 | 12 | 0.00 |
| 100 ng Replicate 1 | 55,396,238 | 50,472,273 | 91.11 | 0 | 0.00 |
| 100 ng Replicate 2 | 66,569,209 | 60,770,277 | 91.29 | 1 | 0.00 |
| 10 ng Replicate 1 | 70,054,607 | 64,020,441 | 91.39 | 0 | 0.00 |
| 10 ng Replicate 2 | 58,297,539 | 53,308,777 | 91.44 | 0 | 0.00 |
| 5 ng Replicate 1 | 65,845,430 | 60,540,743 | 91.94 | 1 | 0.00 |
| 5 ng Replicate 2 | 64,750,879 | 59,358,412 | 91.67 | 0 | 0.00 |
| 1 ng Replicate 1 | 35,102,361 | 32,258,451 | 91.90 | 0 | 0.00 |
| 1 ng Replicate 2 | 33,881,118 | 31,194,711 | 92.07 | 0 | 0.00 |

TABLE 3A

Number of reads and mapping efficiency of sequenced cfMeDIP-seq libraries prepared using cfDNA from pancreatic cancer patients, to human Hg19 genome and λ genome.

| Case | # of Raw reads | # of Aligned Reads | Mapping efficiency to human genome (Hg_19) | # of Aligned reads to λ genome | Mapping efficiency to λ genome |
|---|---|---|---|---|---|
| 1 | 49,970,366 | 46,120,982 | 92.30 | 1 | 0.00 |
| 2 | 55,642,277 | 50,829,279 | 91.35 | 0 | 0.00 |
| 3 | 48,034,998 | 43,973,048 | 91.54 | 0 | 0.00 |
| 4 | 56,274,788 | 51,456,978 | 91.44 | 0 | 0.00 |
| 5 | 50,999,157 | 46,608,023 | 91.39 | 1 | 0.00 |
| 6 | 55,127,192 | 50,906,050 | 92.34 | 0 | 0.00 |
| 7 | 53,955,550 | 49,028,646 | 90.87 | 0 | 0.00 |
| 8 | 55,482,420 | 51,194,364 | 92.27 | 1 | 0.00 |

TABLE 3A-continued

Number of reads and mapping efficiency of sequenced cfMeDIP-seq libraries prepared using cfDNA from pancreatic cancer patients, to human Hg19 genome and λ genome.

| Case | # of Raw reads | # of Aligned Reads | Mapping efficiency to human genome (Hg_19) | # of Aligned reads to λ genome | Mapping efficiency to λ genome |
|---|---|---|---|---|---|
| 9 | 57,626,914 | 53,446,965 | 92.75 | 0 | 0.00 |
| 10 | 58,397,946 | 53,904,793 | 92.31 | 0 | 0.00 |
| 11 | 59,048,723 | 54,529,214 | 92.35 | 0 | 0.00 |
| 12 | 54,514,051 | 49,619,174 | 91.02 | 1 | 0.00 |
| 13 | 70,758,028 | 63,842,005 | 90.23 | 0 | 0.00 |
| 14 | 60,317,171 | 55,124,638 | 91.39 | 0 | 0.00 |
| 15 | 45,187,670 | 41,341,336 | 91.49 | 0 | 0.00 |
| 16 | 50,755,880 | 46,309,615 | 91.24 | 2 | 0.00 |
| 17 | 51,582,370 | 47,256,012 | 91.61 | 1 | 0.00 |
| 18 | 52,081,710 | 47,763,766 | 91.71 | 0 | 0.00 |
| 19 | 53,845,426 | 48,602,035 | 90.26 | 0 | 0.00 |
| 20 | 48,133,619 | 43,658,379 | 90.70 | 0 | 0.00 |
| 21 | 54,237,903 | 49,286,048 | 90.87 | 0 | 0.00 |

TABLE 3A-continued

Number of reads and mapping efficiency of sequenced cfMeDIP-seq libraries prepared using cfDNA from pancreatic cancer patients, to human Hg19 genome and λ genome.

| Case | # of Raw reads | # of Aligned Reads | Mapping efficiency to human genome (Hg_19) | # of Aligned reads to λ genome | Mapping efficiency to λ genome |
|---|---|---|---|---|---|
| 21 | 54,237,903 | 49,286,048 | 90.87 | 0 | 0.00 |
| 22 | 58,627,625 | 53,654,439 | 91.52 | 1 | 0.00 |
| 23 | 52,748,183 | 49,179,765 | 93.23 | 0 | 0.00 |
| 24 | 60,072,026 | 55,046,660 | 91.63 | 0 | 0.00 |

TABLE 3B

Number of reads and mapping efficiency of sequenced cfMeDIP-seq libraries prepared using cfDNA from healthy donors, to human Hg19 genome and λ genome.

| Control | # of Raw reads | # of Aligned Reads | Mapping efficiency to human genome (Hg19) | # of Aligned reads to λ genome | Mapping efficiency to λ genome |
|---|---|---|---|---|---|
| 1 | 44,162,563 | 40,184,943 | 90.99 | 1 | 0.00 |
| 2 | 33,350,539 | 30,585,488 | 91.71 | 0 | 0.00 |
| 3 | 43,937,337 | 40,160,512 | 91.40 | 0 | 0.00 |
| 4 | 44,292,409 | 40,182,945 | 90.72 | 0 | 0.00 |
| 5 | 54,732,283 | 50,135,420 | 91.60 | 0 | 0.00 |
| 6 | 52,576,198 | 48,139,158 | 91.56 | 0 | 0.00 |
| 7 | 47,619,930 | 42,684,336 | 89.64 | 0 | 0.00 |
| 8 | 51,213,827 | 46,529,314 | 90.85 | 0 | 0.00 |
| 9 | 48,935,317 | 44,487,195 | 90.91 | 1 | 0.00 |
| 10 | 56,055,796 | 51,971,671 | 92.71 | 0 | 0.00 |
| 11 | 54,769,256 | 50,075,252 | 91.43 | 0 | 0.00 |
| 12 | 50,625,023 | 45,869,378 | 90.61 | 1 | 0.00 |
| 13 | 51,015,277 | 46,252,402 | 90.66 | 0 | 0.00 |
| 14 | 58,266,281 | 53,191,317 | 91.29 | 1 | 0.00 |
| 15 | 55,663,935 | 50,447,271 | 90.63 | 0 | 0.00 |
| 16 | 44,004,381 | 39,533,012 | 89.84 | 1 | 0.00 |
| 17 | 55,459,971 | 50,786,298 | 91.57 | 0 | 0.00 |
| 18 | 52,610,463 | 48,293,244 | 91.79 | 0 | 0.00 |
| 19 | 46,806,153 | 42,677,554 | 91.18 | 0 | 0.00 |
| 20 | 63,267,324 | 57,692,667 | 91.19 | 0 | 0.00 |
| 21 | 51,213,236 | 46,637,533 | 91.07 | 0 | 0.00 |
| 22 | 54,380,628 | 49,267,997 | 90.60 | 0 | 0.00 |
| 23 | 44,608,650 | 40,685,531 | 91.21 | 0 | 0.00 |
| 24 | 52,118,117 | 47,734,519 | 91.59 | 0 | 0.00 |

TABLE 4A

Corresponding gender and age of pancreatic cancer patients

| Case | Sex (1 = Male, 2 = Female) | Age Range |
|---|---|---|
| 1 | 1 | 70 < 75 |
| 2 | 2 | 65 < 70 |
| 3 | 1 | 50 < 55 |
| 4 | 1 | 65 < 70 |
| 5 | 2 | 60 < 65 |
| 6 | 2 | 80 < 85 |
| 7 | 1 | 60 < 65 |
| 8 | 2 | 70 < 75 |
| 9 | 2 | 60 < 65 |
| 10 | 1 | 50 < 55 |
| 11 | 1 | 70 < 75 |
| 12 | 2 | 50 < 55 |
| 13 | 1 | 60 < 65 |
| 14 | 2 | 75 < 80 |
| 15 | 2 | 55 < 60 |
| 16 | 2 | 80 < 85 |
| 17 | 1 | 55 < 60 |
| 18 | 2 | 55 < 60 |
| 19 | 2 | 65 < 70 |
| 20 | 2 | 60 < 65 |
| 21 | 1 | 65 < 70 |
| 22 | 1 | 65 < 70 |
| 23 | 2 | <50 |
| 24 | 1 | 65 < 70 |

TABLE 4B

Corresponding gender and age of healthy donors

| Control | Sex (1 = Male, 2 = Female) | Age Range |
|---|---|---|
| 1 | 1 | 60 < 65 |
| 2 | 2 | 55 < 60 |
| 3 | 1 | 70 < 75 |
| 4 | 1 | 85+ |

TABLE 4B-continued

Corresponding gender and age of healthy donors

| Control | Sex (1 = Male, 2 = Female) | Age Range |
|---|---|---|
| 5 | 2 | 80 < 85 |
| 6 | 2 | <50 |
| 7 | 1 | 80 < 85 |
| 8 | 2 | 60 < 65 |
| 9 | 2 | 85+ |
| 10 | 1 | 60 < 65 |
| 11 | 1 | 70 < 75 |
| 12 | 2 | 55 < 60 |
| 13 | 1 | 50 < 55 |
| 14 | 2 | 70 < 75 |
| 15 | 2 | 70 < 75 |
| 16 | 2 | 80 < 85 |
| 17 | 1 | 50 < 55 |
| 18 | 2 | 70 < 75 |
| 19 | 2 | 70 < 75 |
| 20 | 2 | 70 < 75 |
| 21 | 1 | 75 < 80 |
| 22 | 1 | <50 |
| 23 | 2 | 60 < 65 |
| 24 | 1 | 80 < 85 |

TABLE 5

Pathology of adenocarcinoma of pancreas case samples

| Pathology Stage | Number of cases |
|---|---|
| I-II | 23 |
| III-IV | 1 |

TABLE 6A

Number of reads, mapping efficiency, bisulfite conversion efficiency and CpG coverage
of sequenced RRBS libraries prepared using laser-capture microdissection-enriched
(LCM) tumor samples with high tumor purity from pancreatic cancer patients.

| Tumor from Case | # of Raw reads | # of Aligned reads to human genome (Hg19) | Mapping efficiency to human genome (Hg19) | Bisulfite Conversion Efficiency | # of CpGs with a minimum coverage of 10 reads |
|---|---|---|---|---|---|
| 1 | 36,348,593 | 22,050,682 | 60.7 | 99.65 | 1,152,313 |
| 2 | 56,788,591 | 35,512,606 | 62.5 | 98.29 | 1,790,326 |
| 3 | 55,115,742 | 35,229,781 | 63.9 | 98.94 | 1,630,272 |
| 4 | 58,503,145 | 37,373,806 | 63.9 | 99.48 | 1,777,824 |
| 5 | 64,364,708 | 34,274,401 | 63.0 | 98.84 | 2,053,577 |
| 6 | 57,291,238 | 34,912,515 | 60.9 | 99.23 | 2,001,726 |
| 7 | 42,683,835 | 25,509,282 | 59.8 | 97.79 | 1,471,270 |
| 8 | 51,393,779 | 31,437,264 | 61.2 | 99.52 | 1,745,355 |
| 9 | 66,023,766 | 41,284,714 | 62.5 | 99.17 | 1,788,895 |
| 10 | 37,026,164 | 20,805,815 | 56.2 | 98.67 | 1,435,724 |
| 11 | 40,053,025 | 22,116,738 | 55.2 | 99.47 | 1,521,135 |
| 12 | 42,065,012 | 23,591,687 | 56.1 | 98.22 | 1,599,425 |
| 13 | 34,527,362 | 22,101,495 | 64.0 | 99.79 | 733,408 |
| 14 | 38,624,627 | 23,317,534 | 60.4 | 99.82 | 952,714 |
| 15 | 36,799,407 | 22,072,921 | 60.0 | 98.45 | 1,442,393 |
| 16 | 33,672,535 | 19,735,978 | 58.6 | 98.70 | 1,064,718 |
| 17 | 51,918,938 | 32,239,409 | 62.1 | 99.08 | 1,810,260 |
| 18 | 26,344,807 | 15,531,839 | 59.0 | 99.87 | 792,650 |
| 19 | 43,744,321 | 26,819,066 | 61.3 | 98.45 | 1,510,987 |
| 20 | 49,861,059 | 28,520,788 | 57.2 | 97.75 | 1,852,841 |
| 21 | 44,061,826 | 27,903,839 | 63.3 | 99.68 | 1,368,522 |
| 22 | 55,029,698 | 33,444,993 | 60.8 | 99.10 | 2,006,233 |
| 23 | 70,468,323 | 45,424,428 | 64.5 | 97.86 | 2,331,030 |
| 24 | 42,043,232 | 24,828,943 | 59.1 | 97.44 | 1,520,504 |

TABLE 6B

Number of reads, mapping efficiency, bisulfite conversion efficiency and CpG coverage
of sequenced RRBS libraries prepared using laser-capture microdissection-enriched
(LCM) normal tissue samples from pancreatic cancer patients healthy donors.

| Normal Tissue from Case | # of Raw reads | # of Aligned reads to human genome (Hg19) | Mapping efficiency to human genome (Hg19) | Bisulfite Conversion Efficiency | # of CpGs with a minimum coverage of 10 reads |
|---|---|---|---|---|---|
| 1 | 44,991,468 | 25,708,044 | 57.1 | 98.88 | 1,688,179 |
| 2 | 50,603,038 | 30,001,913 | 59.3 | 99.81 | 1,767,046 |
| 3 | 50,790,690 | 31,585,415 | 62.2 | 99.61 | 1,733,966 |
| 4 | 49,480,382 | 30,017,286 | 60.7 | 99.60 | 1,895,462 |
| 5 | 46,587,496 | 29,742,054 | 63.8 | 98.94 | 1,648,785 |
| 6 | 55,402,162 | 33,193,299 | 59.9 | 99.10 | 2,149,673 |
| 7 | 35,010,018 | 20,646,990 | 59.0 | 99.83 | 1,188,194 |
| 8 | 51,130,341 | 30,543,069 | 59.7 | 99.64 | 1,780,696 |
| 9 | 53,415,206 | 32,049,549 | 60.0 | 99.63 | 1,720,213 |
| 10 | 40,977,129 | 22,109,663 | 54.0 | 99.60 | 1,690,112 |
| 11 | 37,913,346 | 20,202,691 | 53.3 | 98.35 | 638,859 |
| 12 | 47,943,368 | 26,962,401 | 66.2 | 97.74 | 1,467,609 |
| 13 | 28,416,315 | 16,532,481 | 58.2 | 98.36 | 1,214,093 |
| 14 | 34,809,298 | 20,603,577 | 59.2 | 99.26 | 1,105,920 |
| 15 | 36,930,467 | 21,513,886 | 58.3 | 99.76 | 1,434,653 |
| 16 | 38,762,192 | 23,242,114 | 60.0 | 99.79 | 1,539,278 |
| 17 | 51,257,989 | 29,870,486 | 58.3 | 99.66 | 1,915,596 |
| 18 | 28,789,569 | 17,038,843 | 59.2 | 98.21 | 1,222,106 |
| 19 | 41,387,115 | 25,996,349 | 62.8 | 98.57 | 1,712,186 |
| 20 | 31,704,499 | 17,421,599 | 54.9 | 99.41 | 977,256 |
| 21 | 44,152,396 | 26,604,688 | 60.3 | 09.68 | 1,646,272 |
| 22 | 46,462,469 | 27,012,950 | 58.1 | 99.43 | 1,940,763 |
| 23 | 53,534,041 | 33,359,195 | 62.3 | 99.50 | 1,650,915 |
| 24 | 37,042,798 | 22,775,661 | 61.5 | 99.31 | 435,114 |

REFERENCES

1 Sharma, S., Kelly, T. K. & Jones, P. A. Epigenetics in cancer. *Carcinogenesis* 31, 27-36, doi: 10.1093/carcin/bgp220 (2010).

2 Variey, K. E. et a/. Dynamic DNA methylation across diverse human cell lines and tissues. *Genome Res* 23, 555567, doi: 10.1101/gr.147942.112 (2013).

3 Sturm, D. et al. Hotspot mutations in H3F3A and IDHI define distinct epigenetic and biological subgroups of glioblastoma. *Cancer Cell* 22, 425-437, do1: 10.1016/j.ccr.2012.08.024 (2012).

4 Mack. S. C. et al. Epigenomic alterations define lethal CIMP-positive ependymomas of infancy. *Nature* 506, 445-450, doi: 10.1038/nature13108 (2014).

Hinoue, T. et a/. Genome-scale analysis of aberrant DNA methylation in colorectal cancer. *Genome Res* 22, 271-282, doi: 10.1101/gr. 117523.110 (2012).

6 Stirzaker, C. et al. Methylome sequencing in triple-negative breast cancer reveals distinct methylation clusters with prognostic value. *Nat Commun* 6, 5899, do1: 10.1038/ncomms6899 (2015).

7 Fang, F. et al. Breast cancer methylomes establish an epigenomic foundation for metastasis. *Sci Transl Med* 3, 75ra25, doi: 10.1126/scitranslmed.3001875 (2011).

8 Mikeska, T. & Craig, J_ M. DNA methylation biomarkers: cancer and beyond_ *Genes (Basel)* 5, 821-864, doi: 10.3390/genes5030821 (2014).

9 Diaz, L A., Jr. & Bardelli, A. Liquid biopsies: genotyping circulating tumor DNA. *J C/in Once!* 32, 579-586, doi: 10.1200/JC0,2012.45.2011 (2014).

Snyder, T. M., Khush, K. K., Valentine, H. A. & Quake, S. R. Universal noninvasive detection of solid organ transplant rejection_ *Proc Acad Sci USA* 108, 6229-6234, doi: 10.1073/pnas. 1013924108 (2011).

11 Chiu, R. W. et al. Noninvasive prenatal diagnosis of fetal chromosomal aneuploidy by massively parallel genomic sequencing of DNA in maternal plasma. *Proc Nat! Aced Sci USA* 105, 20458-0.20463, doi: 10.1073/pnas_0810641106 (2008).

12 Fan, H. C., Blumenfeld, Y. J., Chitkara, U., Hudgins, L & Quake, S. R. Noninvasive diagnosis of fetal aneuploidy by shotgun sequencing DNA from maternal blood. *Proc Natl Acad Sci USA* 105, 16266-16271, doi: 10.1073/pnas.0808319105 (2008).

13 Newman, A. M. et a/. An ultrasensitive method for quantitating circulating tumor DNA with broad patient coverage. *Nat Med* 20, 548-554, doi: 10.1038/nm.3519 (2014).

14 Aravanis, A. M., Lee, M. & Klausner, R. D. Next-Generation Sequencing of Circulating Tumor DNA for Early Cancer Detection. *Cell* 168, 571-574, doi: 10.1016/j.cell.2017.01.030 (2017).

15 Hoacitey, K. A. et al. Multiplatform analysis of 12 cancer types reveals molecular classification within and across tissues of origin. *Cell* 158, 929-944, doi: 10.1016/j.cell.2014.06.049 (2014).

16 Fieischhacker, M_& Schmidt, B. Circulating nucleic acids (CNAs) and cancer—a survey. *Biochim Biophys Acta* 1775, 181-232, doi: 10.1016/j.bbcan.2006.10.001 (2007).

17 Taiwo, O. et al. Methylome analysis using MeDIP-seq with low DNA concentrations. *Nat Protoc* 7, 617-636, doi: 10.1038/nprot.2012.012 (2012).

18 Gu, H. et al. Preparation of reduced representation bisulfite sequencing libraries for genome-scale DNA methylation profiling. *Nat Protoc* 6, 468-481, doi: 10.1038/nprot.2010.190 (2011).

19 Hung, E. C., Chiu, R. W. & Lo, Y. M. Detection of circulating fetal micleic acids: a review oᵹ methods and applications. *J Clin Pathol* 62, 308-313, doi: 10.1136/jcp.2007.048470 (2009).

20 Heinz, S. et al. Simple combinations of lineage-determining transcription factors prime cis-regulatory elements required for macrophage and B cell identities. *Mol Cell* 38, 576-589, doi: 10.1016/j.molcel.2010.05.004 (2010).

21 Consortium, G. T. Human genomics. The Genotype-Tissue Expression (GTEx) pilot analysis: multitissue gene regulation in humans. *Science* 348, 648-660, doi: 10.1126/science.1262110 (2015).

22 Su, A. I. et al. A gene atlas of the mouse and human protein-encoding transcriptomes. *Proc Natl Acad Sci USA* 101, 6062-6067, doi: 10.1073/pnas.0400782101 (2004).

23 Wu, C., Jin, X., Tsueng, G., Afrasiabi, C. & Su, A. 1. BioGPS: building your own mash-up of gene annotations and expression profiles. *Nucleic Acids Res* 44, 0313-316, doi: 10.1093/nar/gkv1104 (2016).

24 Bailey, P. et al. Genomic analyses identify molecular subtypes of pancreatic cancer. *Nature*, do1: 10.1038/nature16965 (2016).

25 Lienhard, M., Grimm, C., Markel, M., Herwig, R. & Chavez, L. MEOWS: genome-wide differential coverage analysis of sequencing data derived from DNA enrichment experiments. *Bioinformatics* 30, 284-286, doi: 10.1093/bioinformatics/btt650 (2014).

26 Akalin, A. et al. methylKit: a comprehensive R package for the analysis of genome-wide DNA methylation profiles. *Genome Biol* 13, R87, doi: 10.1186/gb-2012-13-10-r87 (2012).

27 Krueger, F. & Andrews, S. R. Bismark: a flexible aligner and methylation caller for Bisulfate-Seq applications. *Bioinformatics* 27, 1571-1572, doi: 10.1 093/bioinformaticsibtr167 (2011).

28 Hu, S. et al. DNA methylation presents distinct binding sites for human transcription factors. *Elife* 2, e00726, doi: 10.7554/eLife.00726 (2013).

29 Lui, Y. Y. et el. Predominant hematopoietic origin of cell-free DNA in plasma and serum after sex-mismatched bone marrow transplantation. *Clin Chem* 48, 421-427 (2002).

30 Snyder, M. W., Kircher, M., Hill, A. J., Daze, R. M. & Shendure, J. Cell-free DNA Comprises an In Vivo Nucleosome Footprint that Informs Its Tissues-Of-Origin. *Cell* 164, 57-68, doi: 10.1016/1.cell.2015.11.050 (2016).

---

What is claimed is:

1. A method for processing a nucleic acid sample of a subject, comprising:

processing one or more nucleic acid molecules derived from said nucleic acid sample, wherein said nucleic acid sample has no more than 50 nanograms (ng) of nucleic acid molecules, wherein said one or more nucleic acid molecules comprise one or more cell-free nucleic acid molecules, and wherein said one or more cell-free nucleic acid molecules comprise one or more methylated cell-free nucleic acid molecules, under conditions sufficient to increase a fold enrichment ratio associated with said one or more methylated cell-free nucleic acid molecules.

2. The method of claim 1, wherein said nucleic acid sample is a cell-free deoxyribonucleic acid (cfDNA) sample.

3. The method of claim 1, wherein said one or more cell-free nucleic acid molecules comprise one or more unmethylated nucleic acid molecules.

4. The method of claim 3, wherein said processing comprises determining (1) a presence of one or more methylated regions of said one or more methylated cell-free nucleic acid molecules and (2) a presence of one or more unmethylated regions of said one or more unmethylated nucleic acid molecules.

5. The method of claim 1, wherein said fold enrichment ratio is a ratio as determined by a comparison of said one or more methylated cell-free nucleic acid molecules to one or more unmethylated cell-free nucleic acid molecules.

6. The method of claim 1, wherein said fold enrichment ratio is at least 25.

7. The method of claim 1, wherein said processing further comprises combining said one or more nucleic acid molecules derived from said nucleic acid sample with a plurality of filler nucleic acid molecules.

8. The method of claim 1, wherein said processing further comprises capturing said one or more methylated cell-free nucleic acid molecules using one or more binders.

9. The method of claim 1, further comprising sequencing said one or more methylated cell-free nucleic acid molecules or derivatives thereof, thereby generating a methylation profile of said subject.

10. The method of claim 9, further comprising processing one or more nucleic acid molecules derived from another nucleic acid sample from a healthy subject.

11. The method of claim 10, wherein said processing of said one or more nucleic acid molecules derived from said another nucleic acid sample further comprises enriching for one or more methylated nucleic acid molecules derived from said another nucleic acid sample.

12. The method of claim 11, further comprising sequencing said one or more methylated nucleic acid molecules derived from said another nucleic acid sample, thereby generating a methylation profile of said healthy subject.

13. The method of claim 12, further comprising comparing said methylation profile of said subject to said methylation profile of said healthy subject.

14. A method for processing a nucleic acid sample of a subject, comprising:

processing one or more nucleic acid molecules derived from said nucleic acid sample to produce enriched nucleic acid molecules, wherein said one or more nucleic acid molecules comprise one or more cell-free nucleic acid molecules, under conditions sufficient to increase a CpG enrichment score as determined by dividing a CpG frequency of said enriched nucleic acid molecules by a CpG frequency of a human genome, wherein said CpG enrichment score is at least 2.

15. The method of claim 14, further comprising sequencing said enriched nucleic acid molecules or derivatives thereof, thereby generating a plurality of sequencing reads of said enriched nucleic acid molecules.

16. The method of claim 15, further comprising determining said CpG frequency of said enriched nucleic acid molecules based on said plurality of sequencing reads.

17. The method of claim 14, wherein one or more CpG regions of said enriched nucleic acid molecules comprise one or more methylated CpG regions.

18. The method of claim 14, wherein said CpG enrichment score is at least 3.

19. The method of claim 1, further comprising determining one or more characteristics of said one or more methylated cell-free nucleic acid molecules, thereby generating a methylation profile of said subject.

20. The method of claim 14, further comprising determining one or more characteristics of said enriched nucleic acid molecules, thereby generating a methylation profile of said subject.

* * * * *

SEQUENCE LISTING

```
Sequence total quantity: 12
SEQ ID NO: 1          moltype = DNA  length = 20
FEATURE               Location/Qualifiers
misc_feature          1..20
                      note = Description of Artificial Sequence: Synthetic primer
```

-continued

```
source                    1..20
                          mol_type = other DNA
                          organism = synthetic construct
SEQUENCE: 1
gaggtgataa aattaactgc                                        20

SEQ ID NO: 2              moltype = DNA   length = 19
FEATURE                   Location/Qualifiers
misc_feature              1..19
                          note = Description of Artificial Sequence: Synthetic primer
source                    1..19
                          mol_type = other DNA
                          organism = synthetic construct
SEQUENCE: 2
ggctctacca tatctccta                                         19

SEQ ID NO: 3              moltype = DNA   length = 18
FEATURE                   Location/Qualifiers
misc_feature              1..18
                          note = Description of Artificial Sequence: Synthetic primer
source                    1..18
                          mol_type = other DNA
                          organism = synthetic construct
SEQUENCE: 3
catgtccaga gctcattc                                          18

SEQ ID NO: 4              moltype = DNA   length = 19
FEATURE                   Location/Qualifiers
misc_feature              1..19
                          note = Description of Artificial Sequence: Synthetic primer
source                    1..19
                          mol_type = other DNA
                          organism = synthetic construct
SEQUENCE: 4
gtttaaaatc actaggcga                                         19

SEQ ID NO: 5              moltype = DNA   length = 19
FEATURE                   Location/Qualifiers
misc_feature              1..19
                          note = Description of Artificial Sequence: Synthetic primer
source                    1..19
                          mol_type = other DNA
                          organism = synthetic construct
SEQUENCE: 5
ctgaccattt ccatcattc                                         19

SEQ ID NO: 6              moltype = DNA   length = 18
FEATURE                   Location/Qualifiers
misc_feature              1..18
                          note = Description of Artificial Sequence: Synthetic primer
source                    1..18
                          mol_type = other DNA
                          organism = synthetic construct
SEQUENCE: 6
gtaactaaac aggagccg                                          18

SEQ ID NO: 7              moltype = DNA   length = 21
FEATURE                   Location/Qualifiers
misc_feature              1..21
                          note = Description of Artificial Sequence: Synthetic primer
source                    1..21
                          mol_type = other DNA
                          organism = synthetic construct
SEQUENCE: 7
atgtatccat tgagcattgc c                                      21

SEQ ID NO: 8              moltype = DNA   length = 20
FEATURE                   Location/Qualifiers
misc_feature              1..20
                          note = Description of Artificial Sequence: Synthetic primer
source                    1..20
                          mol_type = other DNA
                          organism = synthetic construct
SEQUENCE: 8
cacgaatcag cggtaaaggt                                        20

SEQ ID NO: 9              moltype = DNA   length = 21
FEATURE                   Location/Qualifiers
misc_feature              1..21
```

-continued

```
                            note = Description of Artificial Sequence: Synthetic primer
source                      1..21
                            mol_type = other DNA
                            organism = synthetic construct
SEQUENCE: 9
gagatatggt agagccgcag a                                                21

SEQ ID NO: 10               moltype = DNA   length = 24
FEATURE                     Location/Qualifiers
misc_feature                1..24
                            note = Description of Artificial Sequence: Synthetic primer
source                      1..24
                            mol_type = other DNA
                            organism = synthetic construct
SEQUENCE: 10
tttcagcagc tacagtcaga attt                                             24

SEQ ID NO: 11               moltype = DNA   length = 25
FEATURE                     Location/Qualifiers
misc_feature                1..25
                            note = Description of Artificial Sequence: Synthetic primer
source                      1..25
                            mol_type = other DNA
                            organism = synthetic construct
SEQUENCE: 11
cgatgggtta attcgctcgt tgtgg                                            25

SEQ ID NO: 12               moltype = DNA   length = 20
FEATURE                     Location/Qualifiers
misc_feature                1..20
                            note = Description of Artificial Sequence: Synthetic primer
source                      1..20
                            mol_type = other DNA
                            organism = synthetic construct
SEQUENCE: 12
gcacaacgga aagagcactg                                                  20
```